US 12,390,223 B2

(12) United States Patent
Witkowski et al.

(10) Patent No.: US 12,390,223 B2
(45) Date of Patent: Aug. 19, 2025

(54) SURGICAL CLIP APPLICATION DEVICE

(71) Applicants: BAXTER INTERNATIONAL INC., Deerfield, IL (US); BAXTER HEALTHCARE SA

(72) Inventors: Shannon Mary Witkowski, St. Paul, MN (US); James Douglas Studer, Beldenville, WI (US); Dustin Tyler Samm, West Chester Township, OH (US); Kyle Stewart, Cincinnati, OH (US); Jerome Joseph Schafer, Liberty Township, OH (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 323 days.

(21) Appl. No.: 17/901,463

(22) Filed: Sep. 1, 2022

(65) Prior Publication Data
US 2023/0075247 A1   Mar. 9, 2023

Related U.S. Application Data

(60) Provisional application No. 63/241,288, filed on Sep. 7, 2021.

(51) Int. Cl.
*A61B 17/128* (2006.01)
*A61B 17/00* (2006.01)

(52) U.S. Cl.
CPC ............... *A61B 17/1285* (2013.01); *A61B 2017/00367* (2013.01)

(58) Field of Classification Search
CPC . A61B 17/1285; A61B 17/122; A61B 17/128; A61B 17/083; A61B 2017/00367; A61B 2017/00296
See application file for complete search history.

(56) References Cited

U.S. PATENT DOCUMENTS 10,779,838 B1 *  9/2020  Blake, III .......... A61B 17/1285
2014/0379003 A1 * 12/2014  Blake, III .......... A61B 17/1285
                                                       606/143

OTHER PUBLICATIONS

International Search Report from corresponding International Patent Application No. PCT/US2022/042367, mailed Dec. 8, 2022.
Written Opinion from corresponding International Patent Application No. PCT/US2022/042367, mailed Dec. 8, 2022.
International Preliminary Report on Patentability (Under Chapter I) from corresponding International Patent Application No. PCT/US2022/042367, mailed Mar. 21, 2024. 9 pages.

* cited by examiner

*Primary Examiner* — Tan-Uyen T Ho
*Assistant Examiner* — Cherie M Poland
(74) *Attorney, Agent, or Firm* — K&L Gates LLP

(57) ABSTRACT

A surgical clip application device for applying and crimping surgical clips to ligate a vessel.

7 Claims, 50 Drawing Sheets

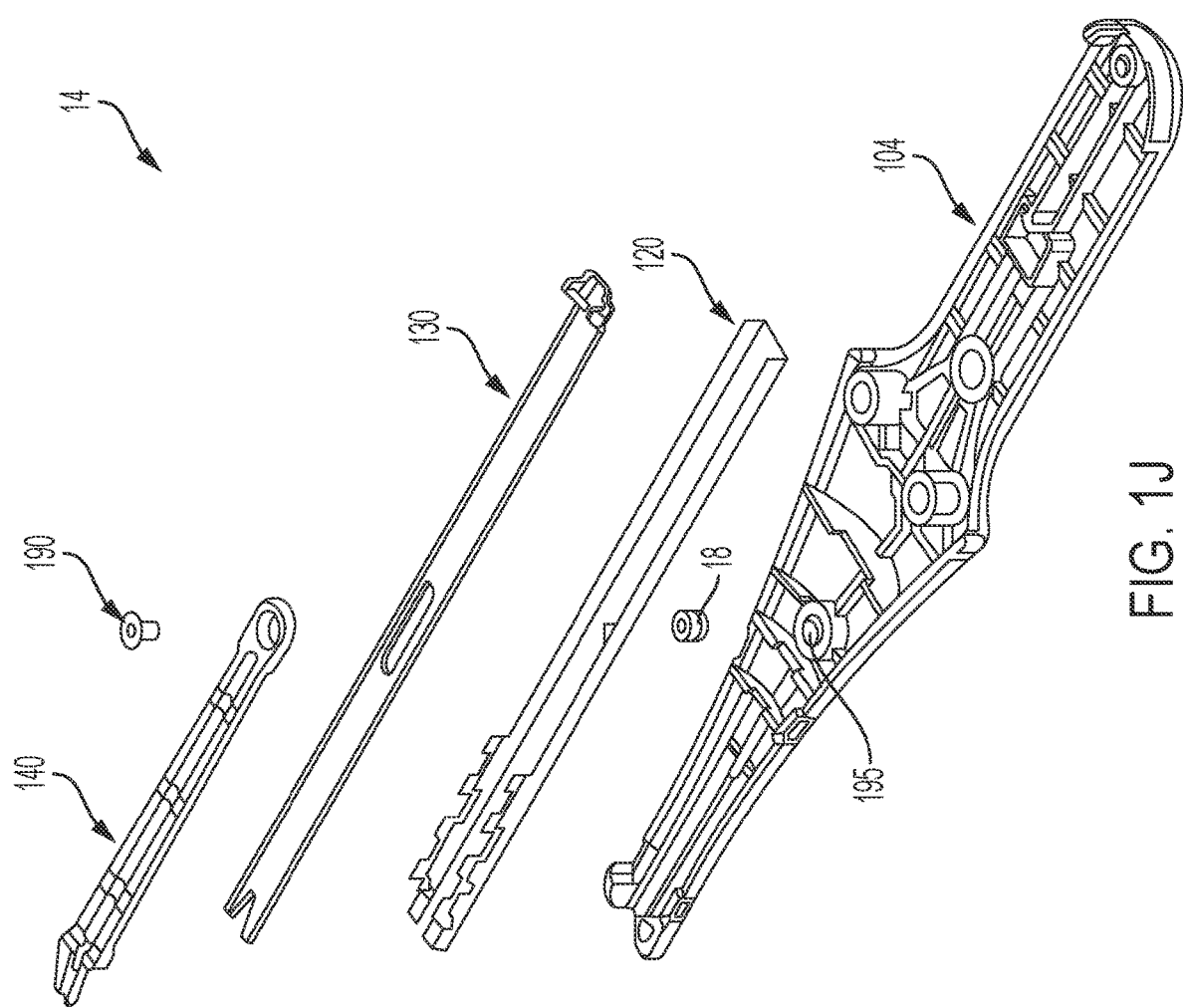

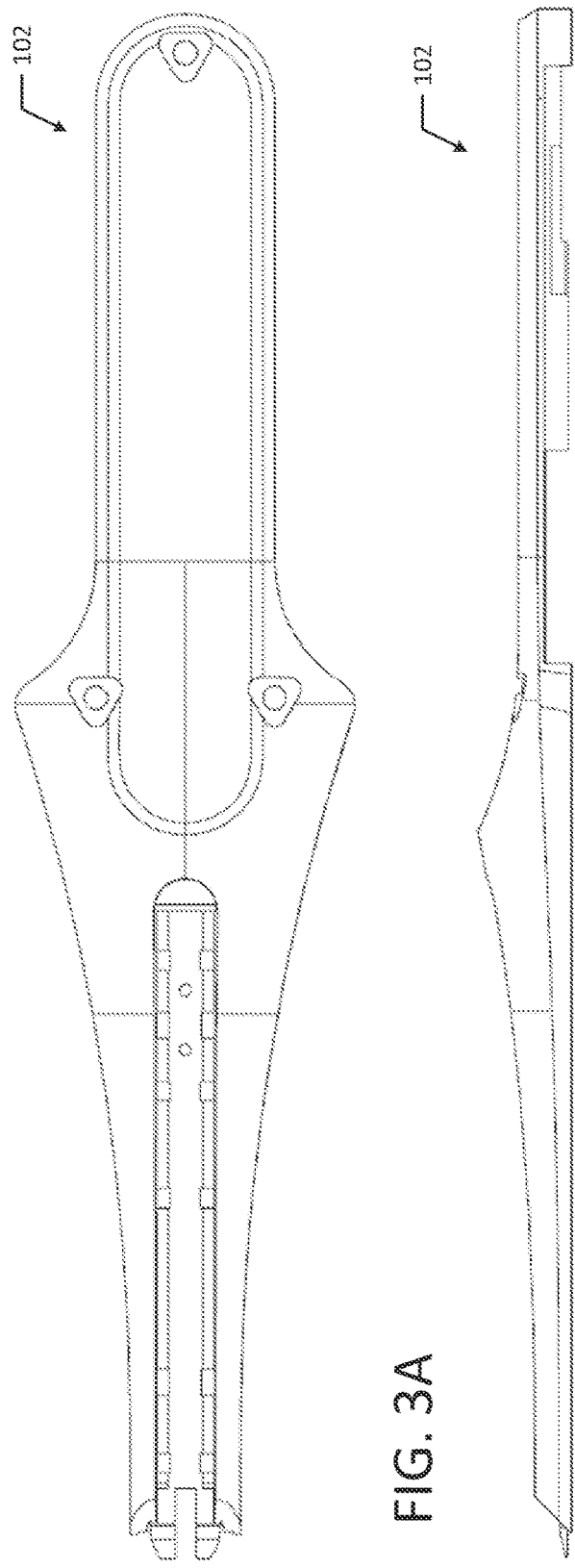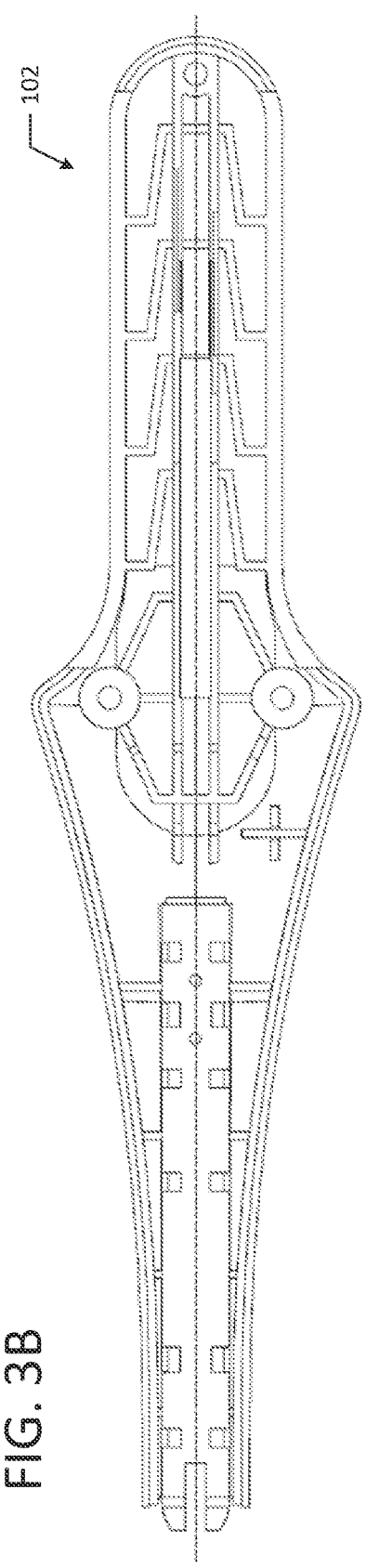
FIG. 3A  FIG. 3B  FIG. 3C

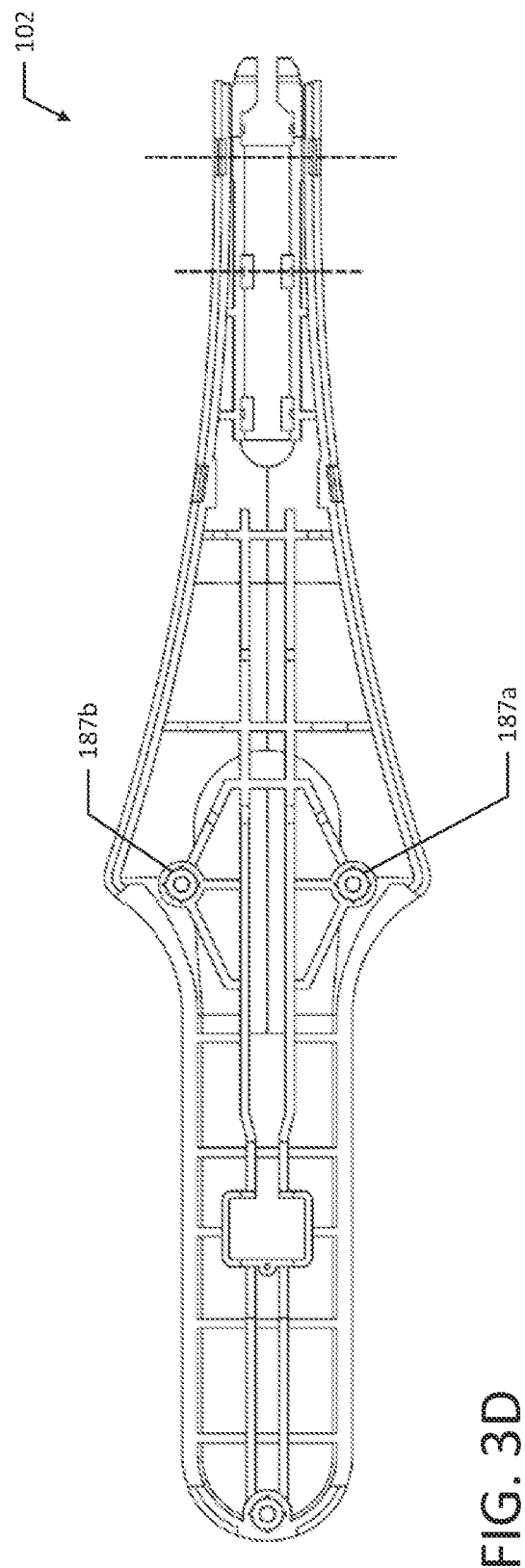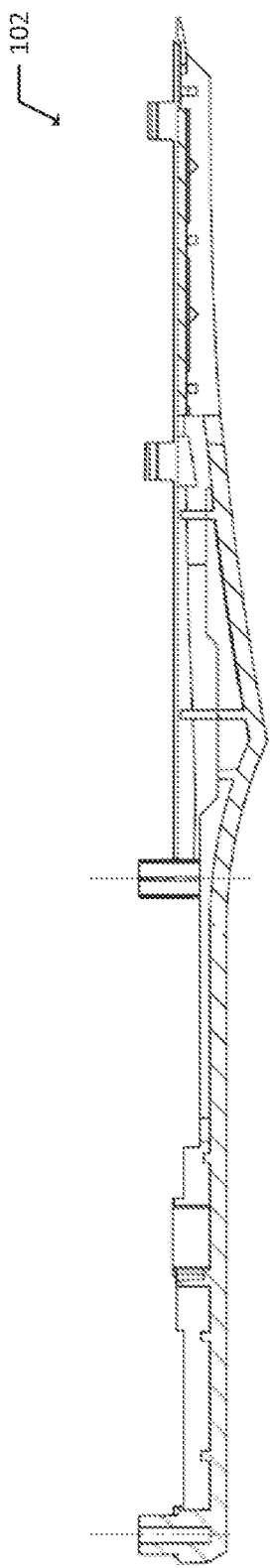
FIG. 3D
FIG. 3E

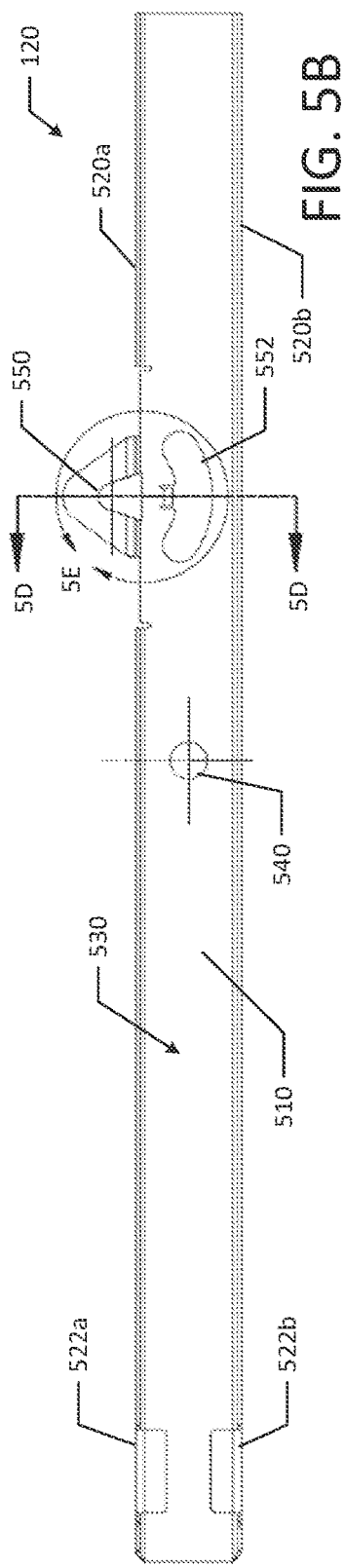
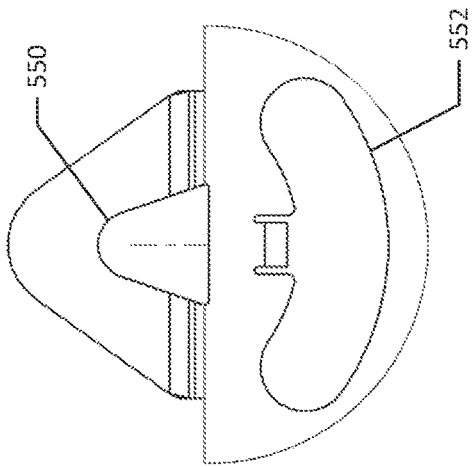
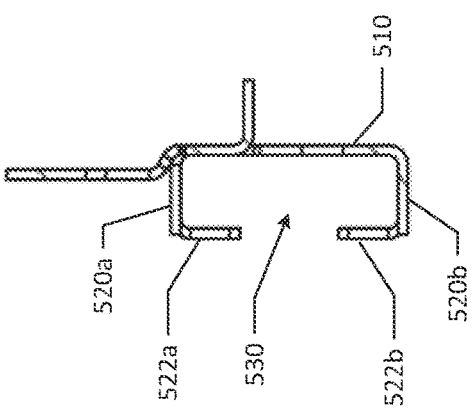

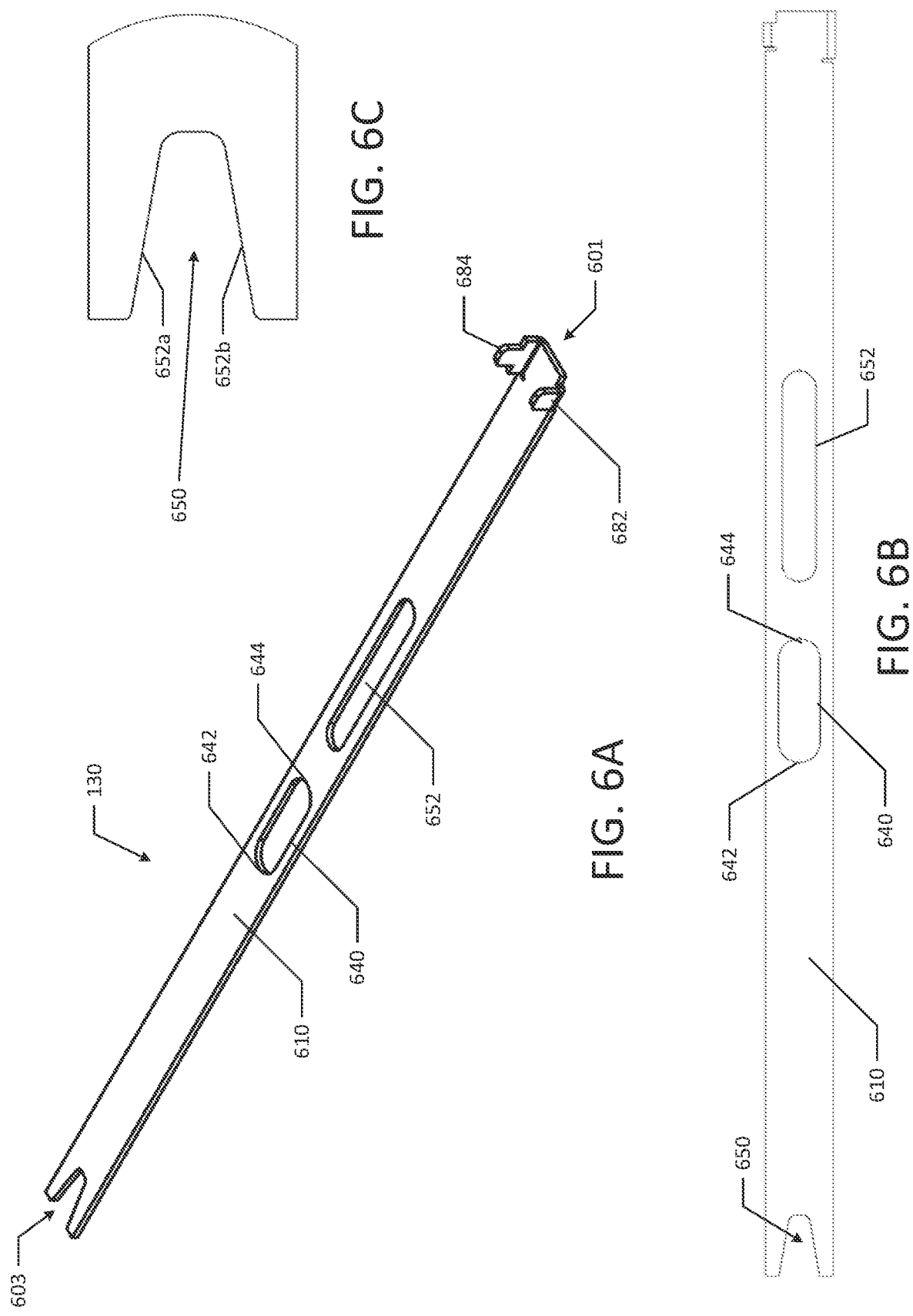

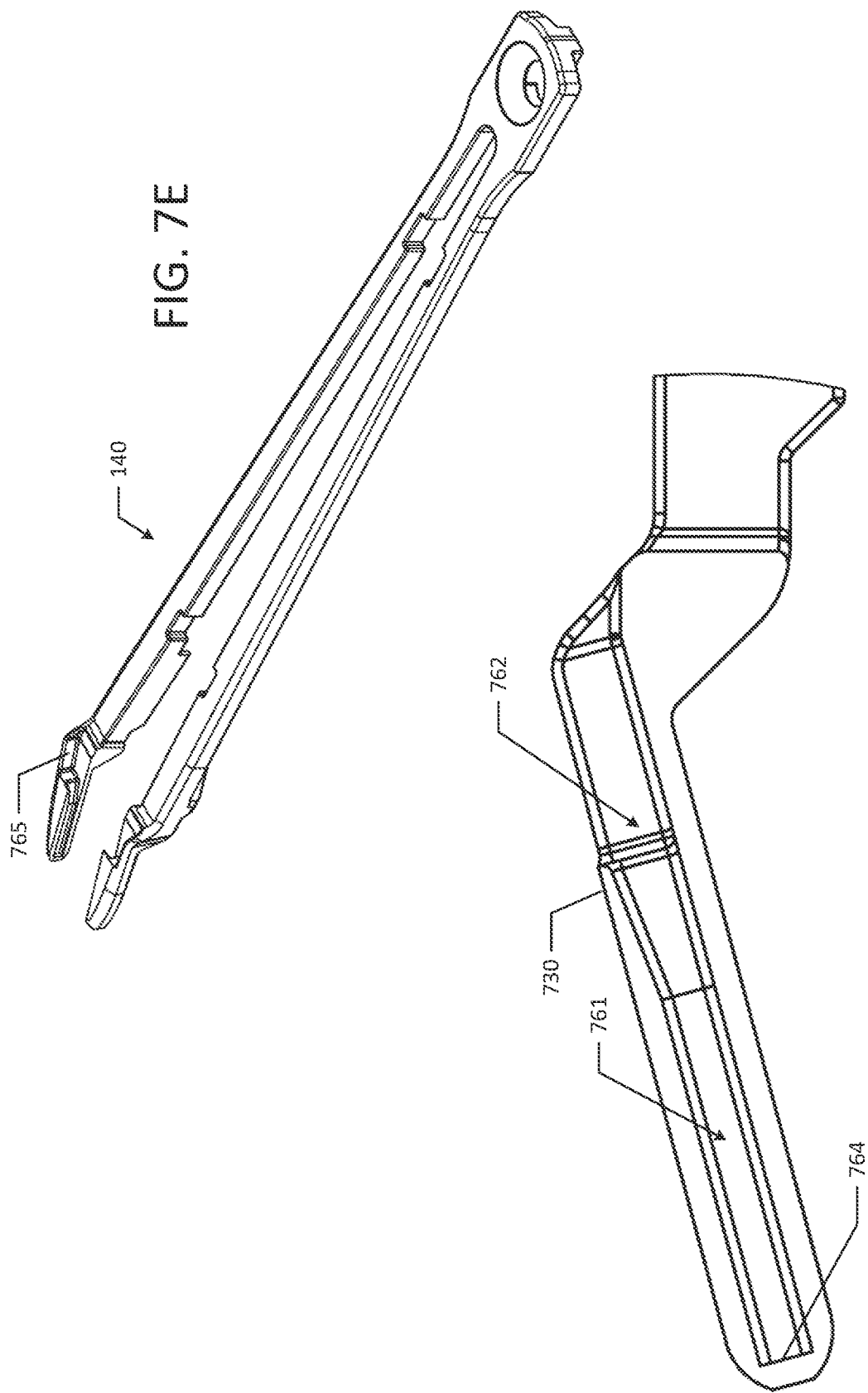

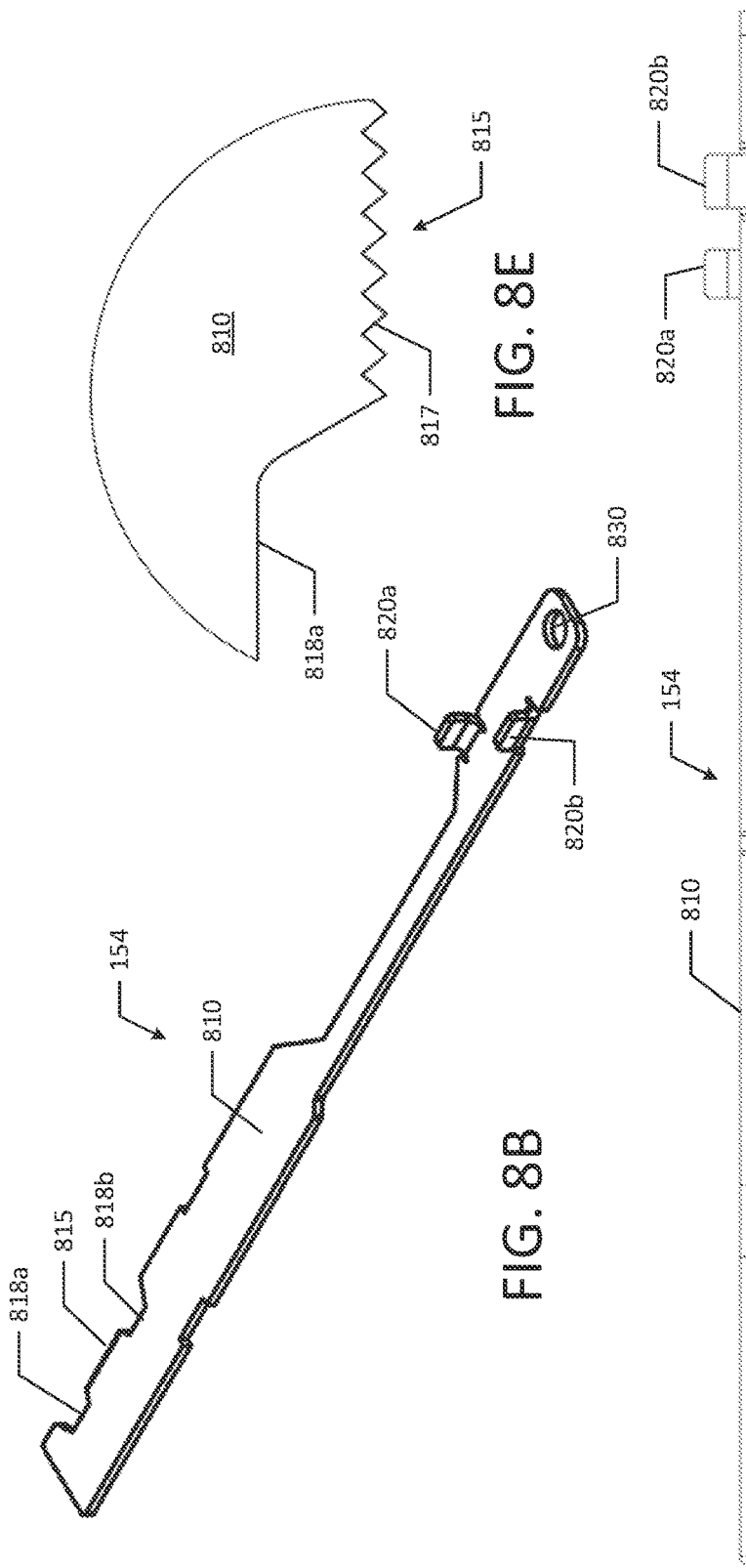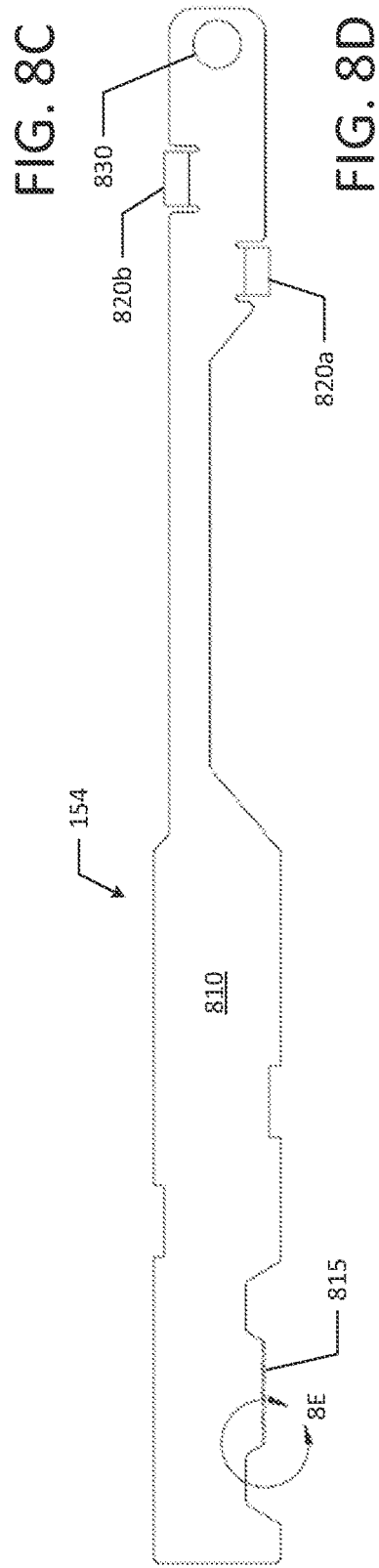

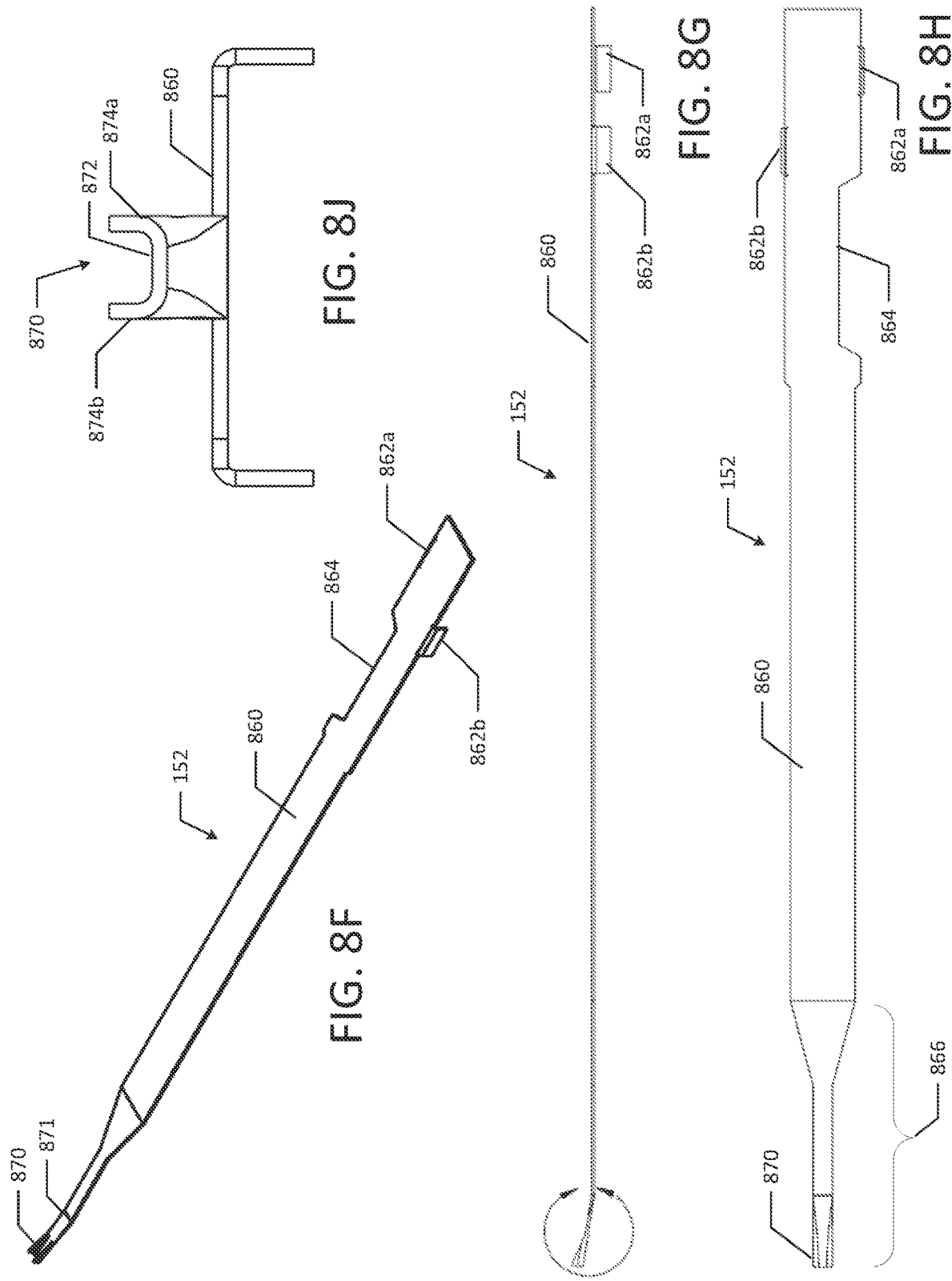

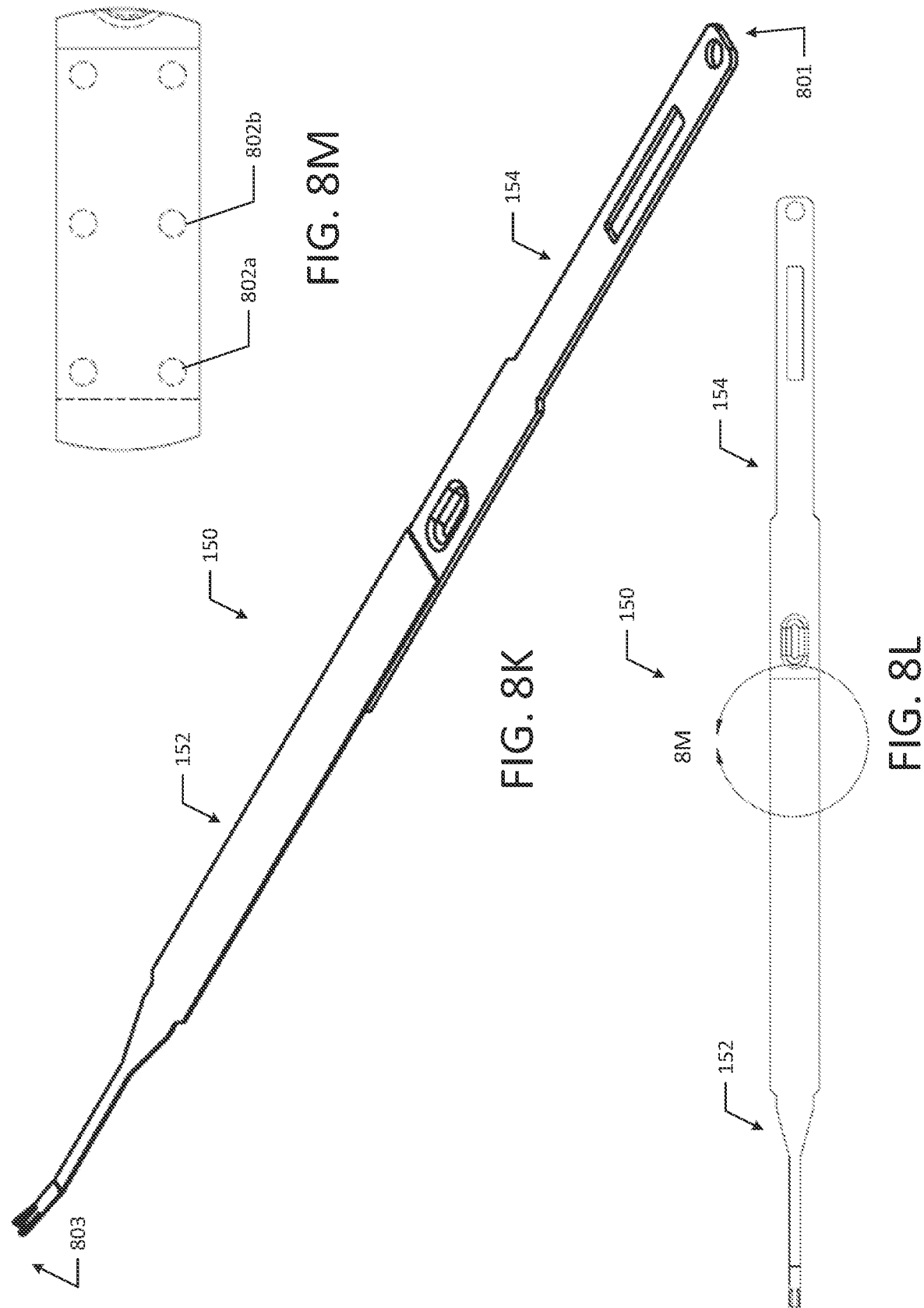

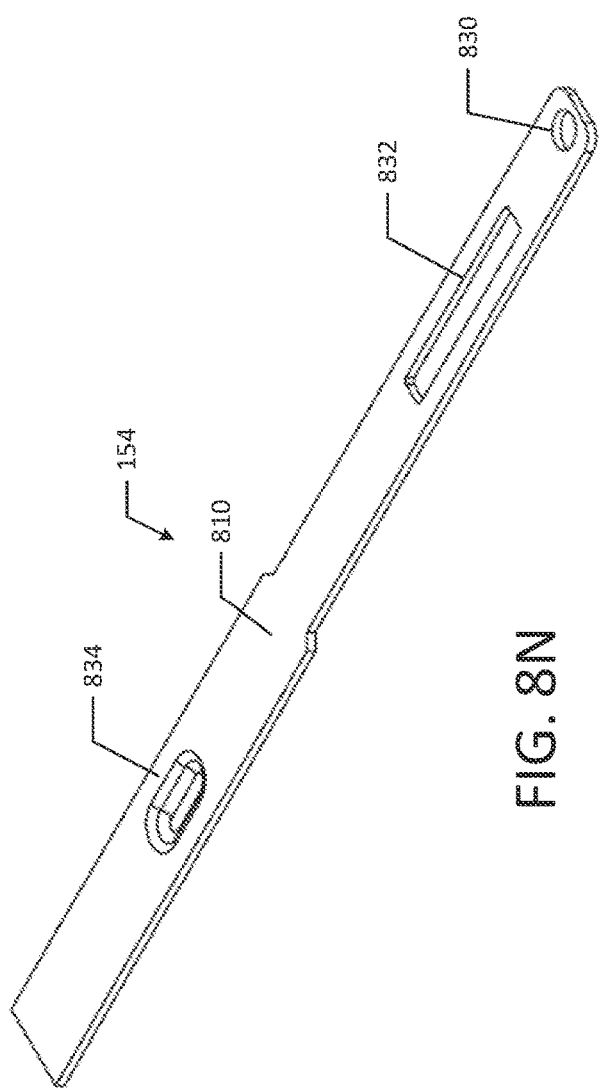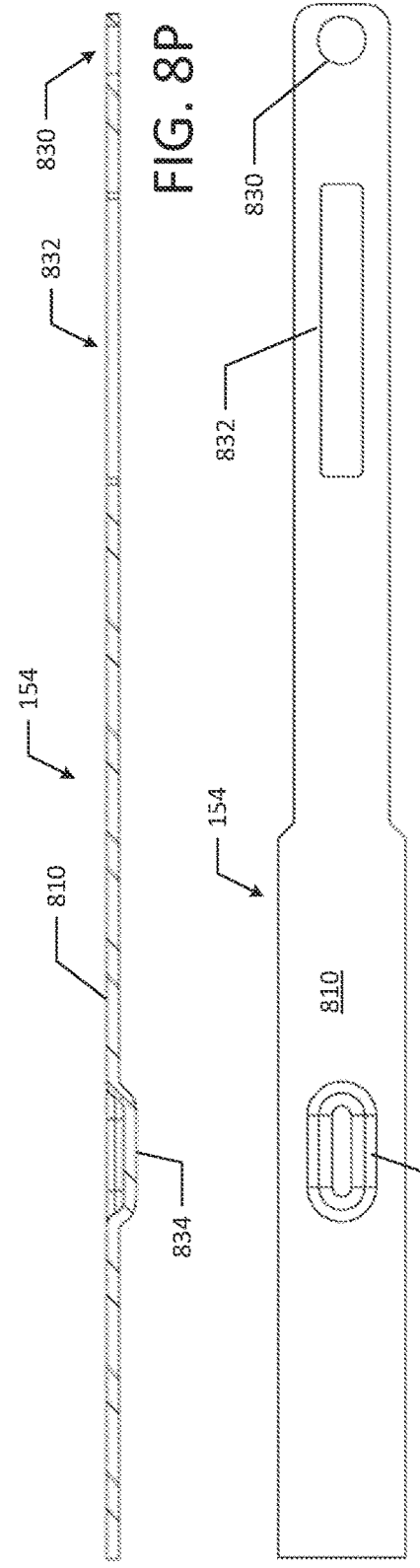

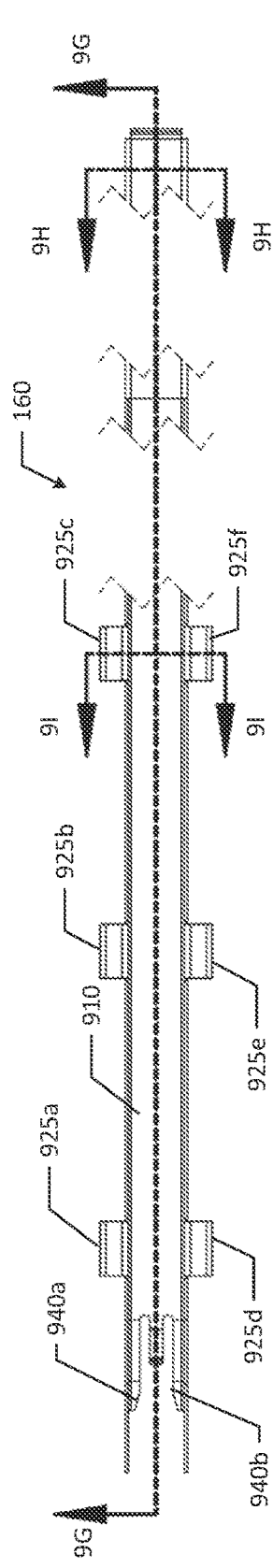
FIG. 9F
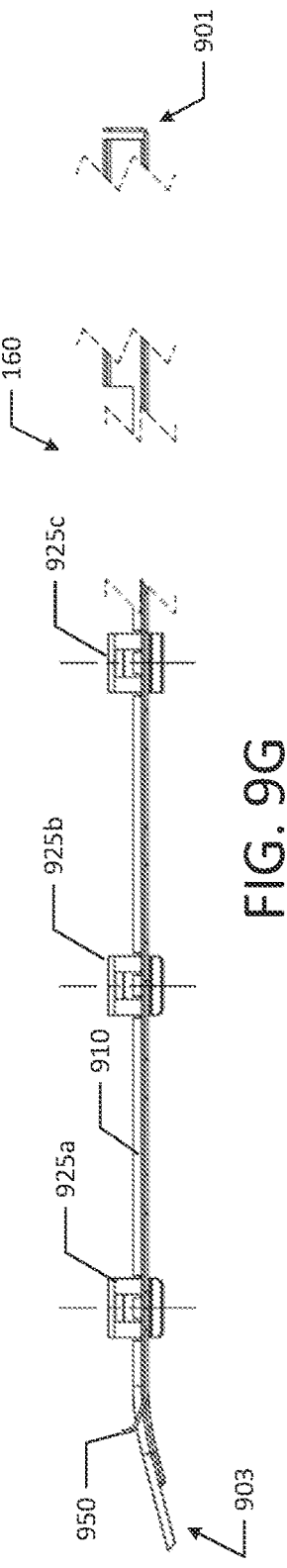
FIG. 9G
FIG. 9I
FIG. 9H

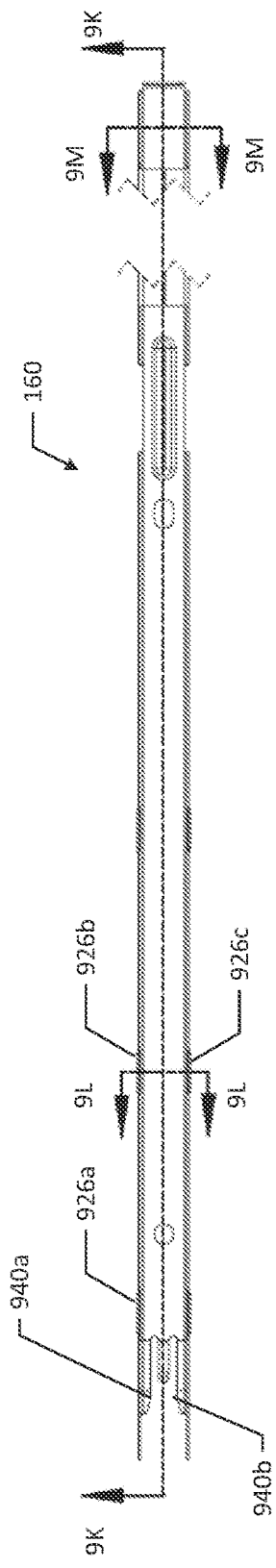
FIG. 9J
FIG. 9K
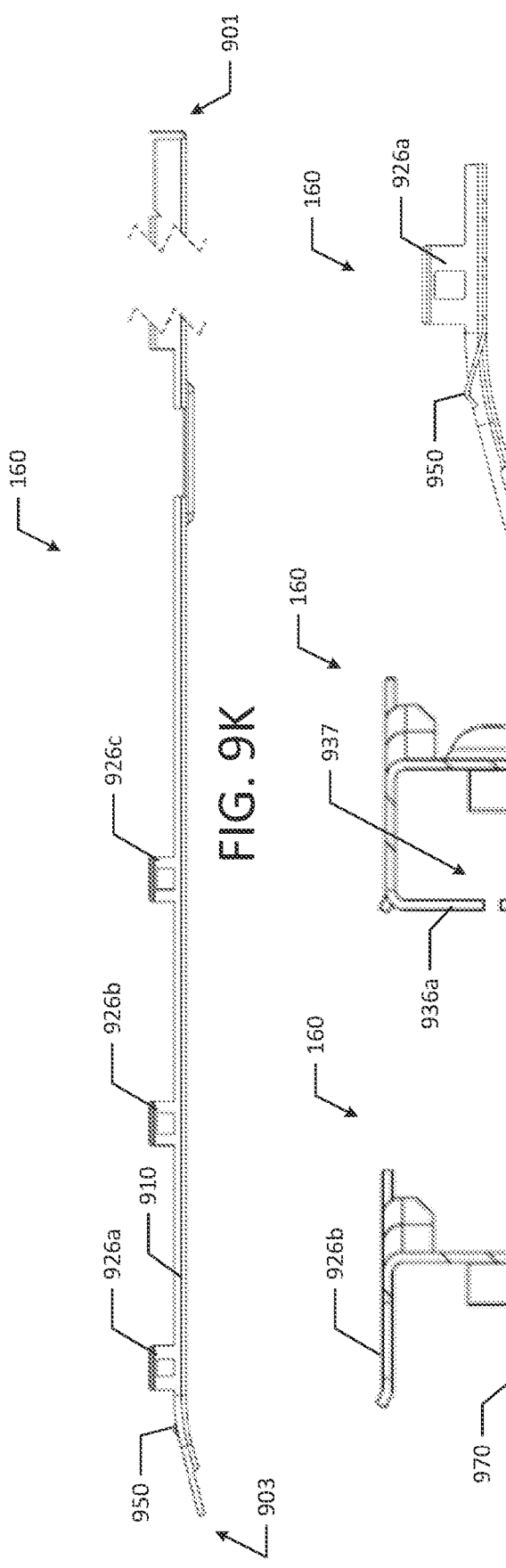
FIG. 9M
FIG. 9L
FIG. 9N

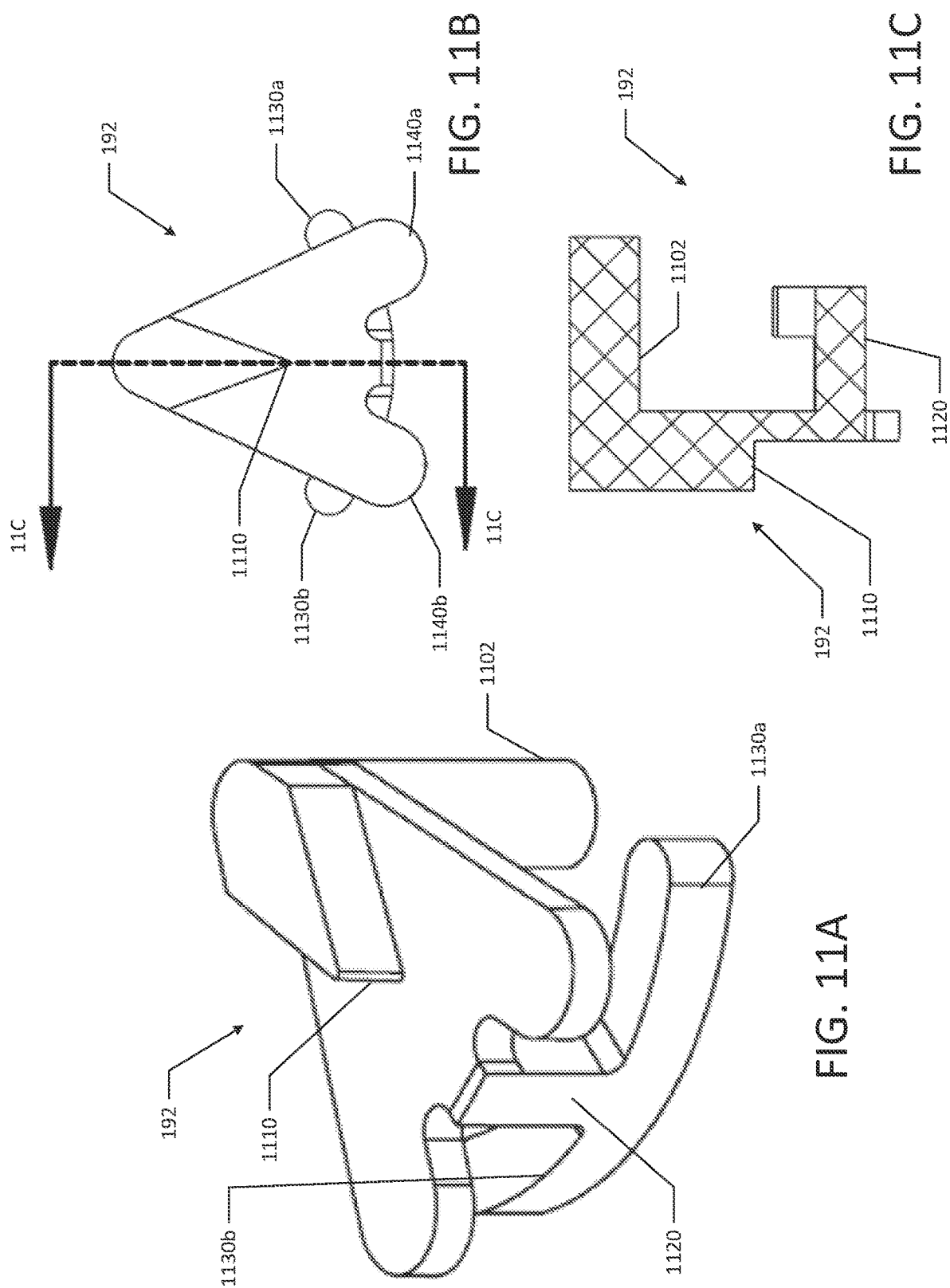

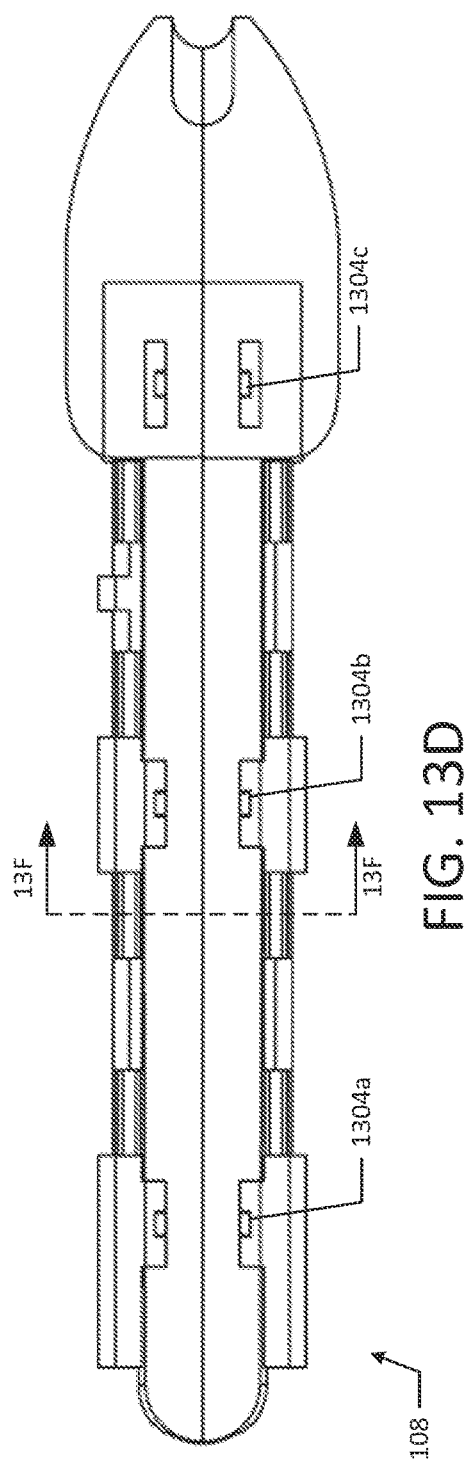
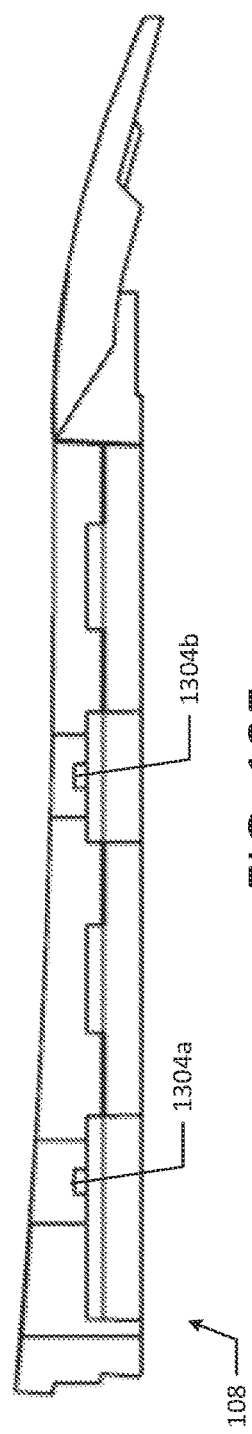
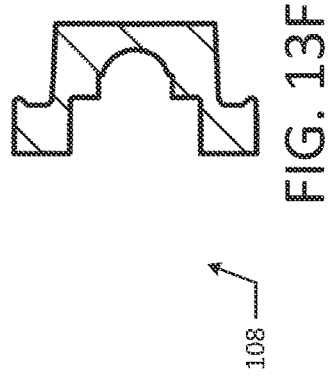
FIG. 13D
FIG. 13E
FIG. 13F

SURGICAL CLIP APPLICATION DEVICE

CROSS-REFERENCE TO RELATED APPLICATIONS

The present application claims priority to U.S. Patent Application No. 63/241,288, filed on Sep. 7, 2021, the disclosure of which is incorporated herein by reference for all purposes.

BACKGROUND

Clip application devices or clip appliers may be used during microsurgery procedures. Microsurgery covers a variety of procedures using a microscope for operating on successively smaller blood vessels, nerves, etc. Conventional suturing techniques in microsurgery have given way to the use of surgical clips, which are applied at the end of a severed vessel or at a junction of vessels. For example, the surgical clips hold or close the tissue in a similar fashion as conventional sutures. The clips used in microsurgery are very small and are typically called microclips. An example microclip may have a size on the order of 2 mm high and 2 mm wide.

Microclips are commonly applied in surgery by forceps that load and use a single clip at a time. Single load-and-use devices are burdensome to medical professionals, as several clips may be required for a surgical procedure. The numerous reloading actions may cause handling accidents (e.g., dropping a clip on the floor, dropping an instrument, dropping a closed or partially closed clip into a wound), misloaded clips, etc. Additionally, using several sets of forceps requires cleaning and otherwise maintaining a stock of several forceps.

The present invention is directed to a surgical microclip applier for use in microsurgery that provides significant advantages over prior art instruments of the type described above.

SUMMARY

The present disclosure provides a surgical clip application device or clip applier for applying surgical clips to ligate vessels during surgery. The clip applier disclosed herein may automatically load clips, which allows a user to ligate multiple vessels during surgery. As a user aligns a vessel within the jaws of the device and squeezes the device handle, a surgical clip is crimped to ligate the vessel aligned within the jaws. Once the handle is released, another clip is automatically loaded and ready for ligating another vessel.

In an example, a surgical clip applying device includes an enclosure formed from a top housing, a bottom housing and a window cover. The clip applying device also includes a pair of handles including a left handle and a right handle, a main rail supporting a jaw closer, and a pair of clip applying jaws fixedly attached to the bottom housing and retained within the main rail. The pair of clip applying jaws has arms terminating with a pair of jaw heads. Additionally, the clip applying device includes a clip loader assembly with a clip loading tip at the clip loader assembly's distal end and a dispenser positioned above the clip loader assembly. The dispenser includes a pair of clip forks and a retention prong positioned between the pair of clip forks at the dispenser's distal end. The clip loading tip is configured to push a surgical clip supported by the pair of clip forks over the retention prong. The clip applying device also includes a clip pusher assembly configured to advance a plurality of clips towards the pair of jaw heads and a drive mechanism including a plurality of levers and at least one spring. The drive mechanism is configured to translate an actuation of the pair of handles to linear motion of the jaw closer and the clip loader assembly.

The surgical clip application device or clip applier disclosed herein is expected to offer convenience compared to devices and systems that require manually loading individual clips.

It is another advantage of the present disclosure to provide a surgical clip application device (e.g., clip applier) with automatic surgical clip reloading.

Additionally, another advantage of the present disclosure is to provide a surgical clip application device (e.g., clip applier) with a transparent window thereby allowing a user to easily ascertain a remaining clip count for surgical clips housed within the device.

It is a further advantage of the present disclosure to provide a surgical clip application device (e.g., clip applier) with multiple touch points, finger loops, and gripping surfaces for ambidextrous surgical clip application.

Additional features and advantages of the disclosed surgical clip application device (e.g., clip applier), systems, and methods are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein. Moreover, it should be noted that the language used in the specification has been principally selected for readability and instructional purposes, and not to limit the scope of the inventive subject matter.

BRIEF DESCRIPTION OF THE FIGURES

FIGS. 1F, 1G, 1H, 1I, 1J, and 1K illustrate another alternate embodiment of an example clip application device according to the present disclosure.

FIGS. 3A, 3B and 3C illustrate an example top housing according to the present disclosure.

FIGS. 3D and 3E illustrate another example top housing according to the present disclosure.

FIGS. 5A, 5B, 5C, 5D and 5E illustrate an example main rail according to the present disclosure.

FIGS. 6A, 6B and 6C illustrate an example jaw closer according to the present disclosure.

FIGS. 7E and 7F illustrate another example pair of clip applying jaws according to the present disclosure.

FIGS. 8B, 8C, 8D and 8E illustrate an example proximal clip loader according to the present disclosure.

FIGS. 8F, 8G, 8H and 8J illustrate an example distal clip loader according to the present disclosure.

FIGS. 8K, 8L and 8M illustrate another example clip loader assembly according to the present disclosure.

FIGS. 8N, 8P and 8Q illustrate another example proximal clip loader according to the present disclosure.

FIGS. 9F, 9G, 9H and 9I illustrate another example dispenser according to the present disclosure.

FIGS. 9J, 9K, 9L, 9M, and 9N illustrate yet another example dispenser according to the present disclosure.

FIGS. 11A, 11B, 11C, 11D and 11E illustrate an example ratchet pawl according to the present disclosure.

FIGS. 13D, 13E, and 13F illustrate another example window cover of the present disclosure.

DETAILED DESCRIPTION OF EXAMPLE EMBODIMENTS

The surgical clip application device (e.g., clip applier) for ligating vessels described herein provides improved surgical clip application, automatic surgical clip reloading, and safety lock-out features.

Figure 1A:
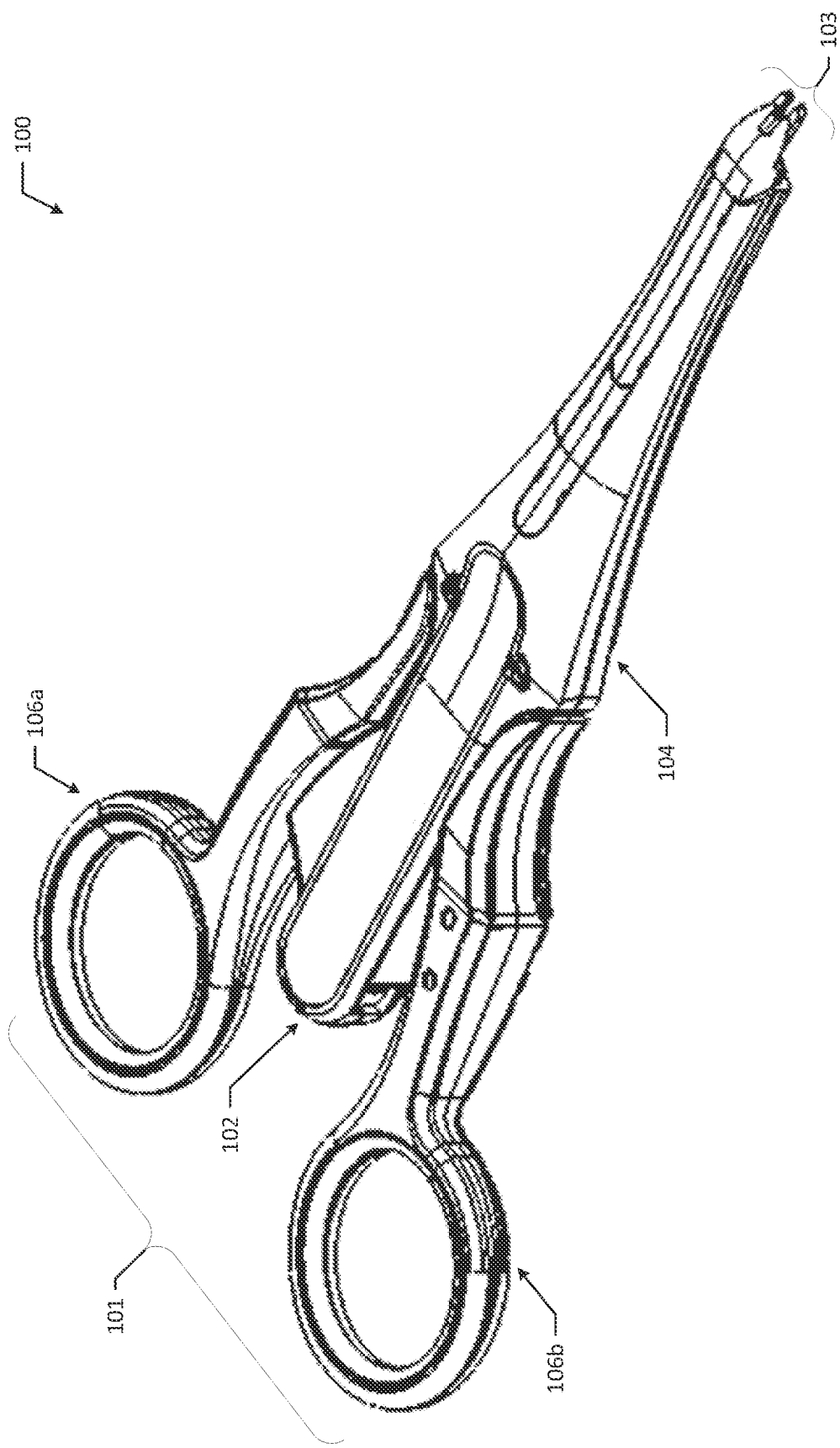
FIG. 1A is a perspective view an example clip application device according to the present disclosure.
Figure 1B:
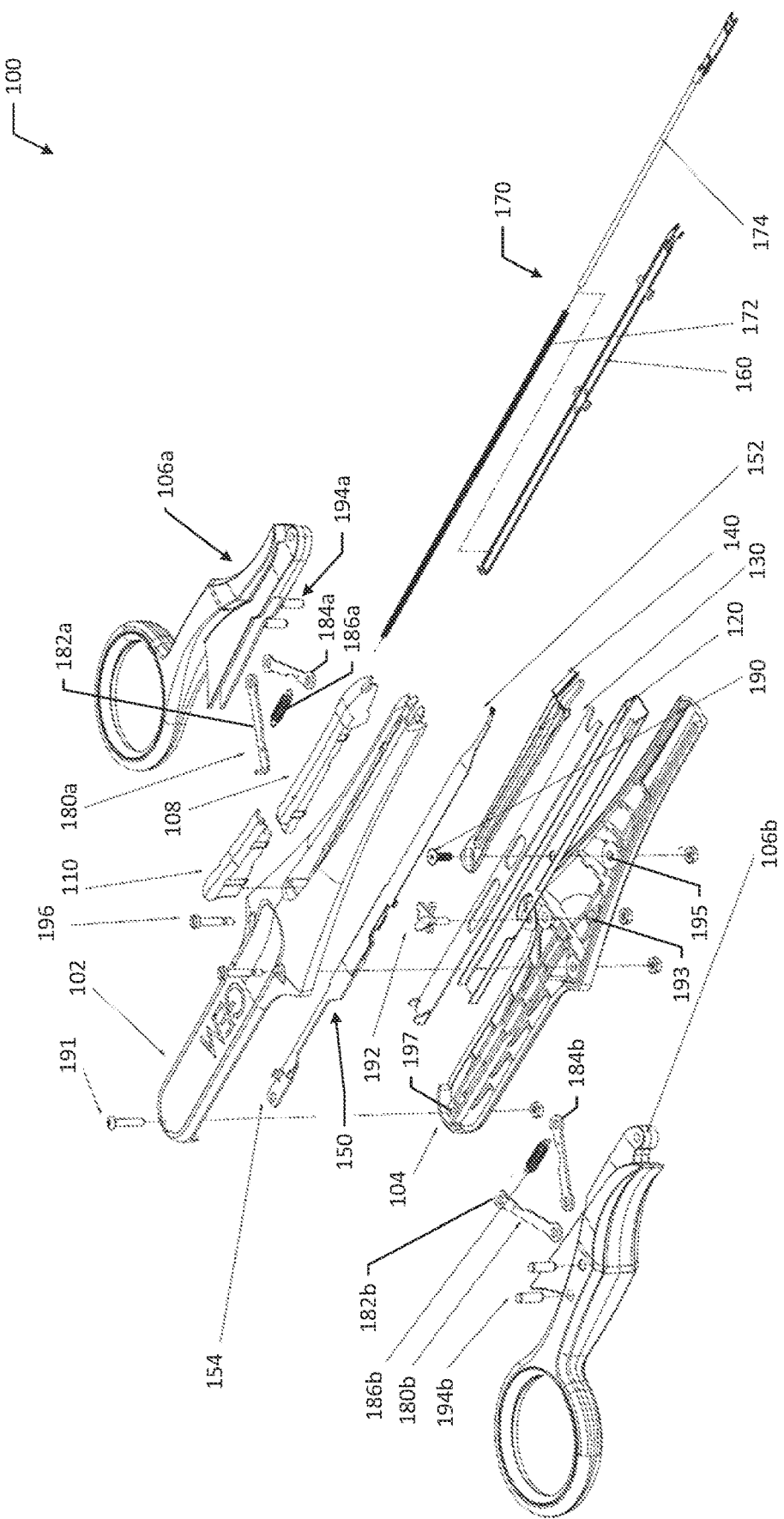
FIG. 1B is an exploded perspective view of the example clip application device of FIG. 1A.

FIGS. 1A and 1B illustrate an example embodiment of a clip applier 100. The clip applier 100 is configured to apply clips to a surgical site. The clip applier 100 includes a top housing 102, a bottom housing 104, a left handle 106a, and a right handle 106b that together form an enclosure for the clip applier 100. Each of the left handle 106a and right handle 106b, hereinafter referred to generally as handles 106, are pivotally mounted in relation to the rest of the enclosure. The enclosure for the clip applier 100 may be secured together by fasteners or other attachment means. Each of the top housing 102, bottom housing 104, left handle 106a and right handle 106b may be fabricated from molded plastic. As illustrated in FIG. 1A, the clip applier 100 has a proximal end 101 and a distal end 103 (e.g., clip applying end). Specifically, the distal end 103 corresponds to the portion of the clip applier 100 where clips are crimped and applied.

The handles 106 cooperate to impart linear reciprocating movement to the clip applying components housed within the enclosure. In an example, the handles 106 are biased to an open position. As illustrated in FIGS. 1A and 1B, the handles 106 include looped bodies with finger rings, similar to a pair of scissors. In another example, the handles 106 may instead include loop-less bodies, similar to a pair of pliers. In either case, the finger rings of the looped bodies or the corresponding gripping surfaces of the loop-less bodies may be made from or over-molded with a rubber-like material to improve grip and comfort.

A window cover 108 and a trough 110 sit atop the top housing 102. The enclosure of the clip applier 100 houses a main rail 120, a jaw closer 130, clip applying jaws 140, and a clip loader assembly 150 that includes a proximal clip loader 154 and a distal clip loader 152. The clip loader assembly 150 cooperates with handles 106 and various other internal components, such that the distal clip loader 152 moves in a linear reciprocating motion for loading clips into the clip applying jaws 140.

The enclosure of the clip applier 100 also houses a dispenser 160 and a clip pusher assembly 170. The clip pusher assembly 170 includes a clip pusher spring 172 and a clip pusher bar 174. Additionally, the clip applier 100 includes a right lever assembly 180a and a left lever assembly 180b. The right lever assembly 180a includes a proximal lever 182a, a distal lever 184a and a spring 186a. The left lever assembly 180b includes a proximal lever 182b, a distal lever 184b and a spring 186b.

As discussed in more detail below, right lever assembly 180a and left lever assembly 180b, hereinafter referred to generally as lever assemblies 180, move in conjunction with actuation of handles 106 to control the motion of the jaw closer 130 and the clip loader assembly 150. In the open position, the proximal levers 182 and the distal levers 184 are nearly parallel with each other (see FIG. 1D) with the clip loader assembly 150 fully advanced. When the handles are transitioned from the open position to the closed position, the proximal levers 182 and the distal levers 184 create a diamond shape, pulling the clip loader assembly 150 back to a retracted position to grab the next surgical clip. Additionally, when the handles are transitioned from the open position to the closed position, the distal levers 184 push the jaw closer 130 forward to close the jaw heads and crimp the surgical clip that was advanced to the end of the clip applying jaws 140. As the handles are again transitioned from the closed position to the open position, the jaw closer 130 retreats to a fully retracted position.

A jaw anchor 190, such as a pin or screw (e.g., flat head cap screw) couples the clip applying jaws 140 to the jaw closer 130 and the main rail 120. Additionally, the anchor 190 fixes the clip applying jaws 140 and the main rail 120 to the bottom housing 104. As discussed in more detail below, the anchor 190 limits the range of motion of the jaw closer 130. In another example, the jaw anchor 190 may instead be a post that is molded as part of the bottom housing 104. As illustrated in FIG. 1B, the jaw anchor 190 is received in a corresponding slot 195 in the lower housing 104.

A handle anchor 191, such as a pin or screw (e.g., button head cap screw) couples the top housing 102 to the bottom housing 104 near the proximal end of the clip applier 100. As illustrated in FIG. 1B, the handle anchor 191 is received in a corresponding slot 197 in the lower housing 104.

The clip applier 100 also includes a ratchet pawl 192 that serves as an anti-backup mechanism that cooperates with the other clip handling components housed within the enclosure for the clip applier 100. As illustrated in FIG. 1B, the ratchet pawl 192 cooperates with the proximal clip loader 154, such that the proximal clip loader 154 moves in a linear reciprocating motion. The ratchet pawl 192 includes a pawl pin that is positioned through corresponding openings in the jaw closer 130 and the main rail 120 before being received in a corresponding slot 193 in the lower housing 104.

The clip applier 100 may also include various attachment mechanisms, such as a set of right side pins 194a and a set of left side pins 194b that fixedly attach one end of the levers to their corresponding handle. For example, the set of pins 194a fixedly attach one end of each of the proximal lever 182a and the distal lever 184a to the left handle 106a. Similarly, the set of pins 194b fixedly attach one end of each of the proximal lever 182b and the distal lever 184b to the right handle 106b. The clip applier 100 may also include a set of screws 196 that connect the top housing 102 to the bottom housing 104. The pins 194a, 194b (hereinafter generally referred to as pins 193) and the screws 196 are example attachment mechanisms illustrated in FIG. 1B. It should be appreciated that the clip applier 100 may include various other attachment means, including other types of fasteners, press-fit connections, adhesives, welding (e.g., electronic welding), etc.

Figure 1C:
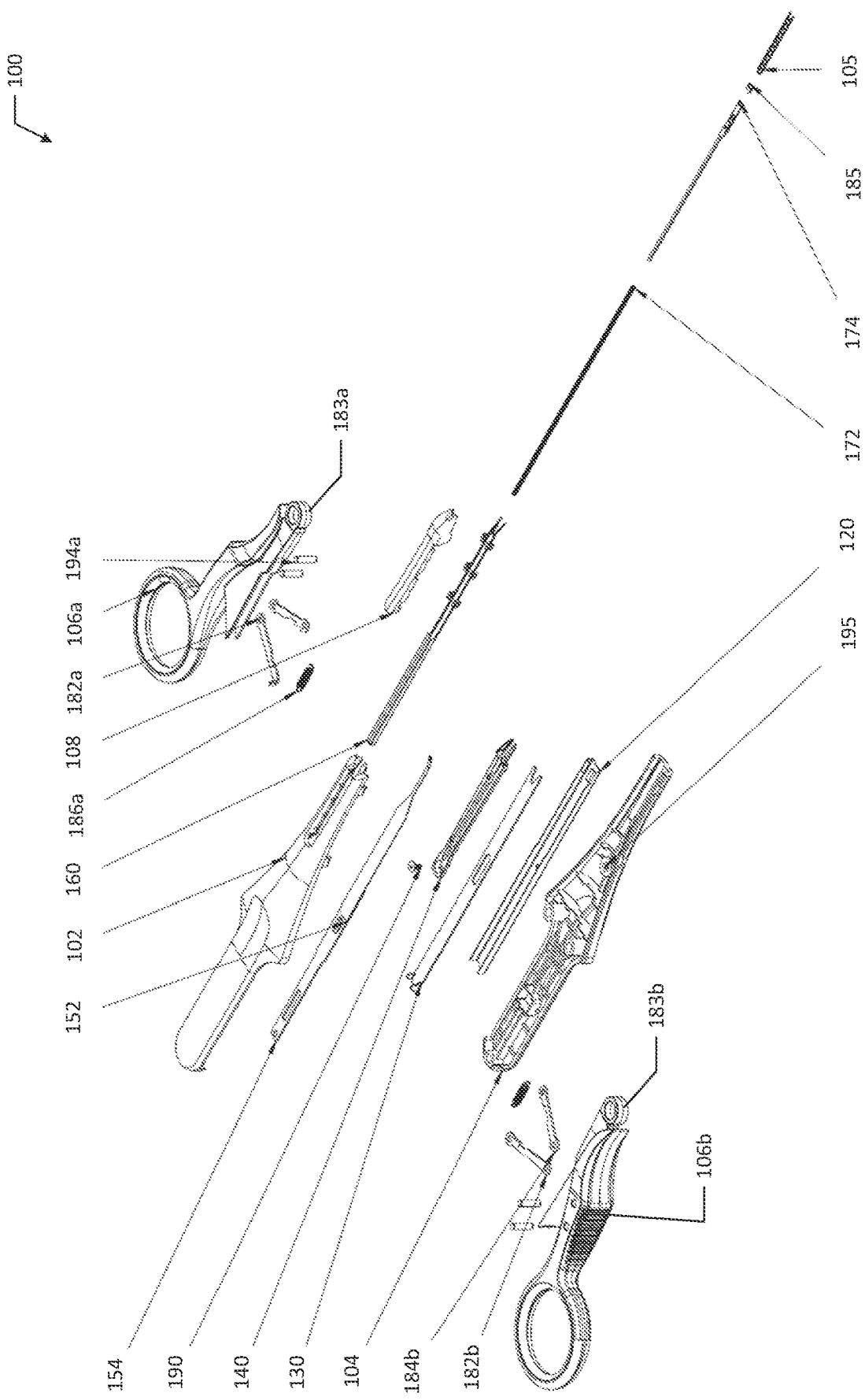
FIG. 1C is an exploded perspective view of an alternate embodiment of an example clip application device according to the present disclosure.

FIG. 1C illustrates another example embodiment of a clip applier 100. Many of the components illustrated in FIG. 1C may be the same or have similar features to the components illustrated in FIG. 1B. In the illustrated example, the alternate embodiment includes variations of the main rail 120, jaw closer 130, clip applying jaws 140, clip loader assembly 150 (e.g., distal clip loader 152 and proximal clip loader 154), dispenser 160, etc. These variations are described in more detail and illustrated in some of the following component diagrams. The exploded view illustrated in FIG. 1C also shows a stack 105 of surgical clips (not pictured in FIG. 1B). Furthermore, the alternate embodiment of the clip applier 100 shown in FIG. 1C also includes a lock-out clip 185.

Figure 1D:
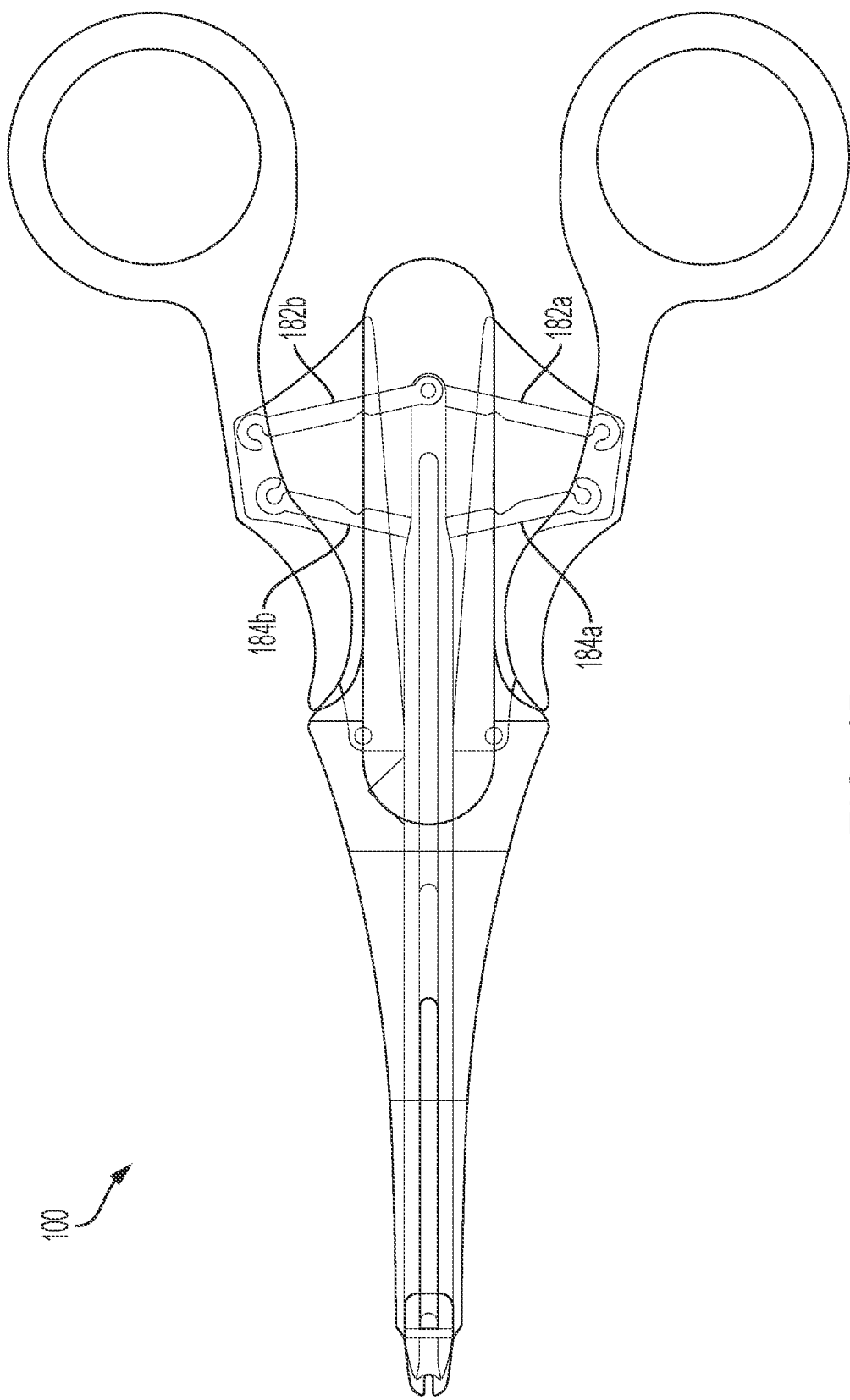
FIG. 1D illustrates an example clip application device in an open configuration according to the present disclosure.
Figure 1E:
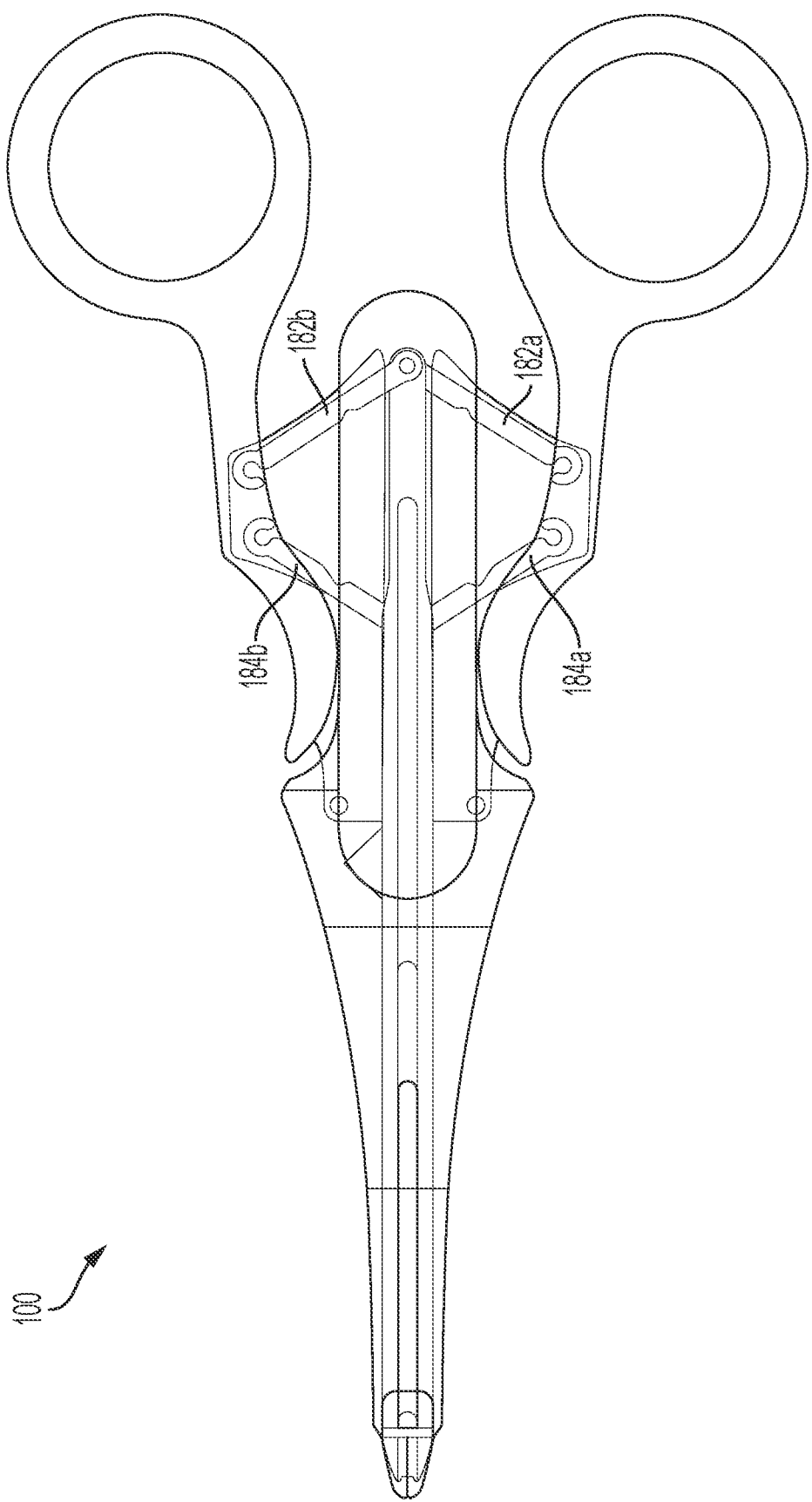
FIG. 1E illustrates an example clip application device in a closed configuration according to the present disclosure.

FIG. 1D illustrates the clip applier 100 in the open position and FIG. 1E illustrates the clip applier 100 in the closed position.

FIGS. 1F, 1G, 1H, 1I, 1J, and 1K illustrate yet another example embodiment of a clip applier 100. Some of the components of the example embodiment of the clip applier 100 shown in FIGS. 1F-1K may be the same or have similar features as corresponding components illustrated in FIGS. 1B and/or 1C. The alternate embodiment of the clip applier 100 illustrated in FIGS. 1F-1K includes variations of the top housing 102, the bottom housing 104, the window cover 108, the main rail 120, the dispenser 160, and the lock-out clip 185. These variations are described and/or illustrated in more detail in within other illustrative examples of the present disclosure.

Figure 1F:
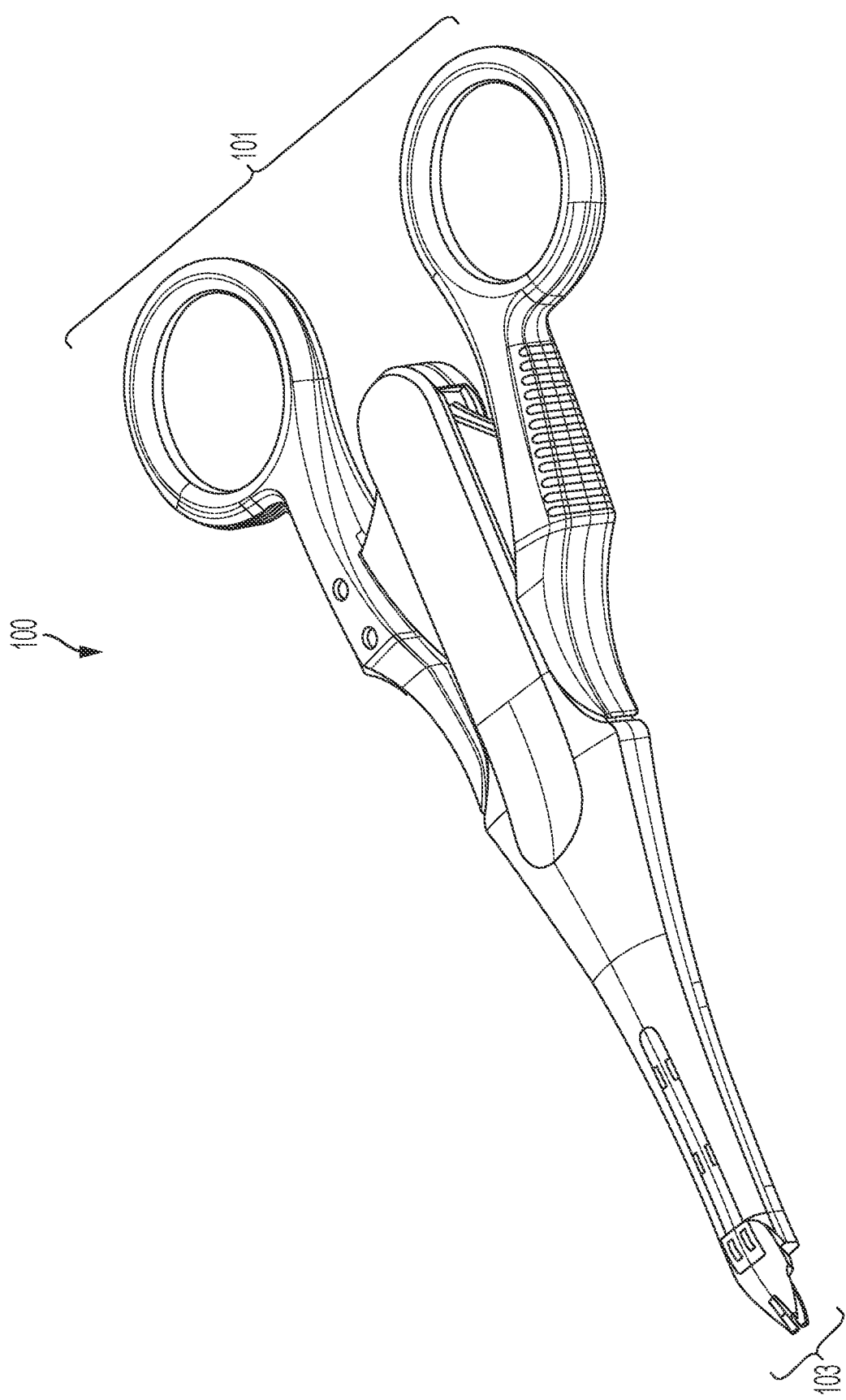
Figure 1G:
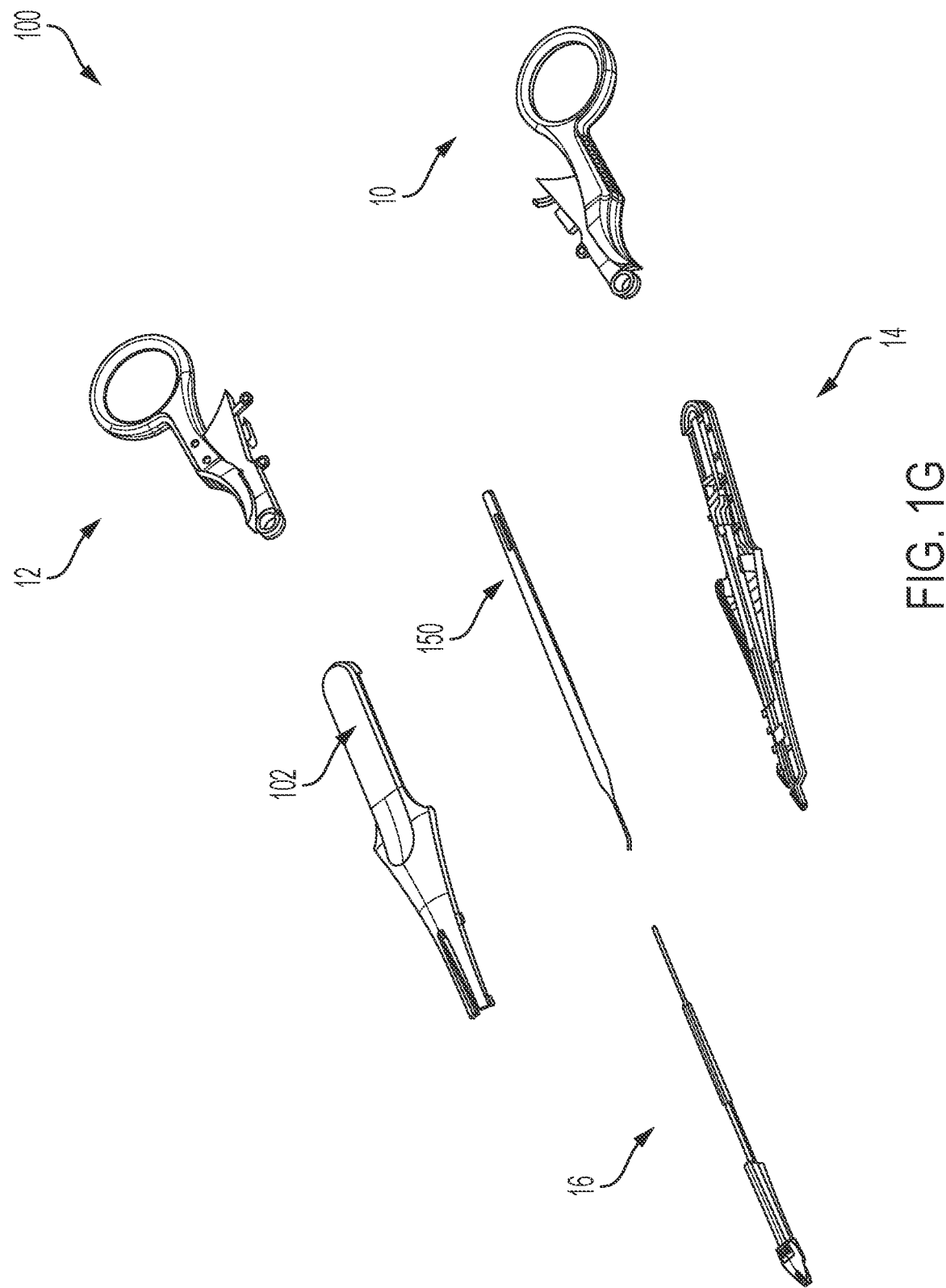

FIG. 1F illustrates a perspective view of an example clip applier 100. FIG. 1G illustrates an exploded view of the example clip applier 100 of FIG. 1F. In the illustrated example of FIG. 1G, the clip applier 100 includes a left handle assembly 10, a right handle assembly 12, a bottom enclosure assembly 14, a clip dispenser assembly 16, the top housing 102, and the clip loader assembly 150. More generally, in some examples, one or more portions of the clip applier 100 are implemented as separate sub-assemblies (e.g., the left handle assembly 10, the right hand assembly 12, the bottom enclosure assembly 14, the clip dispenser assembly 150, etc.), which are then combined to assemble the clip applier 100.

Figure 1I:
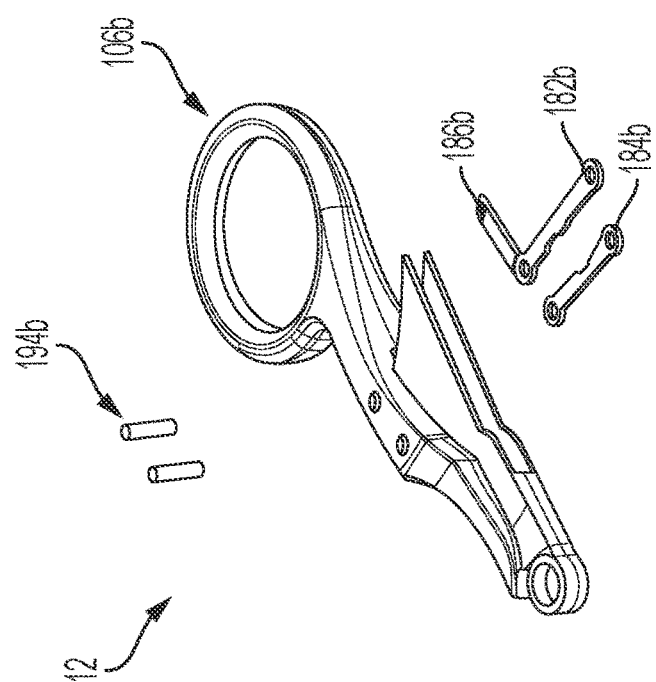
Figure 1H:
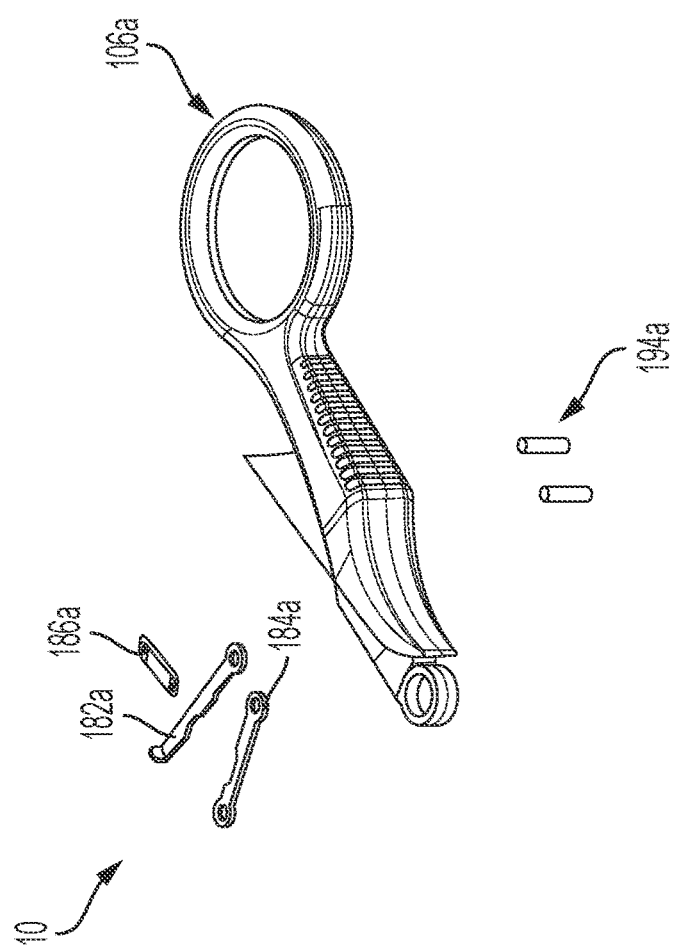

FIG. 1H illustrates an exploded view of the left handle assembly 10. As best shown in FIG. 1H, the left handle assembly 10 includes the left handle 106a, the proximal lever 182a, the distal lever 184a, the spring 186a, and the pins 194a. In some examples, a length of the distal lever 184a (e.g., "short link") is less than a length of the proximal lever 182a (e.g., "long link," "proximal support long link," etc.). In some examples, the left handle assembly 10 can be assembled by sliding the levers 182a and 184a into the left handle 106a, and then pressing the pins 194a through respective holes in the left handle 106a and/or the levers 182a, 184a to attach the levers 182a, 184a to the left handle 106a. Respective ends of the spring 186a can then be connected to the levers 182a and 184a.

FIG. 1I illustrates an exploded view of the right handle assembly 12. As best shown in FIG. 1I, the right handle assembly 12 includes the right handle 106b, the proximal lever 182b, the distal lever 184b, the spring 186b, and the pins 194b. In some examples, a length of the distal lever 184b (e.g., "short link") is less than a length of the proximal lever 182b (e.g., "long link"). In some examples, the right handle assembly 12 can be assembled by sliding the levers 182b and 184b into the right handle 106b, and then pressing the pins 194b through respective holes in the right handle 106b and/or the levers 182b, 184b to attach the levers 182b, 184b to the right handle 106b. The spring 186b can then be connected to the levers 182b and 184b.

FIG. 1J illustrates an exploded view of the bottom enclosure assembly 14. As best shown in FIG. 1J, the bottom enclosure assembly 14 includes an insert 18, the bottom housing 104 (which includes the slot 195), the main rail 120, the jaw closer 130, the clip applying jaws 140, and the jaw anchor 190. The insert 18 may be a threaded insert or any other type of mechanical coupling device received in the slot 195 to facilitate coupling the bottom housing 104 with the jaw anchor 190. The insert 18 can be formed from any suitable material, such as brass, other metal or metal oxide, plastic, or any other material. In some examples, the jaw anchor 190 is implemented as a screw or a flat head screw. In some examples, the bottom enclosure assembly 14 is assembled by inserting (e.g., sliding) the clip applying jaws 140 and the jaw closer 130 into the main rail 120. The main rail 120 can then be placed into the bottom housing 104 while aligning the threaded insert 18 with respective holes in the jaws 140, the jaw closer 130, and the main rail 120. As such, in the illustrated example of FIG. 1J one or more components (i.e., the main rail 120, the jaw closer 130, and the jaws 140) of the bottom enclosure assembly 14 can be attached to the bottom housing 104 (e.g., by coupling or torqueing the screw 190 into the insert 18 and the slot 195). In alternative examples, a different attachment mechanism can be used.

Figure 1K:
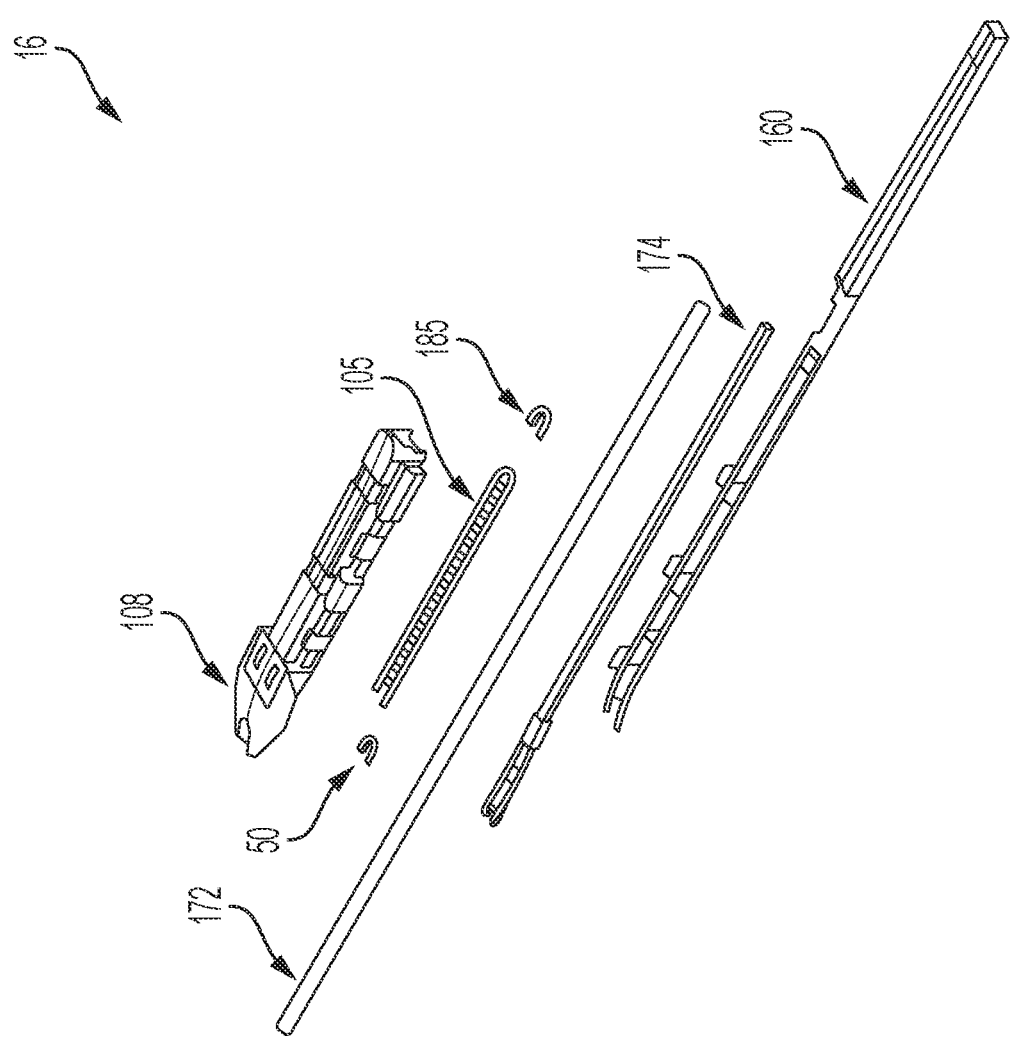

FIG. 1K illustrates an exploded view of the clip dispenser assembly 16. As best shown in FIG. 1K, the clip dispenser assembly 16 includes the stack 105 of surgical clips (exemplified by clip 50), the window cover 108, the dispenser 160, the clip pusher spring 172, the clip pusher bar 174, and the lock-out clip 185. In some examples, the clip dispenser assembly 16 is assembled by connecting the clip pusher spring 172 to the clip pusher bar 174 (e.g., sliding the spring 172 over the pusher bar 174), then connecting the clip pusher bar 174 to the dispenser 160 (e.g., sliding the combination of the bar 174 and the spring 172 into the dispenser 160), then loading the stack 105 of surgical clips and the lockout clip 185 into the dispenser 160, and then attaching the window cover 108 to the dispenser 160. Other attachment mechanisms and/or processes are possible.

As noted above, in some examples, the clip applier 100 can be assembled by coupling the left handle assembly 10, the right handle assembly 12, the bottom enclosure assembly 14, the clip dispenser assembly 16, the top housing 102, and the clip loader assembly 150 to one another. In one specific example, the clip applier 100 of FIGS. 1F-1K is assembled by placing the left handle assembly 10 into the bottom enclosure assembly 14 and securing the distal lever 184a onto the jaw closer 130. The clip loader assembly 150 is then attached by securing a rear hole of the clip loader assembly 150 over the proximal lever 182a. The right handle assembly 12 is then placed into the assembly of the clip applier 100 by similarly securing the distal lever 184b onto the jaw closer 130. The clip dispenser assembly 16 is then placed into the assembly of the clip applier 100 by aligning the window cover 108 with the main rail 120. In this example, the main rail 120 can then be crimped onto the window cover 108. Then, the top housing 102 can be attached by pressing the top housing 102 onto the assembly of the clip applier 100. Other example attachment mechanisms are possible.

Figure 2A:
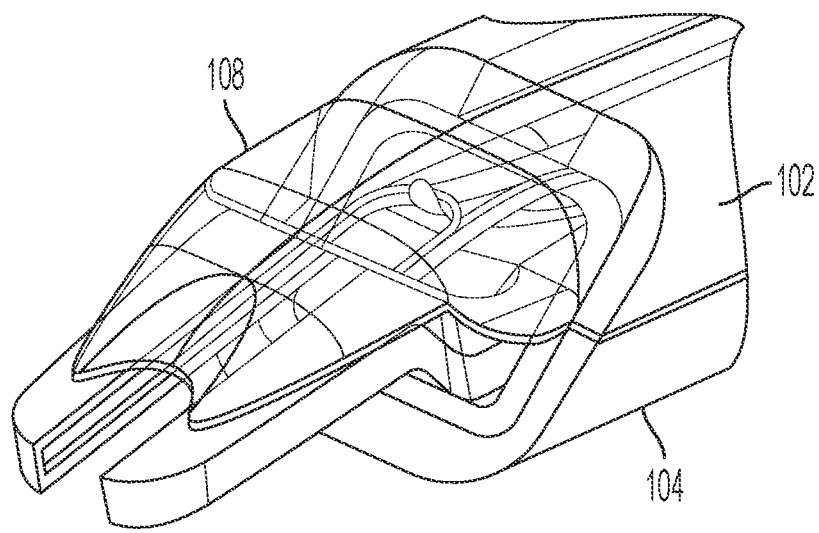
FIGS. 2A, 2B, 2C, 2D, 2E and 2F illustrate a clip advancing to a distal end of the clip application device.
Figure 2B:
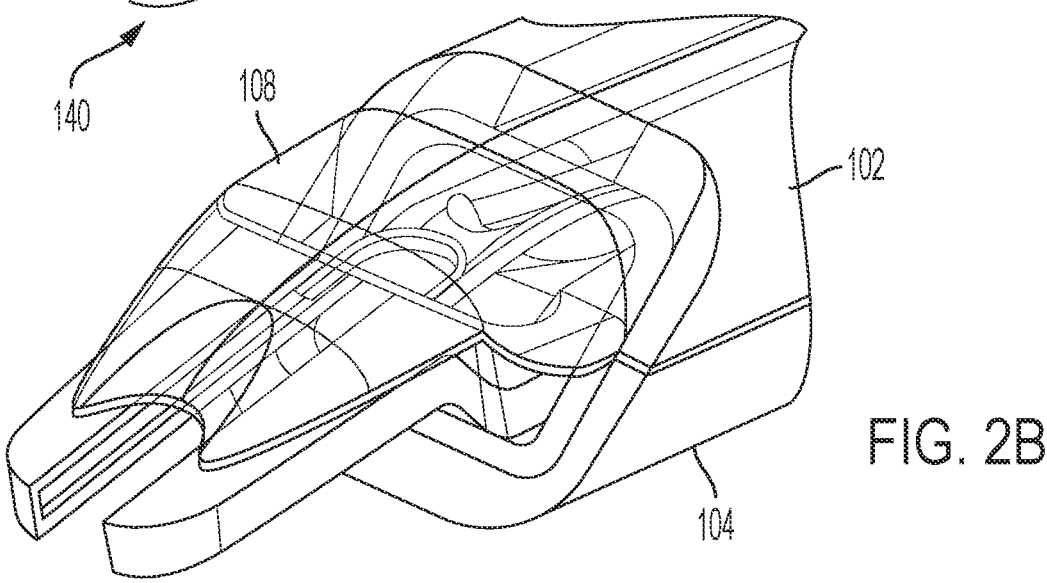
Figure 2C:
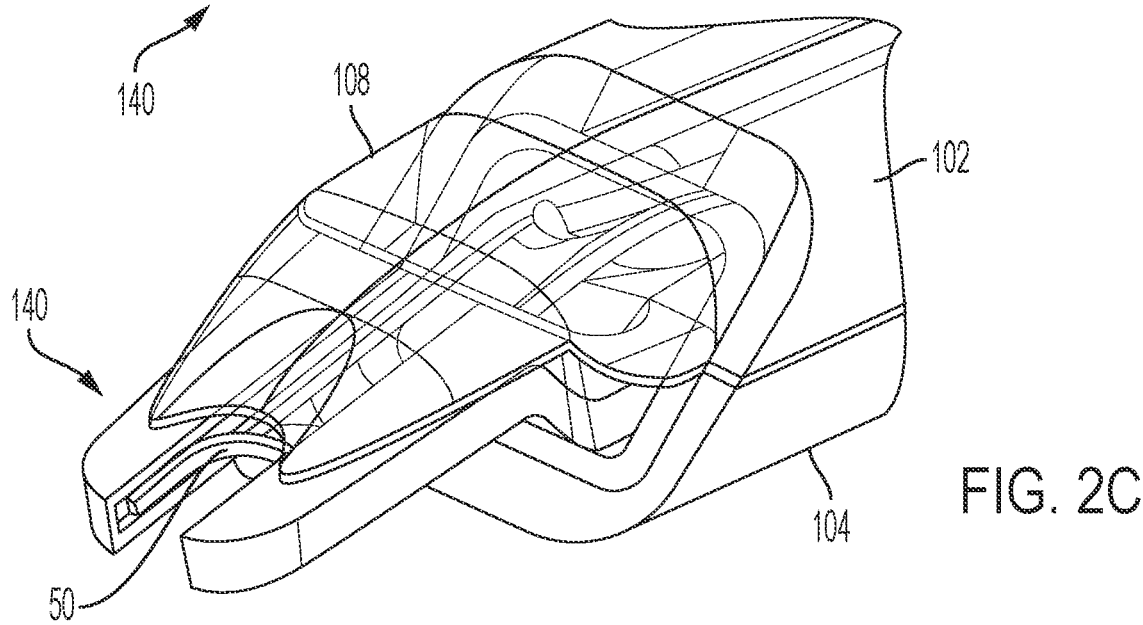
Figure 2D:
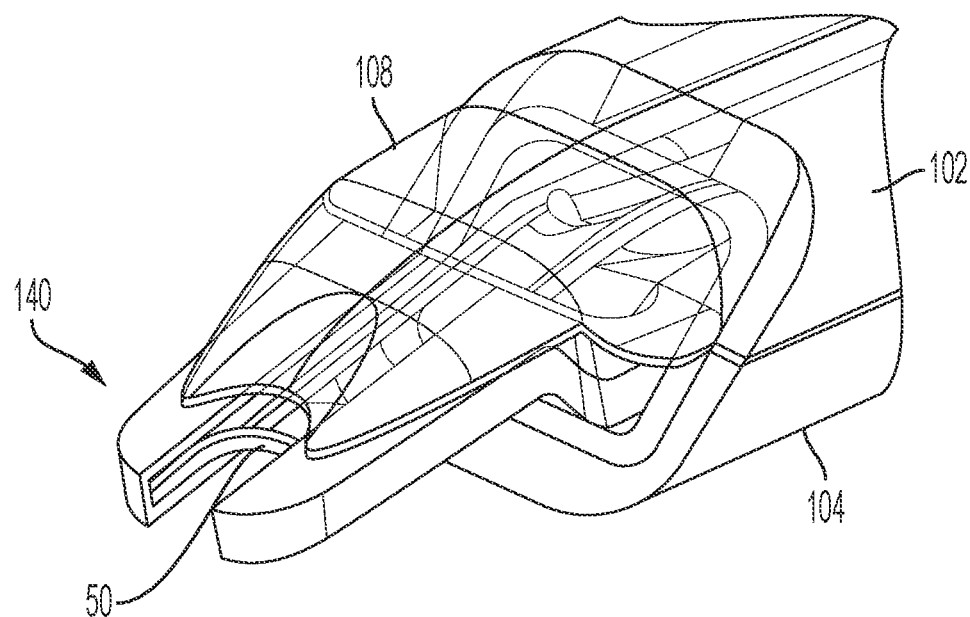
Figure 2E:
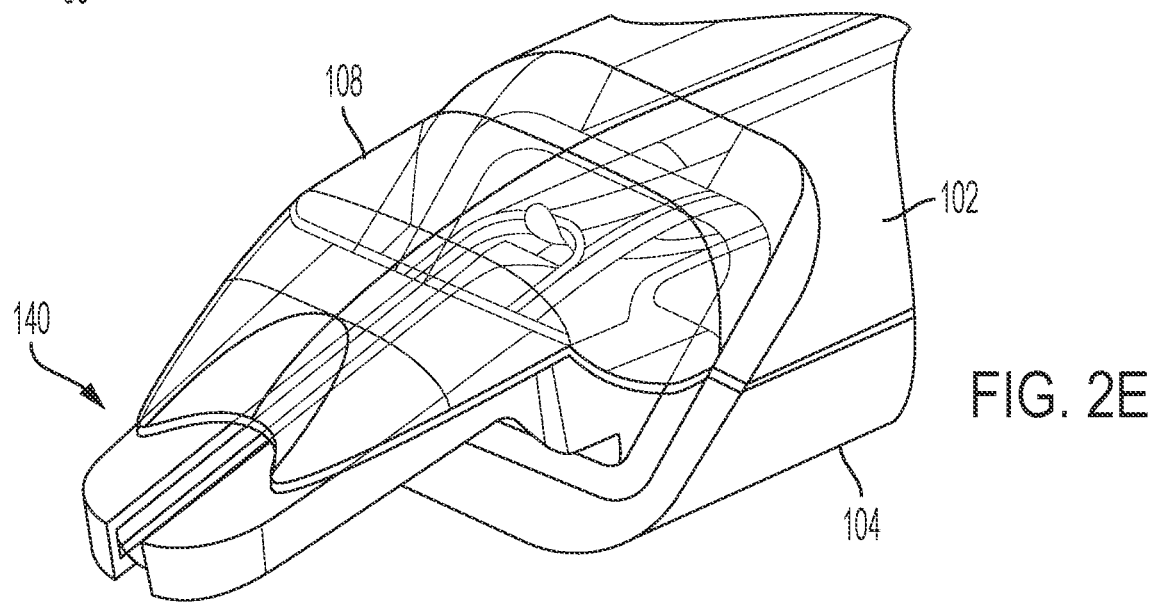
Figure 2F:
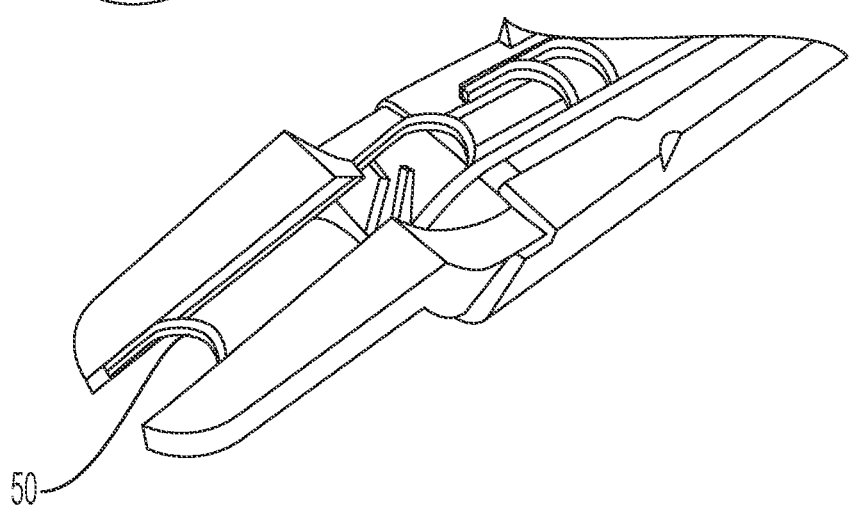

FIGS. 2A, 2B, 2C, 2D, and 2E illustrate the movement of various drive components at the distal end 103 of the clip applier 100 while the device is dispensing and crimping surgical clips, in accordance with at least one example embodiment herein. FIG. 2F illustrates a stack of surgical clips, exemplified by clip 50, which may be provide in a cartridge, at the distal end 103 of the clip applier 100, in accordance with at least one example embodiment herein.

FIGS. 3A, 3B and 3C illustrate top, side and bottom views of the top housing 102.

FIGS. 3D and 3E illustrate another example top housing 102 (e.g., the top housing 102 from FIG. 1C). The top housing 102 may also include handle pegs 187a and 187b that are configured to pass through handle slots (e.g., handle slots 183a and 183b illustrated in FIG. 1C, hereinafter referred to generally as handle slots 183) and couple to corresponding receiving pegs (e.g., receiving pegs 189a and 189b illustrated in FIG. 4E, hereinafter referred to generally as receiving pegs 189). The handle pegs 187a and 187b, hereinafter referred to generally as handle pegs 187, the receiving pegs 189 and the handle slots 183 are configured and arranged such that the left handle 106a and the right handle 106b are capable of pivoting with respect to the enclosure formed by the handles 106, the top housing 102 and the bottom housing 104. In the example illustrated in FIGS. 3D and 3E, the top housing 102 may incorporate a trough portion (e.g., trough 110 of FIGS. 12A to 12E) instead of having a separate trough component.

Figure 3F:
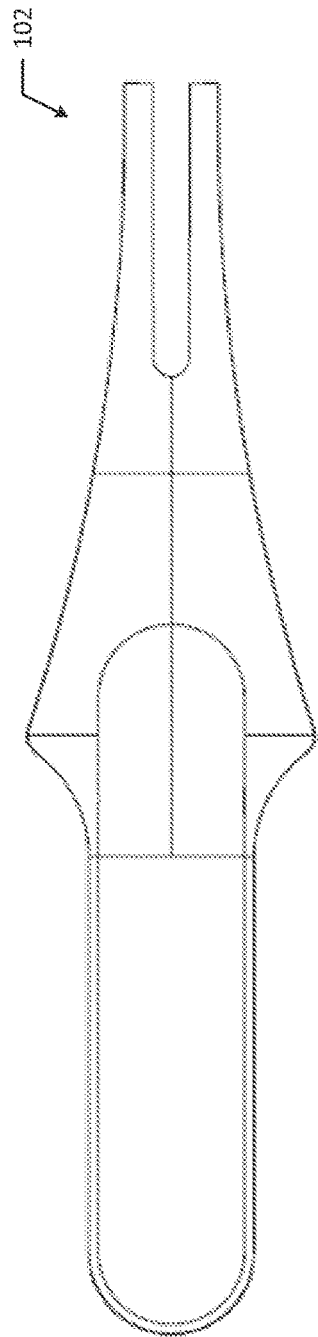
FIGS. 3F, 3G, and 3H illustrate yet another example top housing according to the present disclosure.
Figure 3G:
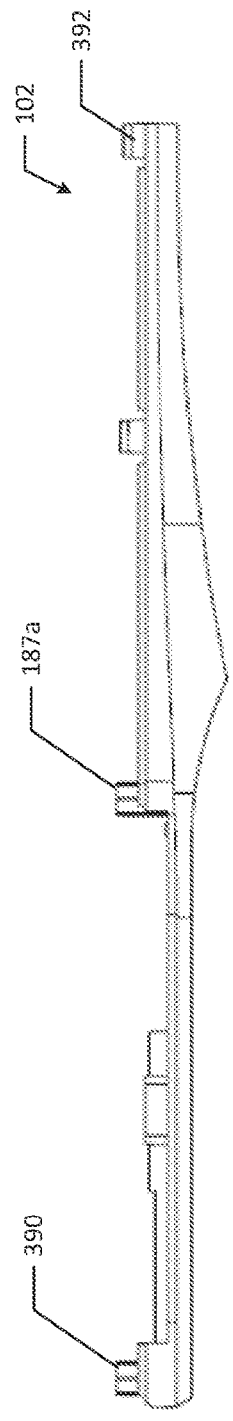
Figure 3H:
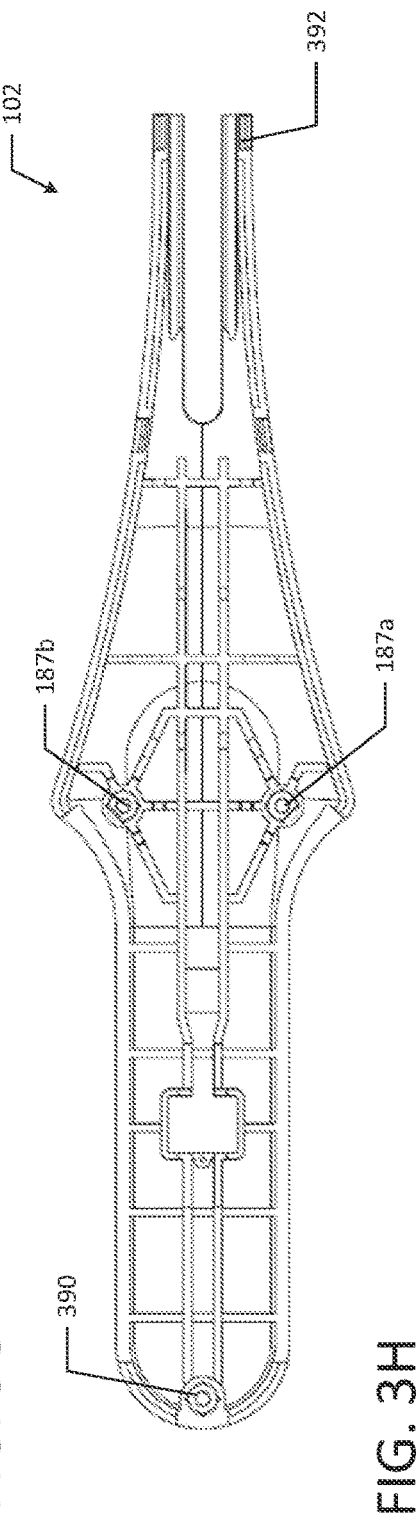

FIGS. 3F, 3G, and 3H illustrate top, side, and bottom views of yet another example top housing 102 (e.g., the top housing 102 of FIG. 1G). As best shown in FIGS. 3G and 3H, the example top housing 102 includes the handle pegs 187a, 187b, an anchor peg 390, and a plurality of tabs exemplified by tab 392. In this example, the top housing 102 can be attached (e.g., pressed, crimped, etc.) to other components of the clip applier 100 by aligning the pegs 187a, 187b, 390, and/or the tabs 392, etc. with corresponding receiving features in the bottom housing 104 and/or in other components of the clip applier 100. For example, the handle pegs 187a and 187b can be received by corresponding receiving pegs (e.g., receiving pegs 189a and 189b illustrated in FIG. 4I), the anchor peg 390 can be received by a corresponding receiving slot (e.g., slot 197 illustrated in FIG. 4I), and the plurality of tabs (exemplified by tab 392) can be aligned and/or received at corresponding recesses (e.g., recesses 492, etc. illustrated in FIG. 4I).

Figure 4A:
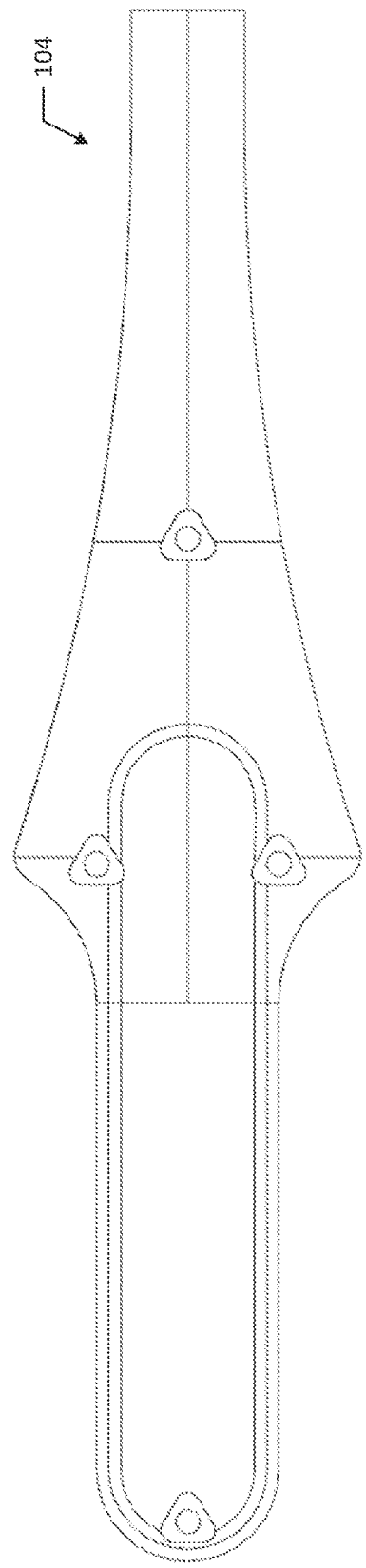
FIGS. 4A, 4B and 4C illustrate an example bottom housing according to the present disclosure.
Figure 4B:
Figure 4C:
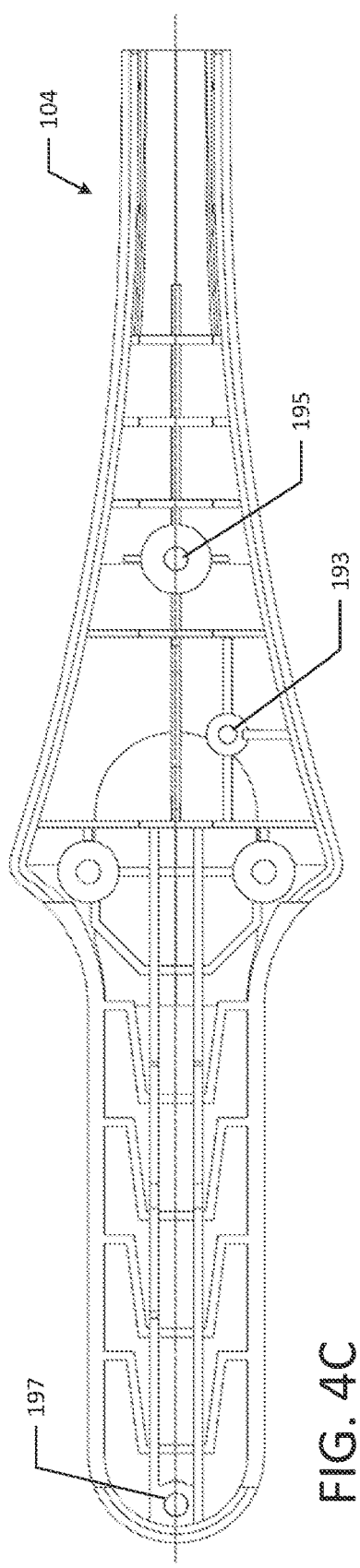
Figure 11D:
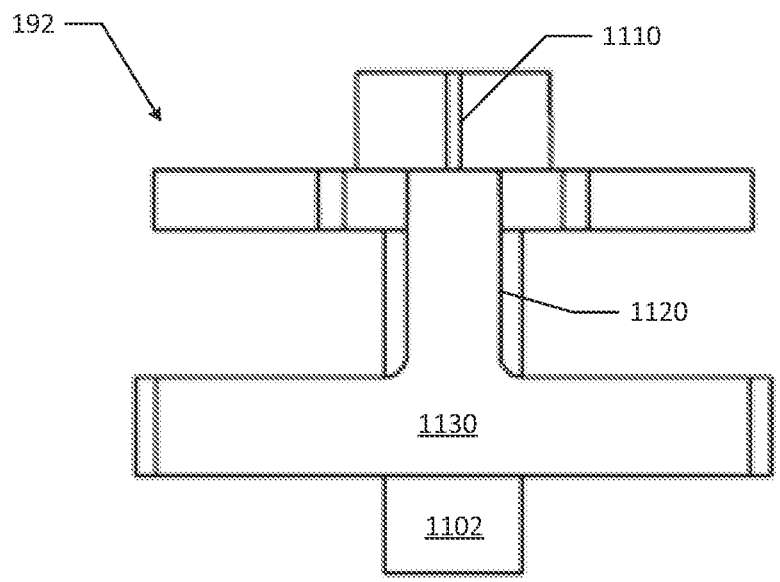

FIGS. 4A, 4B and 4C illustrate top, side and bottom views of the bottom housing 104. As discussed with relation to FIG. 1B, the bottom housing 104 includes slots 193, 195 and 197. Slot 193 is adapted to receive and retain a pawl pin (e.g., pawl pin 1102 of FIG. 11A) of the ratchet pawl 192 after the ratchet pawl pin passes through corresponding openings in the jaw closer 130 and the main rail 120. Slot 195 is adapted to receive and retain the jaw anchor 190 after the jaw anchor 190 passes through corresponding openings in the clip applying jaws 140, the jaw closer 130 and the main rail 120. Slot 197 is adapted to receive and retain the handle anchor 191.

Figure 4D:
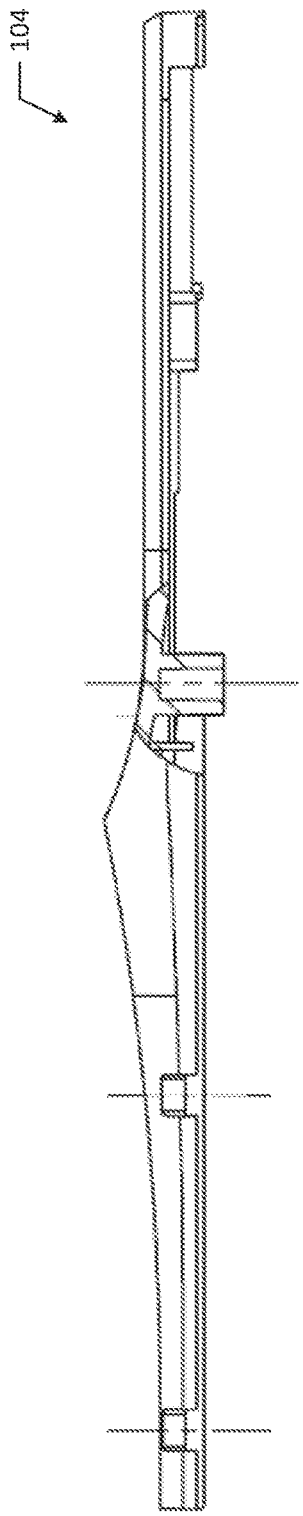
FIGS. 4D, 4E and 4F illustrate another example bottom housing according to the present disclosure.
Figure 4E:
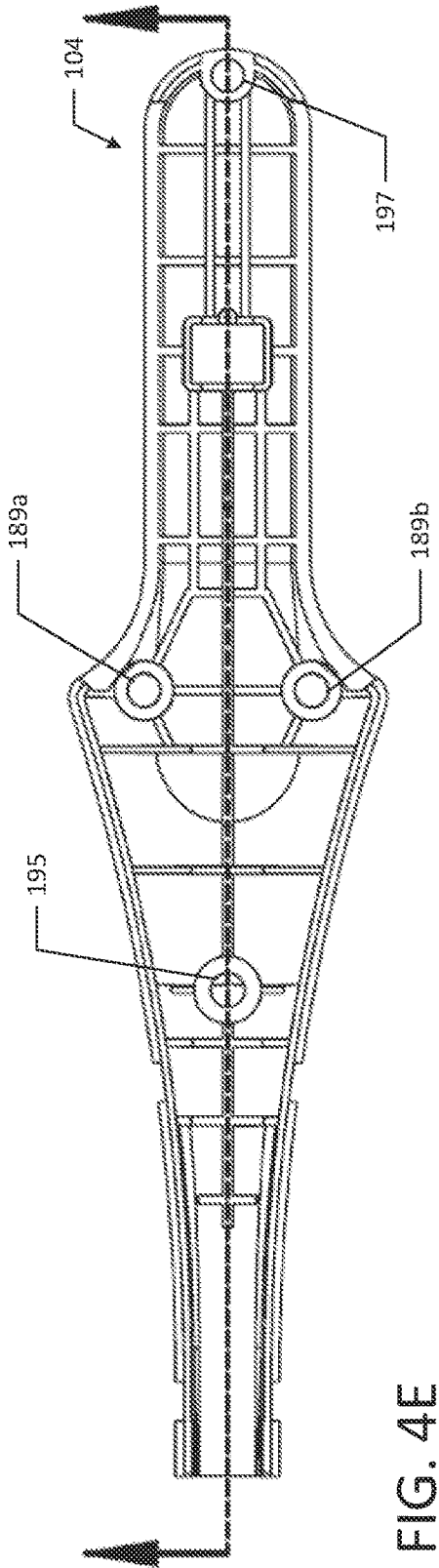
Figure 4F:
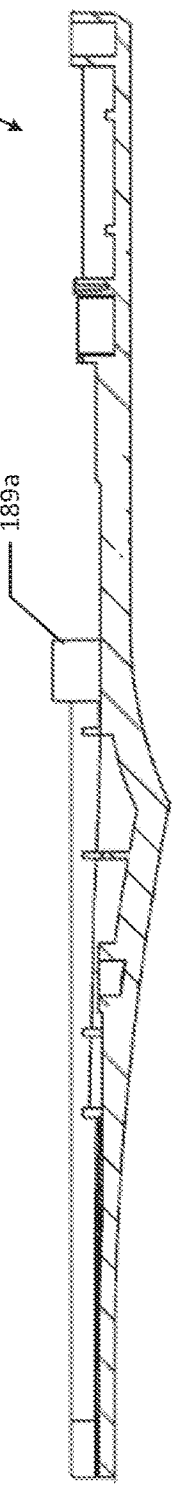

FIGS. 4D, 4E and 4F illustrate another example bottom housing 104, which may include many of the same or similar features as the bottom housing 104 illustrated in FIGS. 4A, 4B and 4C. As mentioned above, the bottom housing 104 may include receiving pegs 189a and 189b. The receiving pegs 189 may be sized and shaped to receive and couple to the corresponding handle pegs 187 of the top housing 102. Specifically, handle slots 183 may be positioned through handle pegs 187 before the handle pegs 187 are positioned within (e.g., press-fit in) receiving pegs 189, which creates a pivot point for handles 106. In an example, the handle pegs 187 and the receiving pegs 189 may be snap-fit gripper pins that form axes of rotation or pivot points for the handles 106. In another example, the handle pegs 187 and the receiving pegs 189 may be dowel pins and bosses. Snap-fit gripper pins may advantageously provide a rotation or pivot point with fewer components.

Figure 4G:
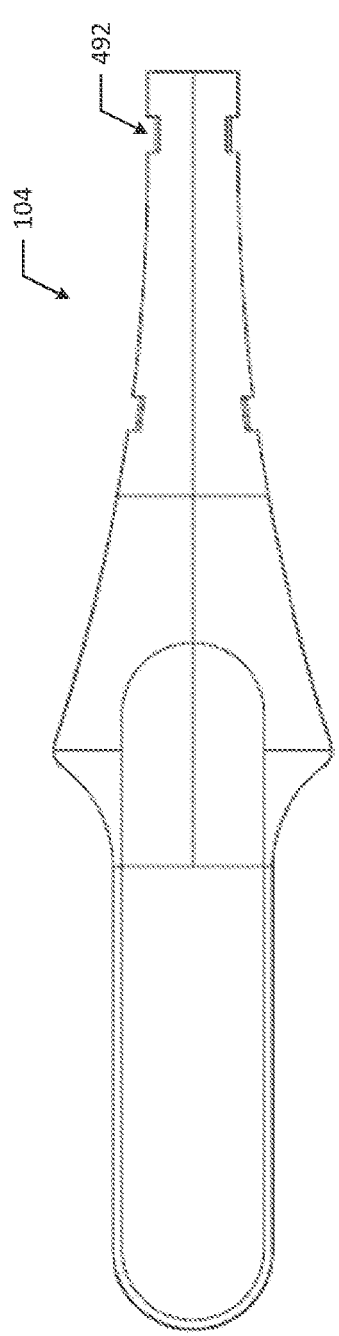
FIGS. 4G, 4H, and 4I illustrate yet another example bottom housing according to the present disclosure.
Figure 4H:
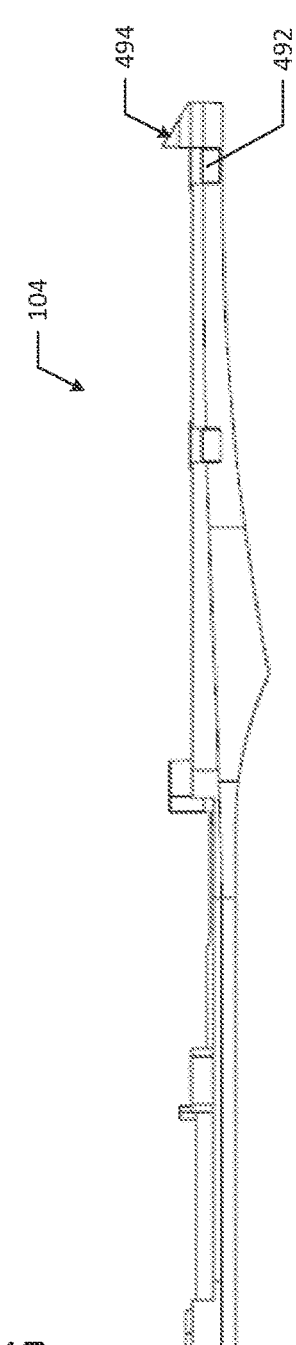
Figure 4I:
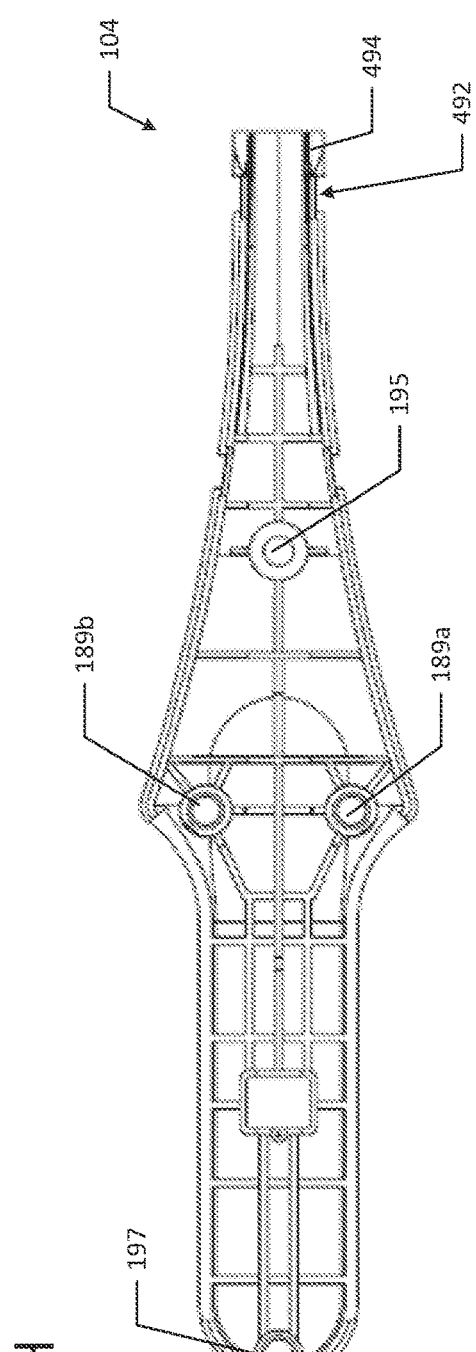

FIGS. 4G, 4H, and 4I illustrate bottom, side, and top views of yet another example bottom housing 104 (e.g., the bottom housing 104 of FIG. 1J). In this illustrated example, the bottom housing 104 includes the receiving pegs 189a, 189b, the slot 195, the slot 197, a plurality of recesses exemplified by tab 492, and a plurality of protruding edges exemplified by edge 494. In this example, the bottom housing 104 can be attached (e.g., pressed, crimped, etc.) to other components of the clip applier 100 by aligning the pegs 189a, 189b, the slot 197, the recesses 492, etc., and/or the edges 494, etc., with corresponding features in the top housing 102 and/or in other components of the clip applier 100. For example, the receive pegs 189a and 189b can receive corresponding handle pegs (e.g., handle pegs 187a and 187b of FIG. 3H), the slot 197 can receive a corresponding anchor peg (e.g., anchor peg 390 of FIG. 3H), and the plurality of recesses (exemplified by tab 492) can be aligned with and/or receive corresponding tabs (e.g., tabs 392, etc. of FIG. 3H). Further, in this example, the edges 494, etc., can be shaped to align and/or receive corresponding edge(s) of the top housing 102 of FIG. 3H.

Figure 5A:
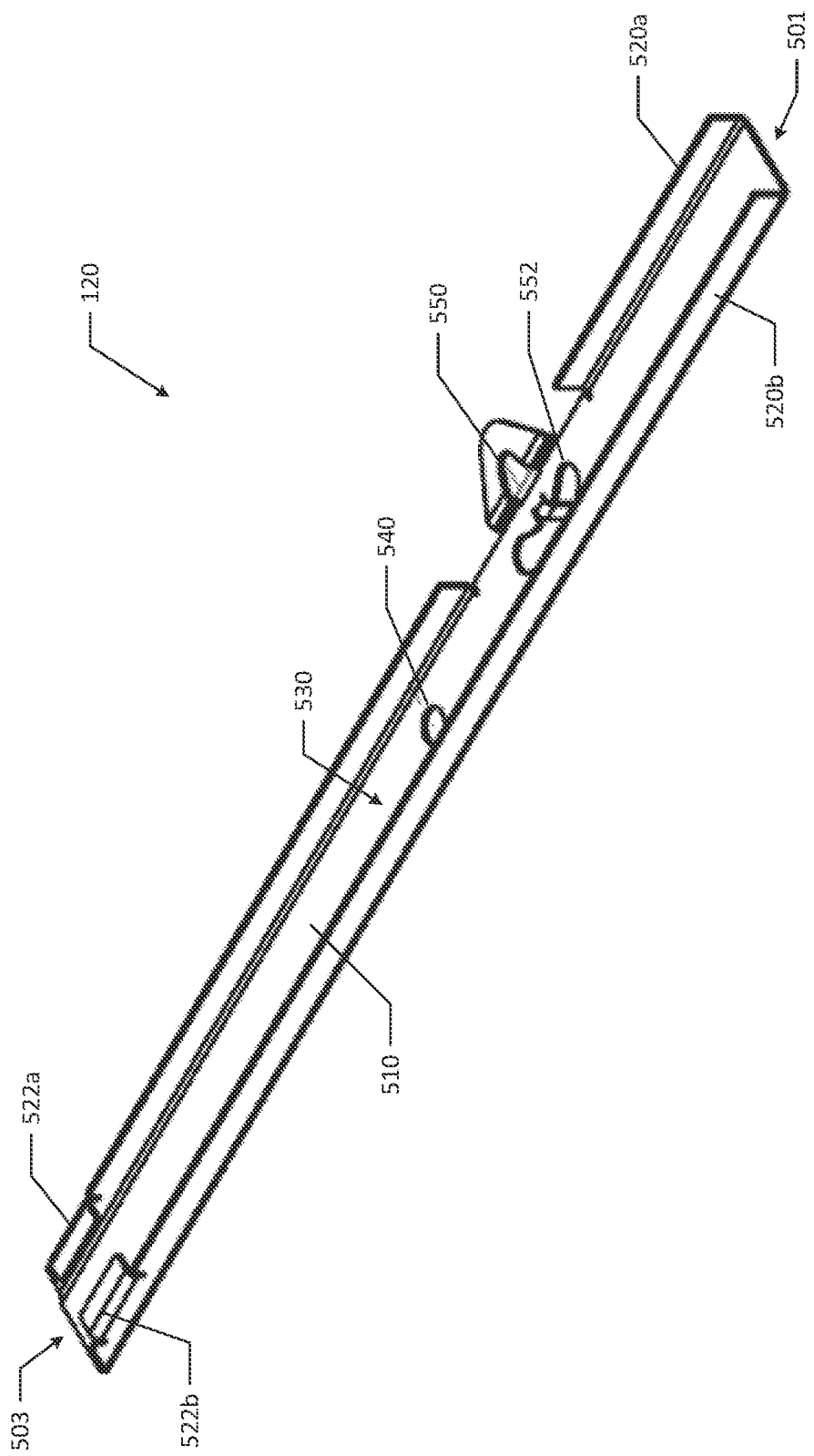

FIGS. 5A, 5B, 5C, 5D and 5E illustrate various views of an example main rail 120. In this example, the main rail 120 includes an elongate base 510 and side walls 520a and 520b that form a channel 530 having a proximal end 501 and a distal end 503. FIG. 5D illustrates a cross-sectional view of the main rail 120 along line A-A of FIG. 5B, which illustrates the channel 530 formed from the base 510 and sidewalls 520a, 520b. Near the distal end 503, the side walls 520a and 520b, hereinafter referred to generally as side walls 520, are folded over forming flanges 522a and 522b. The flanges, which are referred to generally as flanges 522 are adapted to constrain the interaction of the clip applying jaws 140 and the jaw closer 130 thereby preventing the clip applying jaws 140 and the jaw closer 130 from disengaging.

Additionally, in this example, the main rail 120 includes an opening or thru-hole 540 that accommodates jaw anchor 190. Additionally, in this example, the main rail 120 includes an opening or thru-hole 550 that accommodates a pawl pin of the ratchet pawl 192. In this example, the main rail 120 also includes a pawl slot 552 to accommodate a pawl flange (see pawl flange 1130 of FIG. 11E) of the ratchet pawl 192. The pawl slot 552 is sized and shaped to allow the ratchet pawl 192 to pass through the main rail 120 (e.g., flanges 1130a and 1130b of the ratchet pawl 192 of FIG. 11A may pass through slot 552) while the main rail 120 remains fixedly coupled to the bottom housing 104.

The main rail 120 may be fabricated from plastic or metal. In an example, the main rail 120 is fabricated as a stamped piece(s) of metal. As illustrated in the detail view of the example of FIG. 5E, the pawl slot 552 is a curved oval slot or track that allows the ratchet pawl 192 to rotate within the slot 552.

Figure 5F:
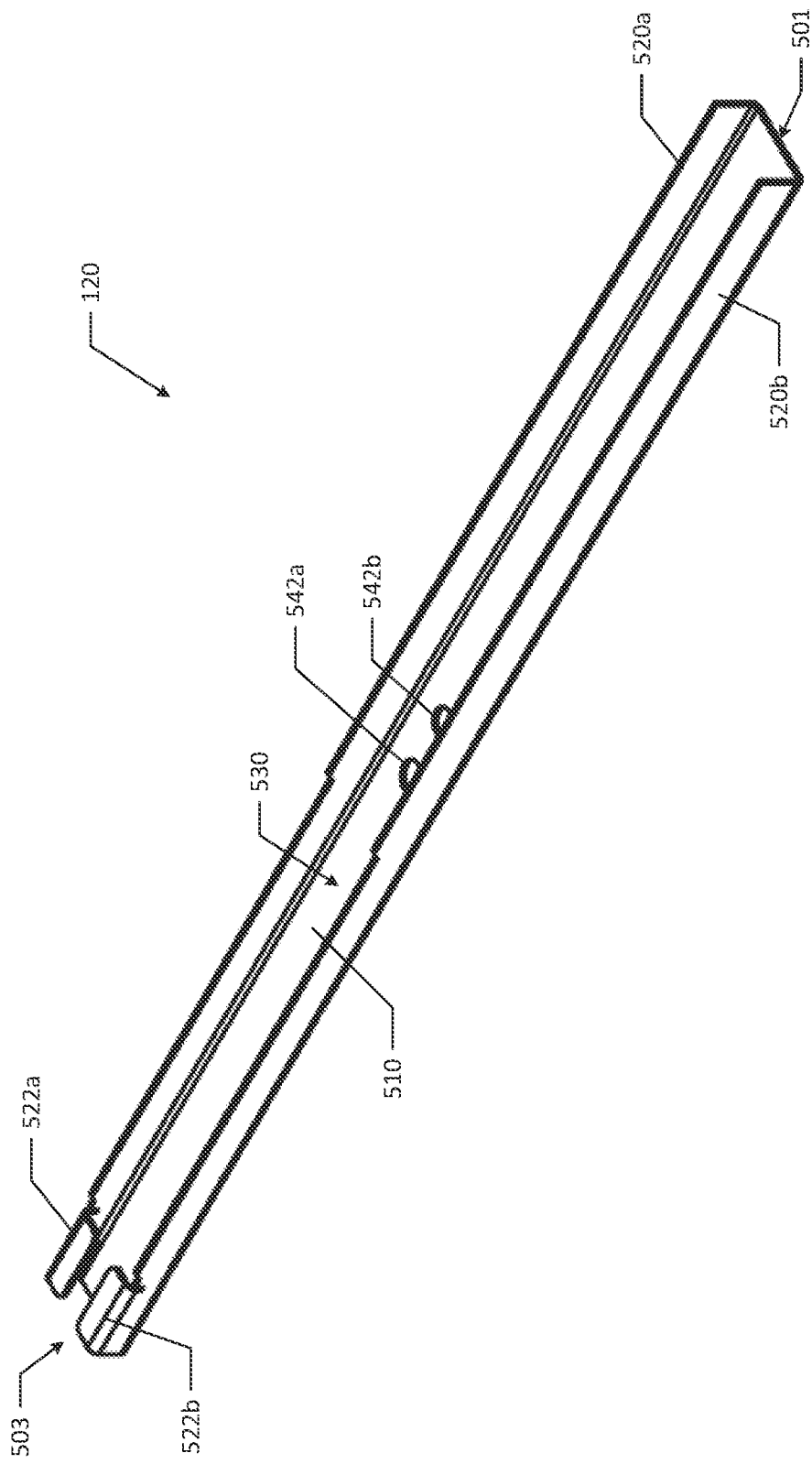
FIG. 5F illustrates another example main rail according to the present disclosure.

FIG. 5F illustrates another example of the main rail 120. Similar to the main rail 120 illustrated in FIGS. 5A-5E, the main rail 120 illustrated in FIG. 5F includes a base 510 and sidewalls 520a and 520b that form channel 530. Additionally, the main rail 120 includes flanges 522a and 522b. Main rail 120 also includes thru-holes 542a and 542b that may be adapted for positioning, alignment and/or securing the main rail 120. Unlike the main rail illustrated in FIGS. 5A-5E, the main rail 120 illustrated in FIG. 5F may be adapted for use without a ratchet pawl 192.

In this example, after the main rail 120 is positioned in the lower housing 102, the jaw closer 130 is positioned within the main rail 120. Specifically, the channel 530 is configured to receive the jaw closer 130, which sits atop the base 510 of the main rail 120. The jaw closer 130 is further described and illustrated in FIGS. 6A, 6B and 6C.

Figure 5G:
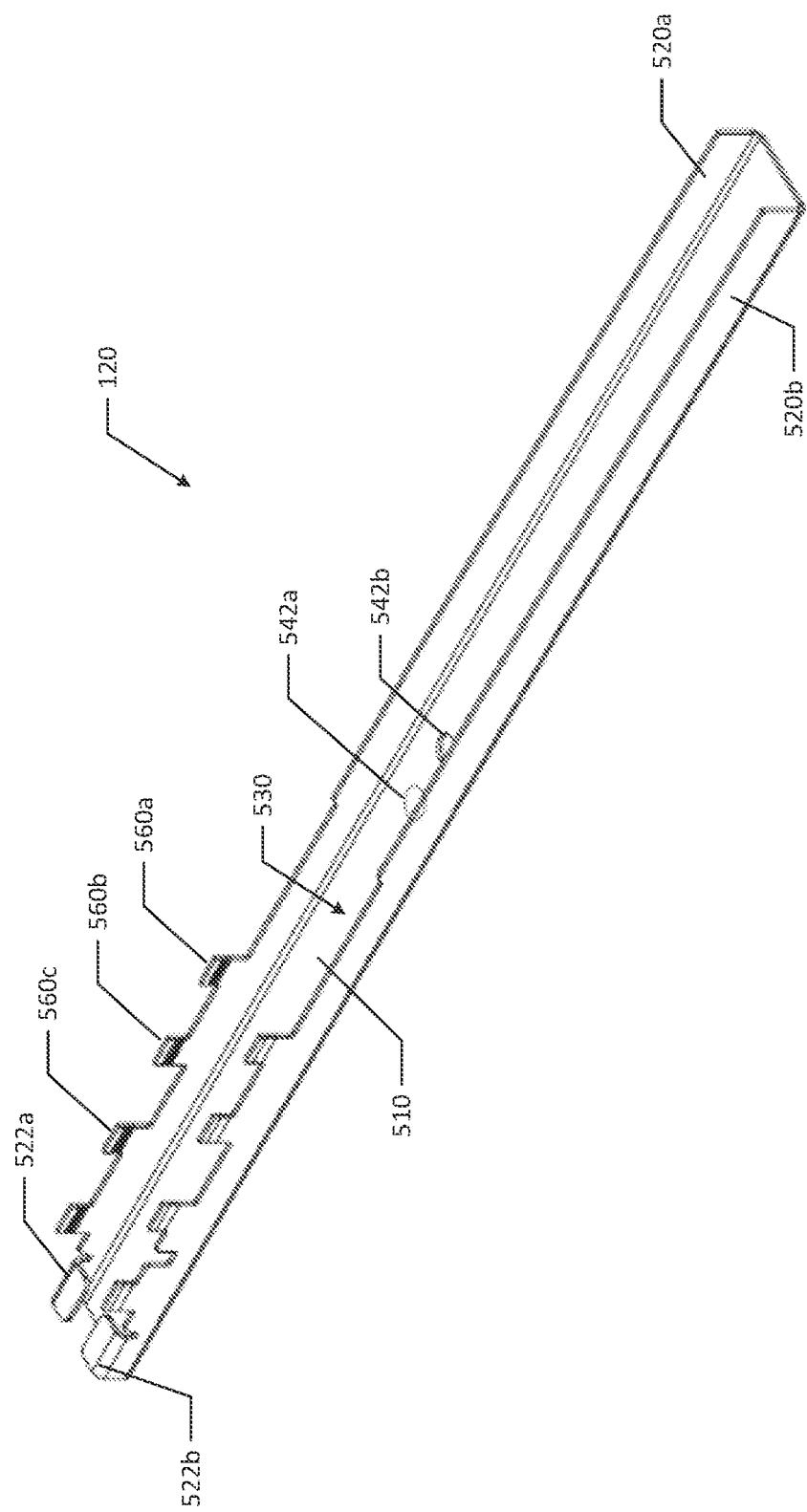
FIG. 5G illustrates yet another example main rail according to the present disclosure.

FIG. 5G illustrates yet another example of the main rail 120 (e.g., the main rail 120 of FIG. 1J). Similar to the main rail 120 of FIG. 5F, the main rail 120 of FIG. 5G also includes the base 510, the sidewalls 520a and 520b that form channel 530, and include the holes 542a and 542b. Additionally, in the illustrated example of FIG. 5G, the main rail 120 also includes a plurality of elongate members (hereinafter referred to as elongate members 560) exemplified by elongate members 560a, 560b, and 560c. In some examples, the elongate members 560 can be used to mechanically couple the main rail 120 to a window cover (e.g., the window cover 108 of FIG. 1K).

As illustrated in FIGS. 6A, 6B and 6C, the jaw closer 130 includes an elongate base 610 with two drive flanges 682 and 684 that are configured to couple to respective ends of levers 184b and 184a (see FIG. 1B), which is discussed in more detail below. The jaw closer 130 has a proximal end 601 and a distal end 603. Additionally, the jaw closer 130 includes a slot 640 that accommodates jaw anchor 190. The slot 640 is an oval slot that is adapted to limit the range of motion of the jaw closer 130 by providing a front-stop 642 and a back-stop 644 for the jaw anchor 190. Specifically, the jaw closer 130 may move forward, towards the distal end 103 of the clip applier 100, until the jaw anchor 190 abuts the back-stop 644. Similarly, the jaw closer 130 may move backward, toward the proximal end 101 of the clip applier 100, until the jaw anchor 190 abuts the front-stop 642 of the slot 640.

The jaw closer 130 also includes a pawl track 652 to accommodate a positioning post 1120 and flanges 1130a and 1130b of the ratchet pawl 192 (see FIG. 11A). The pawl track 652 is sized and shaped to allow the ratchet pawl 192 to rotate and freely move within the pawl track 652 while the main rail 120 remains fixedly coupled to the bottom housing 104.

Figure 6D:
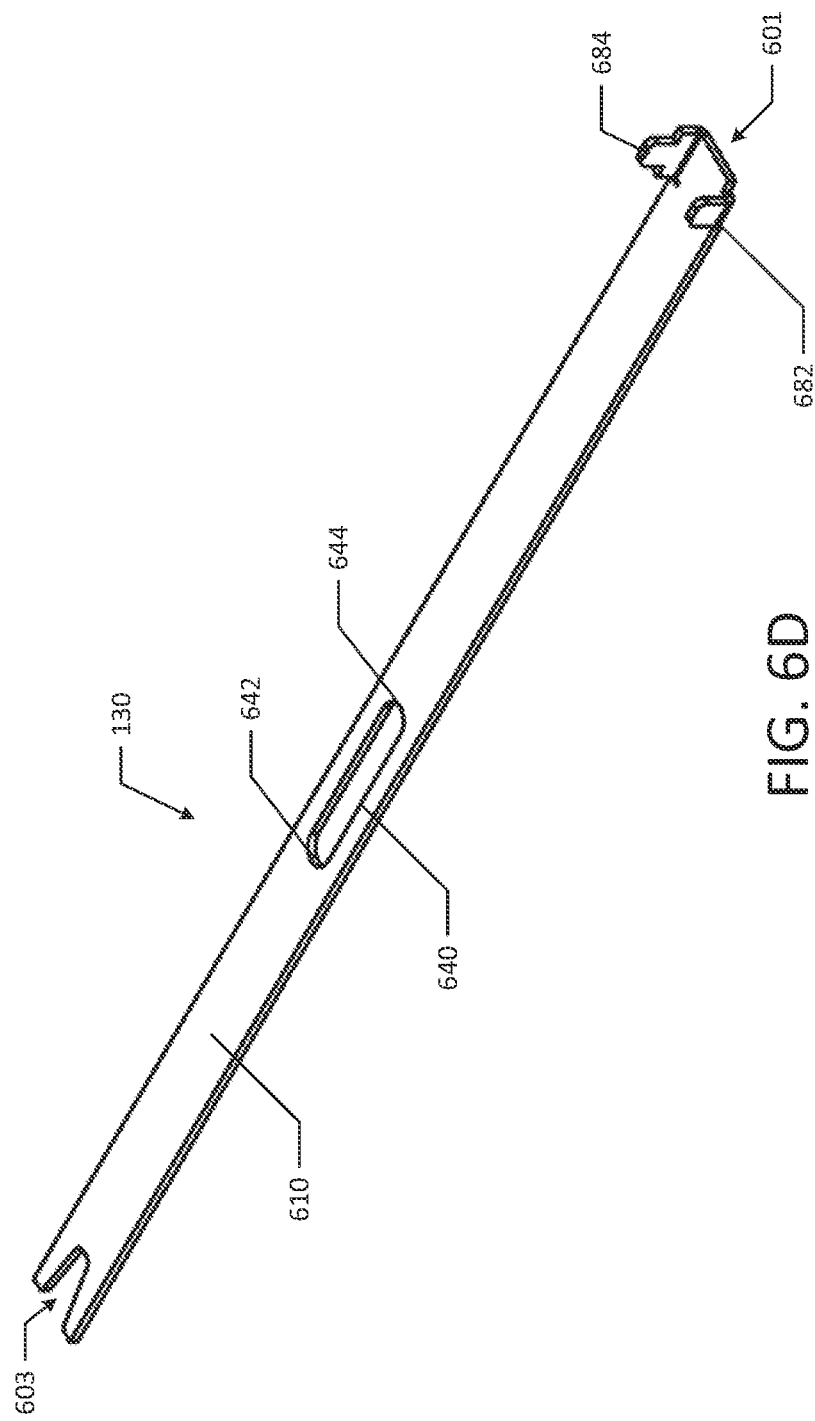
FIGS. 6D and 6E illustrate another example jaw closer according to the present disclosure.
Figure 7A:
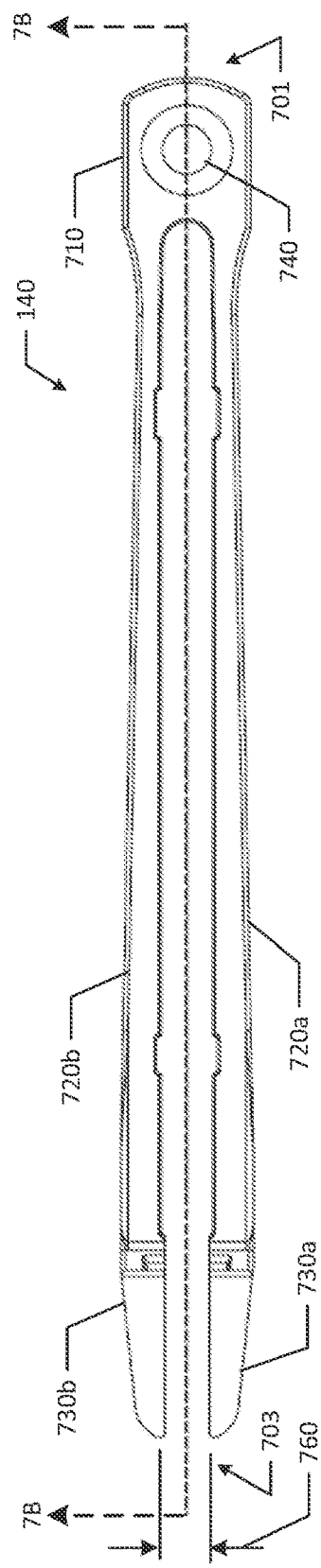
FIGS. 7A, 7B, 7C and 7D illustrate an example pair of clip applying jaws according to the present disclosure.
Figure 7B:
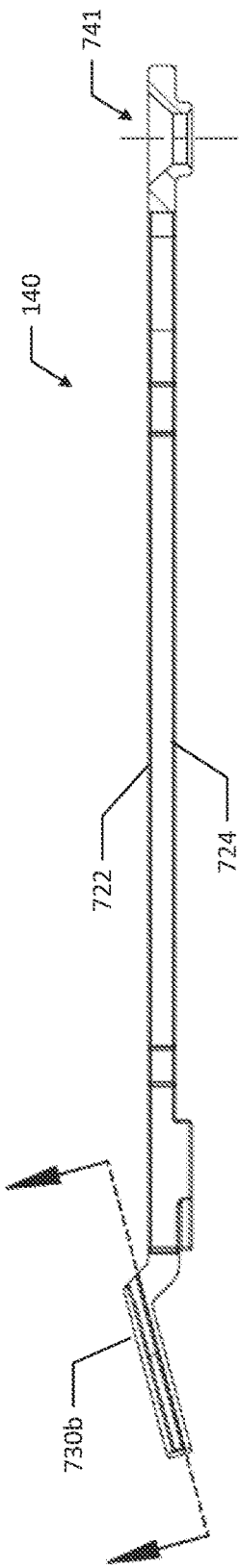
Figure 7C:
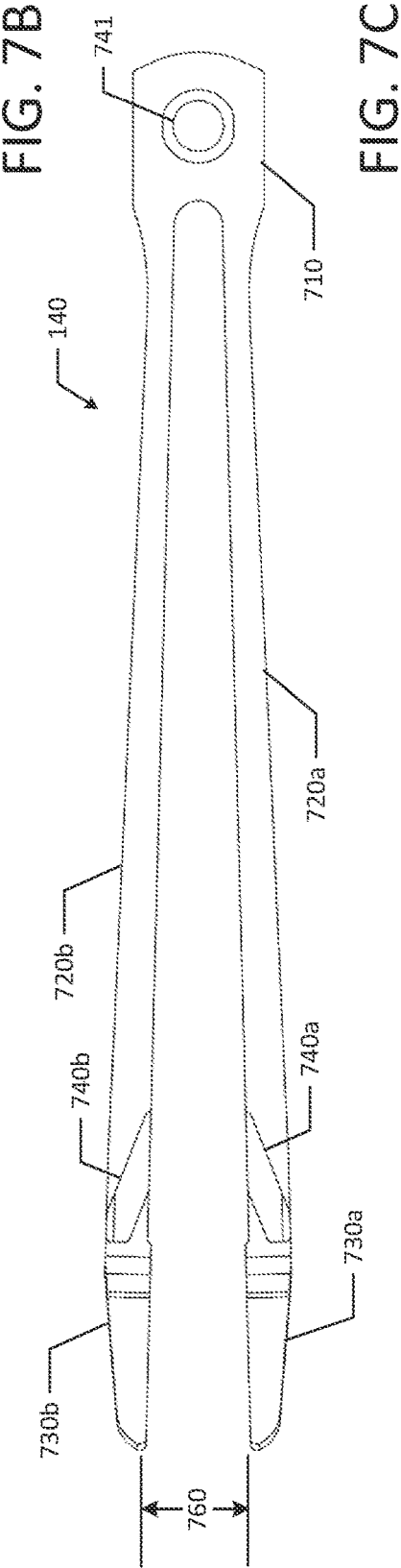

The jaw closer 130 also includes an engagement indent 650 with cam members 652a and 652b that cooperate with ramps or protrusions on the clip applying jaws 140 (see FIGS. 7B and 7C). For example, the cam members, generally referred to as cam members 652, may form the indent 650, which is configured to close the clip applying jaws 140 as the jaw closer 130 is extended towards the distal end 103 (e.g., clip applying end) of the clip applier 100. As illustrated in FIG. 6C, which is an enlarged detail view of the distal end 603 of the jaw closer 130 showing the geometry of engagement indent 650, the engagement indent 650 has a triangular shape. It should be appreciated that the engagement indent 650 is sized and shaped to cooperate with corresponding camming surfaces on the clip applying jaws 140, and therefore other shapes, geometries or means of closing the clip applying jaws 140 may be implanted. Similar to the main rail 120, the jaw closer 130 may be fabricated from plastic or metal. In an example, the jaw closer is fabricated as a stamped metal piece. In one example, the jaw closer 130 is made from stainless steel (e.g., half hard 304 SS).

After the jaw closer 130 is positioned within the main rail 120, the clip applying jaws 140 are positioned atop the jaw closer 130. Specifically, the clip applying jaws 140 are positioned above the main rail 120 and secured in place via jaw anchor 190, which passes through a corresponding slot or thru-hole of the clip applying jaws 140 before passing through slot 640 of jaw closer 130 and thru-hole 540 of the main rail. The jaw anchor 190 secures the clip applying jaws 140 in place by anchoring the clip applying jaws to the corresponding slot 195 in the lower housing 104.

Figure 6E:
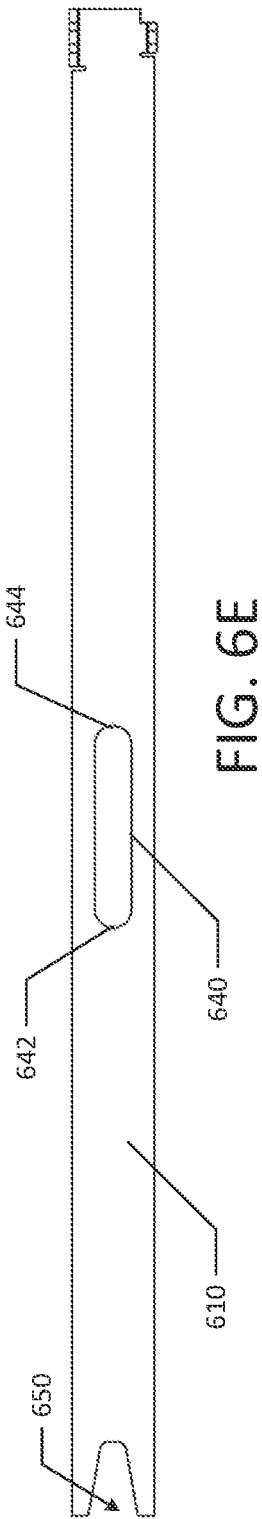

FIGS. 6D and 6E illustrate an alternative embodiment of the jaw closer 130. In the alternate embodiment (e.g., jaw closer 130 of FIG. 1C), the jaw closer 130 includes many of the same features of the jaw closer 130 illustrated in FIGS. 6A-6D. However, in the illustrated example, the jaw closer 130 is shown without a pawl track 652.

The clip applying jaws 140 are further described and illustrated in FIGS. 7A, 7B, 7C and 7D. In the illustrated example, the clip applying jaws include a body portion 710 at a proximal end and arms 720a, 720b (e.g., right arm 720a and left arm 720b) that extend from the body portion 710 towards a distal end of the clip applying jaws 140. Additionally, the clip applying jaws 140 includes an opening or thru-hole 741 that accommodates jaw anchor 190. The arms 720a and 720b, hereinafter referred to generally as arms 720 terminate in cooperating jaw heads 730a, 730b at the distal end 703.

The jaw heads 730a, 730b, which are referred to generally as jaw heads 730, are oriented in a downward sloping position. At the end of the arms 720, where the jaw heads 730 start, the jaw heads 730 are initially positioned above the arms 720, such that the jaw heads 730 are stepped above a top surface 722 of the arms and slope downward such that the end of the jaw heads 730 at the distal end 703 are approximately in-line with a bottom surface 724 of the arms 720 (see FIG. 7B).

Each respective arm 720 includes a ramp or protrusion (e.g., ramps 740a and 740b) that are configured to cooperate with cam members 652 or indent 650 of the jaw closer (see FIGS. 6B and 6C). When the ramps 740a and 740b, generally referred to herein as ramps 740, cooperate with the indent 650, the clip applying jaws 140 are transitioned to a closed position. In the closed position, the jaw heads 730 are moved towards each other to crimp or pinch together a surgical clip. Specifically, as the jaw closer 130 is extended towards the distal end 103 (e.g., clip applying end) of the clip applier 100, the ramps 740 ride along the cam members 652 of the jaw closer, which forces the arms 720 and the jaw heads 730 closer together.

In the illustrated examples, FIG. 7C illustrates the clip applying jaws 140 in an open configuration with the arms 720 and jaw heads 730 spread apart. Conversely, FIG. 7A illustrates the clip applying jaws 140 in a closed configuration with the arms 720 and jaw heads 730 in a parallel arrangement with a smaller clip gap. For example, the clip gap 760 (open position) of FIG. 7C is larger than the clip gap 760 (closed position) of FIG. 7A.

As illustrated in FIG. 7C, the ramps 740, which function as cam surfaces, are located behind the respective jaw heads 730, towards the distal end 703 of the clip applying jaws 140. The ramps 740, when pressed together and viewed from above, may have a triangular shape that cooperates with the triangular shaped indent 650 of the jaw closer 130. As the jaw closer 130 retreats, the arms 720 and their corresponding jaw heads 730 are released to move back to the open position. In an example, the arms 720 and their corresponding jaw heads 730 are biased (e.g., spring biased) to the open position and only close through interaction with the jaw closer 130. For example, the jaws may have a natural spring bias to an open position and are forced closed when the jaw closer 130 is extended towards the distal end 703 of the clip applying jaws 140 for crimping a surgical clip during surgery.

Figure 7D:
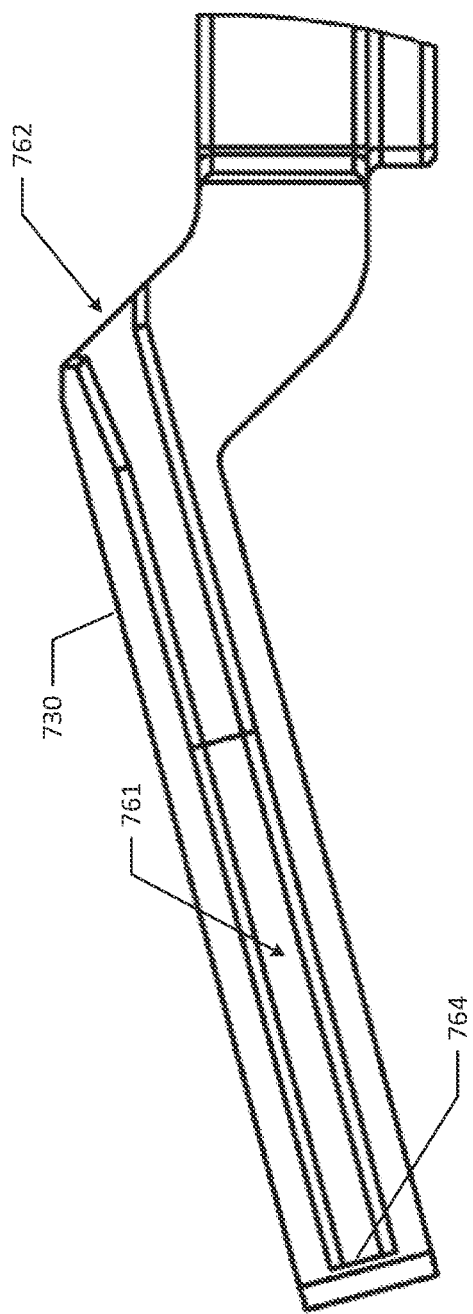

As illustrated in FIG. 7D, each jaw head 730 has a recessed channel 761 (e.g., recessed channel 761a on jaw head 730a and recessed channel 761b on jaw head 730b) that cooperate to form a clip track 770. For example, the recessed channels 760 or groove is sized and shaped to allow a leg of a surgical clip to slide along the channel 760. The clip track 770 formed between the jaw heads 730 is configured to provide a track that guides a surgical clip as the surgical clip travel to the distal end 703 of the clip applying jaws 140. For example, and as discussed in more detail below, as the clip applying jaws 140 open, a clip pusher assembly 150 (see FIGS. 2A, 2B, 2C and 8A) moves towards the distal end 703 of the clip applying jaws 140 and pushes a surgical clip into the jaw heads 730. More specifically, the clip pusher pushes and positions the surgical clip into the clip track 770 formed by the cooperating recessed channels 761 of the jaw heads 730. Then, the surgical clip travels along the clip track 770 until the surgical clip reaches the distal end 703, where the clip applying jaws are transitioned to a closed position to crimp the surgical clip.

Each recessed channel 761 starts with an opening 762 and ends at a stop surface 764 before reaching the distal end of the clip applying jaws 140. The opening 762 may be larger than the height or diameter of the channel 761 to aid in aligning and positioning the respective surgical clip leg within the channel 761. The stop surface 764 may advantageously prevent surgical clips from traveling beyond the distal end 703 of the clip applying jaws 140 prior to application. For example, without stop surface 764, surgical clips may incidentally fall out of the clip applier 100 before the clip applier 100 and the clip applying jaws 140 transition to a closed position to crimp and apply the surgical clip to the surgical site.

FIGS. 7E and 7F illustrate another example of jaw head 730. Specifically, in an alternate embodiment, the jaw head 730 may similarly include a recessed channel 761 (e.g., recessed channel 761a on jaw head 730a and recessed channel 761b on jaw head 730b) that cooperate to form a clip track 770. For example, as illustrated in FIG. 7F, a portion of the jaw head 730 may be removed thereby forming a larger opening 762 at the start of the channel 761. The opening 762 may be larger than the height or diameter of the channel 761 to aid in aligning and positioning the respective surgical clip leg within the channel 761. Additionally, the material removed from the jaw head 730 near region 765 may further aid in aligning and positioning the respective surgical clip leg within the channel 761.

Once the clip applying jaws 140 are positioned within the enclosure, the clip loader assembly 150 is positioned above the clip applying jaws. As mentioned above, the clip loader assembly 150 includes a proximal clip loader 154 and a distal clip loader 152. The clip loader assembly 150 cooperates with handles 106 and various other internal components, such that the distal clip loader 154 moves in a linear reciprocating motion for loading clips into the clip applying jaws.

Figure 8A:
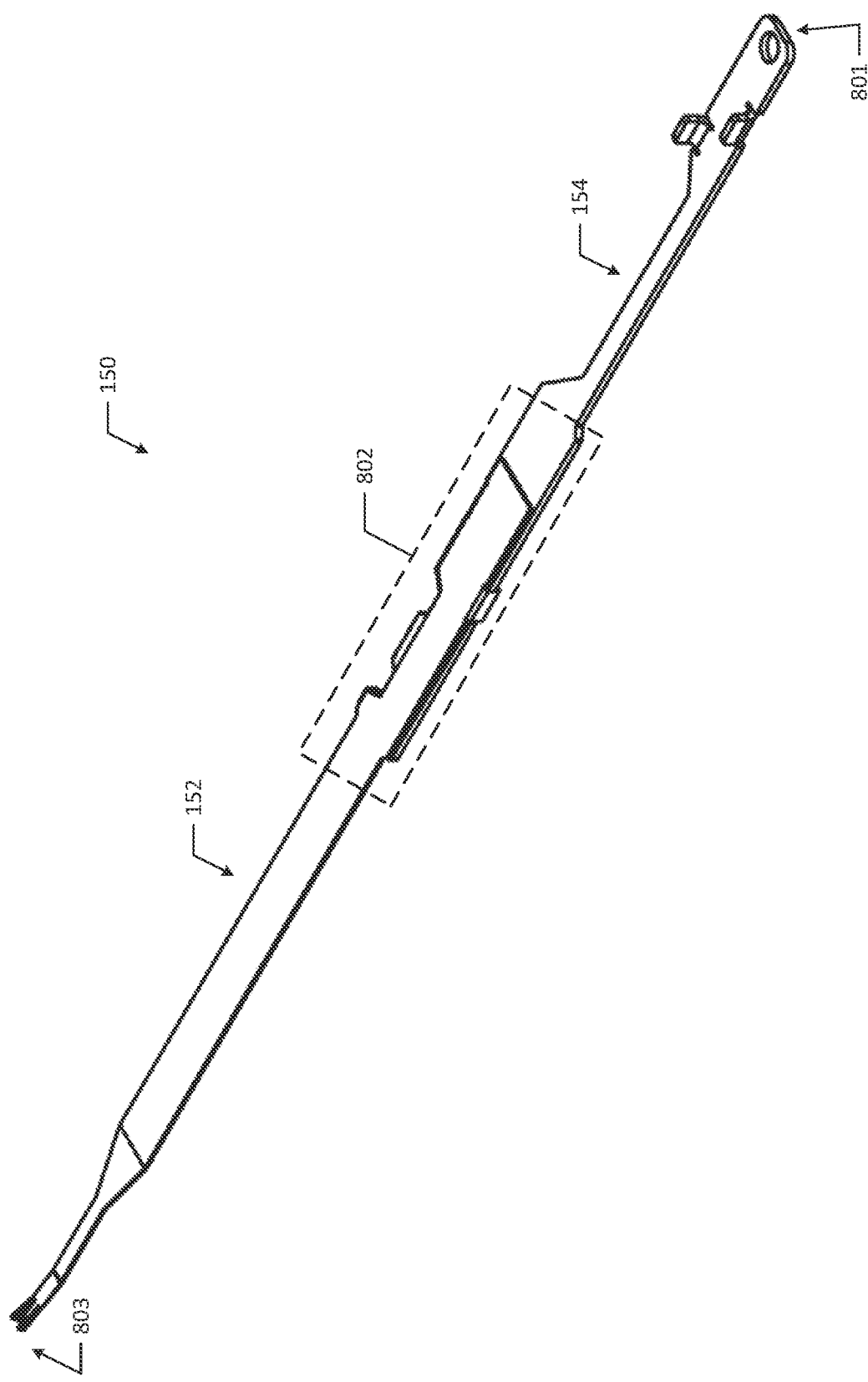
FIG. 8A illustrates an example clip loader assembly according to the present disclosure.

FIG. 8A illustrates an example of the clip loader assembly 150 having a proximal end 801 and a distal end 803. The clip loader assembly 150 includes a proximal clip loader 154 and a distal clip loader 152. In an example, the proximal clip loader 154 and the distal clip loader 152 may be spot welded together at various locations or points within weld region 802.

FIGS. 8B, 8C, 8D and 8E illustrate various views of an example proximal clip loader 154. The proximal clip loader 154 may be fabricated from plastic or metal. In an example, the proximal clip loader 154 is fabricated as a stamped piece(s) of metal. In one example, the proximal clip loader is made from stainless steel (e.g., 316 SS). The proximal clip loader 154 includes an elongate base 810 with two retention flanges 820a and 820b that are adapted to engage corresponding structures on the top housing 102 to further align (e.g., align in the horizontal direction) and secure the proximal clip loader 154 in place. Additionally, a portion of the elongate base 810 has an engagement portion 815 that includes a plurality of teeth 817. The engagement portion, and more specifically the plurality of teeth 817 are configured to cooperate with ratchet pawl 192. For example, the proximal clip loader has an engagement portion 815 with teeth 817 and two indented notches 818a and 818b positioned on opposite sides of the engagement portion 815. The plurality of teeth 815 and indented notches 818a, 818b (hereinafter referred to generally as indented notches 818) function as an anti-backup mechanism, which is described in more detail below. The plurality of teeth 817 are illustrated in more detail in FIG. 8E, which is a detail view of FIG. 8D.

The proximal clip loader 154 also includes a drive aperture 830 that is configured to accommodate a drive flange (e.g., drive flange 1510, see FIG. 15A) of the proximal lever 182a of the right lever assembly 180a. For example, proximal clip loader 154 is positioned over the proximal lever 182a, such that the drive flange 1510 (see FIG. 15A) of the proximal lever 182a extends upwards through the drive aperture 830. Once the drive flange of the proximal lever 182a is positioned through the drive aperture 830, a corresponding thru-hole (e.g., thru-hole 1404, see FIG. 14A) of proximal lever 182b is positioned over the remaining portion of the drive flange 1510 that extends above the proximal clip loader 154. For example, the drive aperture 830 is aligned with the corresponding thru-hole 1404 of the proximal lever 182b.

FIGS. 8F, 8G, 8H and 8J illustrate various views of an example distal clip loader 152. The distal clip loader 152 may be fabricated from plastic or metal. In an example, the distal clip loader 152 is fabricated as a stamped piece(s) of metal. In one example, the proximal clip loader is made from stainless steel (e.g., 316 SS). The proximal clip loader 152 includes an elongate base 860 with two flanges 862a and 862b that are adapted to engage corresponding structures on the proximal clip loader 154 for alignment prior to spot welding. The distal clip loader 152 also includes a notched window 864, such that when the distal loader 152 is positioned over the proximal clip loader 154, the window 864 provides access to the engagement portion 815 with teeth 817 and two indented notches 818 of the proximal clip loader 154. It should be appreciated that instead of stacking and spot welding the proximal clip loader 154 to the distal clip loader 152, the clip loader assembly 150 may instead be fabricated as a single piece.

Figure 9A:
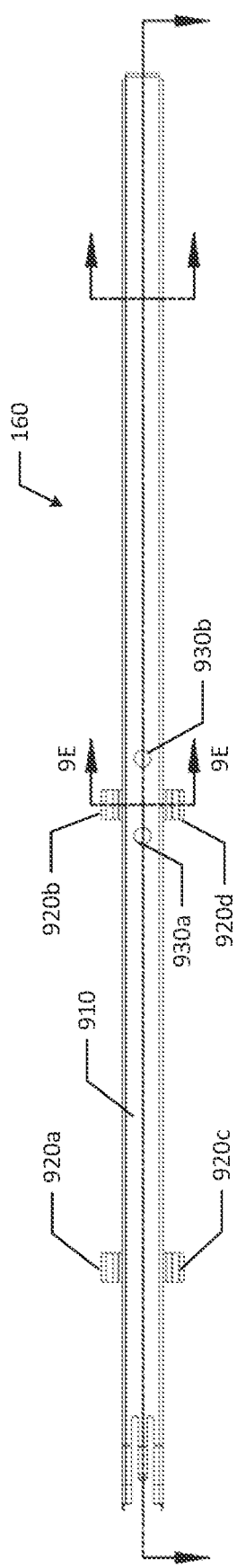
FIGS. 9A, 9B, 9C, 9D and 9E illustrate an example dispenser according to the present disclosure.
Figure 9B:
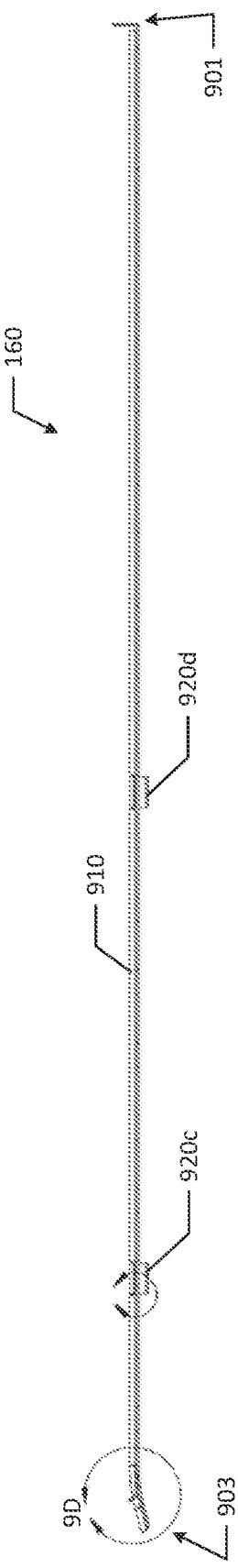
Figure 9C:
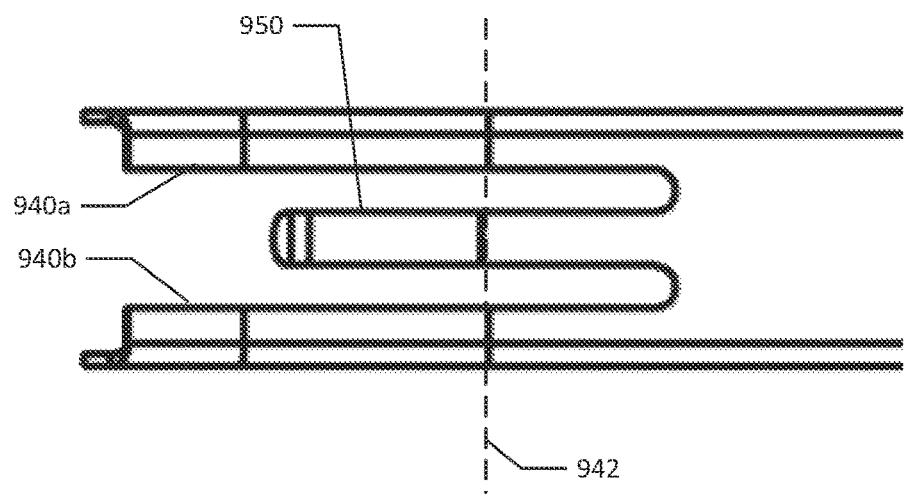
Figure 9D:
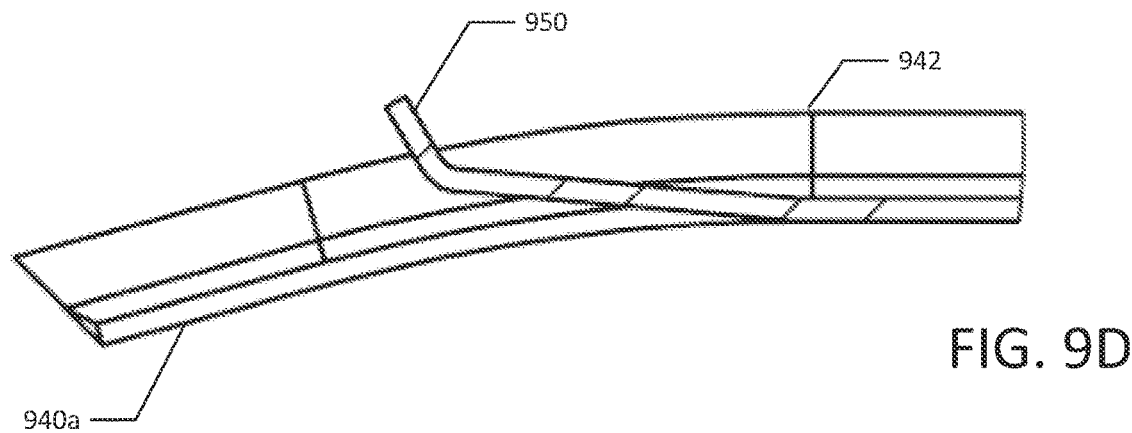

The end of the distal clip loader (e.g., the end corresponding to the distal end 803 of the clip loader assembly 150), includes a clip loading tip 870. Prior to reaching the clip loading tip 870, the elongate base 860 narrows at a clip loading portion 866 of the elongate base 860. Additionally, the clip loading portion 866 curves upward at shoulder 871 until terminating at the clip loading tip 870. The clip loading portion 866 narrows to reduce the width of the elongate base 860, thereby allowing the distal clip loader 152, and more specifically the clip loading tip 870 to engage with individual surgical clips of a clip magazine. During application, the distal clip loader 152 pushes a leading surgical clip from the clip magazine over a retention prong 950 of the dispenser 160 (see FIGS. 9C and 9D).

In an example, and as illustrated in FIG. 8J, the clip loading tip 870 is curved upwards and forms a U-shaped channel with base 872 and sidewalls 874a and 874b. The U-shaped channel is sized and shaped to fit around the retention prong 950 and between the forks 940a and 940b of the dispenser (see FIGS. 2A, 2B, 9C and 9D), allowing the clip loading tip 870 to engage the leading surgical clip without the clip loading tip 870 contacting the retention prong 950 or forks 940a, 940b. For example, sidewalls 874a and 874b contact respective points of the leading surgical clip 50 that overhang on each side of the retention prong. Pushing the leading surgical clip 50 over the retention prong is further illustrated in FIGS. 2A and 2B.

FIGS. 8K, 8L and 8M illustrate another example clip loader assembly 150. In the illustrated example, the clip loader assembly 150 includes a distal clip loader 152 and a proximal clip loader 154. The detail view illustrated in FIG. 8M illustrates where the proximal clip loader 154 and the distal clip loader 152 may be spot welded together. For example, the proximal clip loader 154 may be spot welded to the distal clip loader 152 at various locations or points (e.g., weld points 802a and 802b) within a weld region. The distal clip loader 152 illustrated in FIG. 8K has many of the same features as the clip loader 152 illustrated in FIG. 8F.

FIGS. 8N, 8P and 8Q illustrate another example of proximal clip loader 154. Similar to the proximal clip loader 154 illustrated in FIG. 8B, the proximal clip loader 154 illustrated in FIG. 8N includes an elongate base 810 and drive aperture 830 that is configured to accommodate a drive flange (e.g., drive flange 1510, see FIG. 15A) of the proximal lever 182a of the right lever assembly 180a. For example, proximal clip loader 154 is positioned over the proximal lever 182a, such that the drive flange 1510 (see FIG. 15A) of the proximal lever 182a extends upwards through the drive aperture 830. Once the drive flange of the proximal lever 182a is positioned through the drive aperture 830, a corresponding thru-hole (e.g., thru-hole 1404, see FIG. 14A) of proximal lever 182b is positioned over the remaining portion of the drive flange 1510 that extends above the proximal clip loader 154. For example, the drive aperture 830 is aligned with the corresponding thru-hole 1404 of the proximal lever 182b. The proximal clip loader 154 also includes an alignment slot 832 as well as a vertical spacing and alignment protrusion 834.

FIGS. 9A, 9B, 9C, 9D and 9E illustrate various views of an example dispenser 160. The dispenser 160 may be fabricated from plastic or metal. In an example, the dispenser 160 is fabricated as a stamped piece(s) of metal. In one example, the dispenser 160 is made from stainless steel (e.g., half hard 304 SS). The dispenser 160 includes an elongate base 910 with flanges 920a, 920b, 920c and 920d, which may serve as a securing flange or snap. For example, the flanges 920a-d may form a press-fit or snap-fit with corresponding structures on bottom housing 104. Additionally, the dispenser 160 includes two openings or thru-holes 930a and 930b, which may be adapted to assist with initial placement and alignment of the dispenser 160. The dispenser 160 has a proximal end 901 and a distal end 903.

At the distal end 903, the dispenser includes forks 940a and 940b that curve downward from the elongate base 910 at shoulder 942. Additionally, the dispenser 160 includes a retention prong 950 that curves upward from the elongate base 910 at the shoulder 942 (see FIGS. 9C and 9D). The forks 940a and 940b, hereinafter referred to generally as forks 940, create both a support surface and a track for the legs of a surgical clip 50. Additionally, the forks 940 are sized and shaped similar to the cooperating recessed channels 760 of the jaw heads 730, which form the clip track 770. For example, the forks 940 curve downward such that the end of forks directly lead into the cooperating recessed channels 760 of the jaw heads (see FIGS. 2A and 2B). Therefore, the forks 940 curve to have the same slope (at their distal ends) as the cooperating recessed channels 760.

As mentioned above, the retention prong 950 is curved upwards to retain the leading surgical clip 50 until the leading clip is pushed off of the retention prong 950 by the clip loading tip 870. The retention prong 950 is adapted to have enough rigidity to support and retain a leading surgical clip 50 while also having enough flexibility to enable the clip loading tip 870 to temporarily bend the retention prong 950 downward to allow the leading surgical clip 50 to advance beyond the retention prong 950, along the forks 940 and through the clip track 770 formed by the cooperating recessed channels 760 of the jaw heads 730.

Figure 9E:
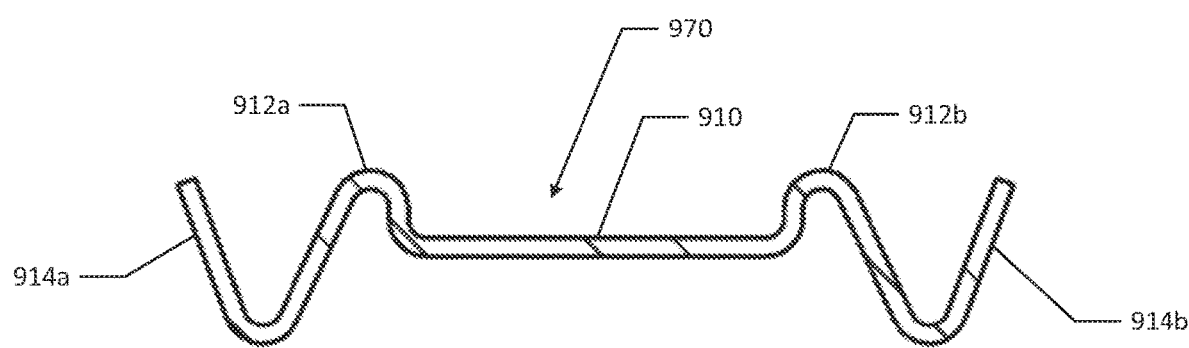

As illustrated in FIG. 9E, the elongate base 910 may include two ridges 912a and 912b that form a channel 970. The channel 970 is adapted to receive the clip pusher assembly 170, which includes a clip pusher spring 172 and a clip pusher bar 174, described in more detail below. Additionally, the elongate base 910 includes two V-shaped flanges 914a and 914b with a first leg of each V-shaped flange 914 extending downward from the ridge 912 below the elongate base 910 before the second leg of the V-shaped flange 914 extends back upward to the height of the top of the ridge 912. The V-shaped flange(s) 914 may be adapted for alignment and attachment. For example, the V-shaped flange(s) 914 may be press-fit into a corresponding mating structure in the housing. For example, the V-shaped flange(s) 914 may first compress inwardly and then snap-back and hook into the corresponding mating structure in the housing.

FIGS. 9F, 9G, 9H and 9I illustrate another example dispenser 160. Similar to the dispenser 160 illustrated in FIG. 9A, the dispenser 160 illustrated in FIG. 9F includes an elongate base 910. Instead of flanges (e.g., flanges 920a, 920*b*, 920*c* and 920*d* illustrated in FIG. 9A), the dispenser 160 may include various attachment members 925*a-f*, which may include square shaped thru-holes that are adapted to engage with corresponding securing features of the bottom housing 104 (e.g., in a snap-fit or press-fit engagement).

The dispenser 160 has a proximal end 901 and a distal end 903. Similar to the embodiment illustrated in FIG. 9A, the example illustrated in FIG. 9F includes forks 940*a* and 940*b* (at the distal end 903) that curve downward from the elongate base 910. Additionally, the dispenser 160 includes a retention prong 950 that curves upward from the elongate base 910 to retain the leading surgical clip 50 until the leading clip is pushed off of the retention prong 950 by the clip loading tip 870.

As illustrated in FIG. 9G and FIG. 9H, the dispenser 160 may include sidewalls 935*a* and 935*b* that fold over to form a spring retention channel 937 near the proximal end 901 of the dispenser 160. The spring retention channel 937 may advantageously house clip pusher spring 172 (see FIG. 1B) and prevent the clip pusher spring 172 from buckling and popping out of channel 937 or channel 970. For example, without spring retention channel 937, the clip pusher spring 172 may buckle and lose containment when the stack 105 of clips is near empty. Moving from the proximal end 901 towards the distal end 903, and after the spring retention channel 937, the attachment members (e.g., attachment members 925*c* and 925*f*) may be formed from sidewalls of the dispenser 160 and may form channel 970 (as illustrated in FIG. 9I). The channel 970 is adapted to receive the clip pusher assembly 170, which includes a clip pusher spring 172 and a clip pusher bar 174, described in more detail below.

FIGS. 9J, 9K, 9L, 9M, and 9N illustrate yet another example dispenser 160 (e.g., the dispenser 160 of FIG. 1K). FIG. 9J illustrates a perspective view of an alternate embodiment of the dispenser 160. FIGS. 9K, 9L, and 9M illustrate cross-section views of the dispenser 160 of FIG. 9J. FIG. 9N illustrates a partial side view of the dispenser 160 of FIG. 9J. The example dispenser 160 illustrated in FIGS. 9J-9N includes a proximal end 901, a distal end 903, an elongate base 910, a spring retention channel 937, forks 940*a* and 940*b*, a retention prong 950, and a channel 970 that are similar, respectively, to the proximal end 901, the distal end 903, the elongate base 910, the spring retention channel 937, the forks 940*a* and 940*b*, the retention prong 950, and the channel 970 of the example dispenser 160 of FIGS. 9F-9I. However, it is noted that the shapes and sizes of one or more of these components may vary. For example, the dimensions and/or shapes of channels 937 and/or 970 of the dispenser 160 of FIGS. 9J-9N could differ from the dimensions/shapes of the channels 937 and/or 970 of the dispenser of FIGS. 9F-9I. As another example, as best shown in FIG. 9N, the retention prong 950 of this illustrated example has a different shape than the example retention prong 950 illustrated in FIG. 9C.

In the illustrated example of FIGS. 9J-9N, the dispenser 160 also includes a plurality of connectors (hereinafter referred to as connectors 926) exemplified by connectors 926*a*, 926*b*, and 926*c* (e.g., attachment mechanisms, etc.). The connectors 926 can be used to mechanically couple (e.g., via a snap-fit or press-fit engagement) the dispenser 160 to corresponding sockets of a window cover (e.g., sockets 1304*a*, 1304*b*, 1304*c*, etc. of the window cover 108 illustrated in FIGS. 13D-13F).

As best shown in FIG. 9L, a shape (e.g., width) of channel 970 is defined by various walls (e.g., connectors 926*b*, 926*c*, base 910, etc.) of the dispenser 160. In this example, the channel 970 is adapted to receive clip pusher spring 172 and the clip pusher bar 174 (e.g., see FIGS. 1G and 1K). Similarly, as best shown in FIG. 9M, a shape (e.g., width, etc.) of the spring retention channel 937 is defined by various walls of the dispenser 160, including folded sidewalls 936*a* and 936*b*. Similar to the example dispenser 160 of FIGS. 9F-9I, the spring retention channel 937 of FIGS. 9J-9N could prevent and/or reduce the likelihood of clip pusher spring 172 popping out of the channels 937 and/or 970.

Figure 10A:
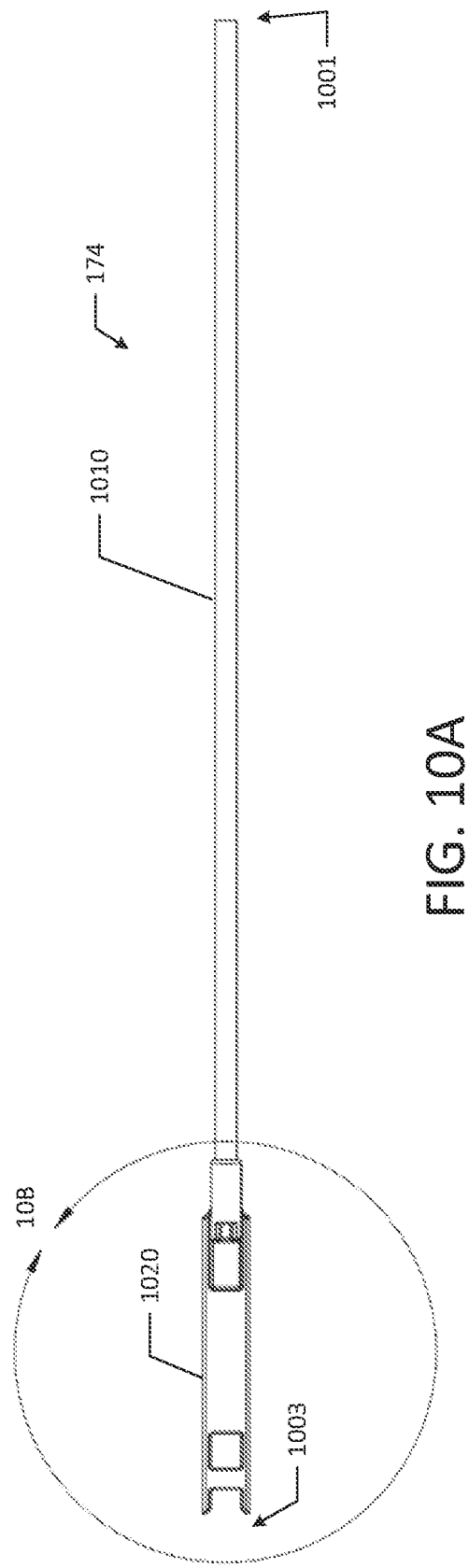
FIGS. 10A and 10B illustrate an example clip pusher bar according to the present disclosure.
Figure 10B:
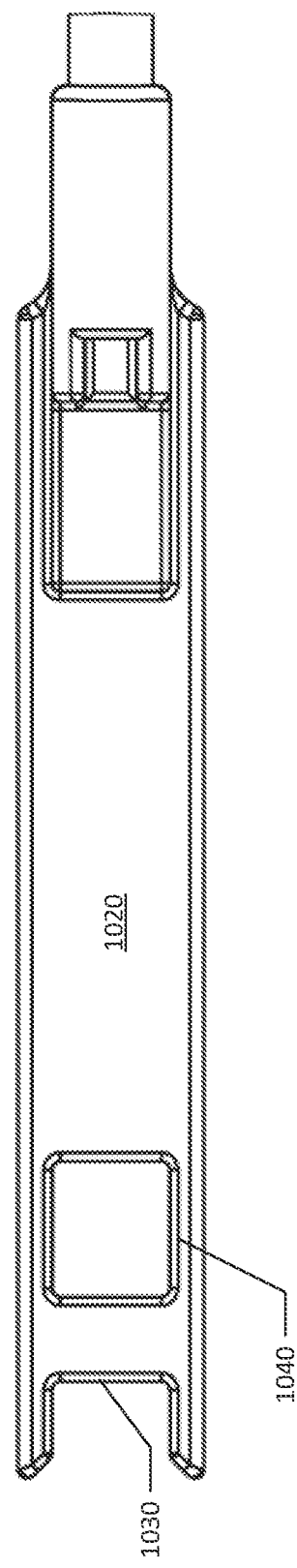
Figure 10C:
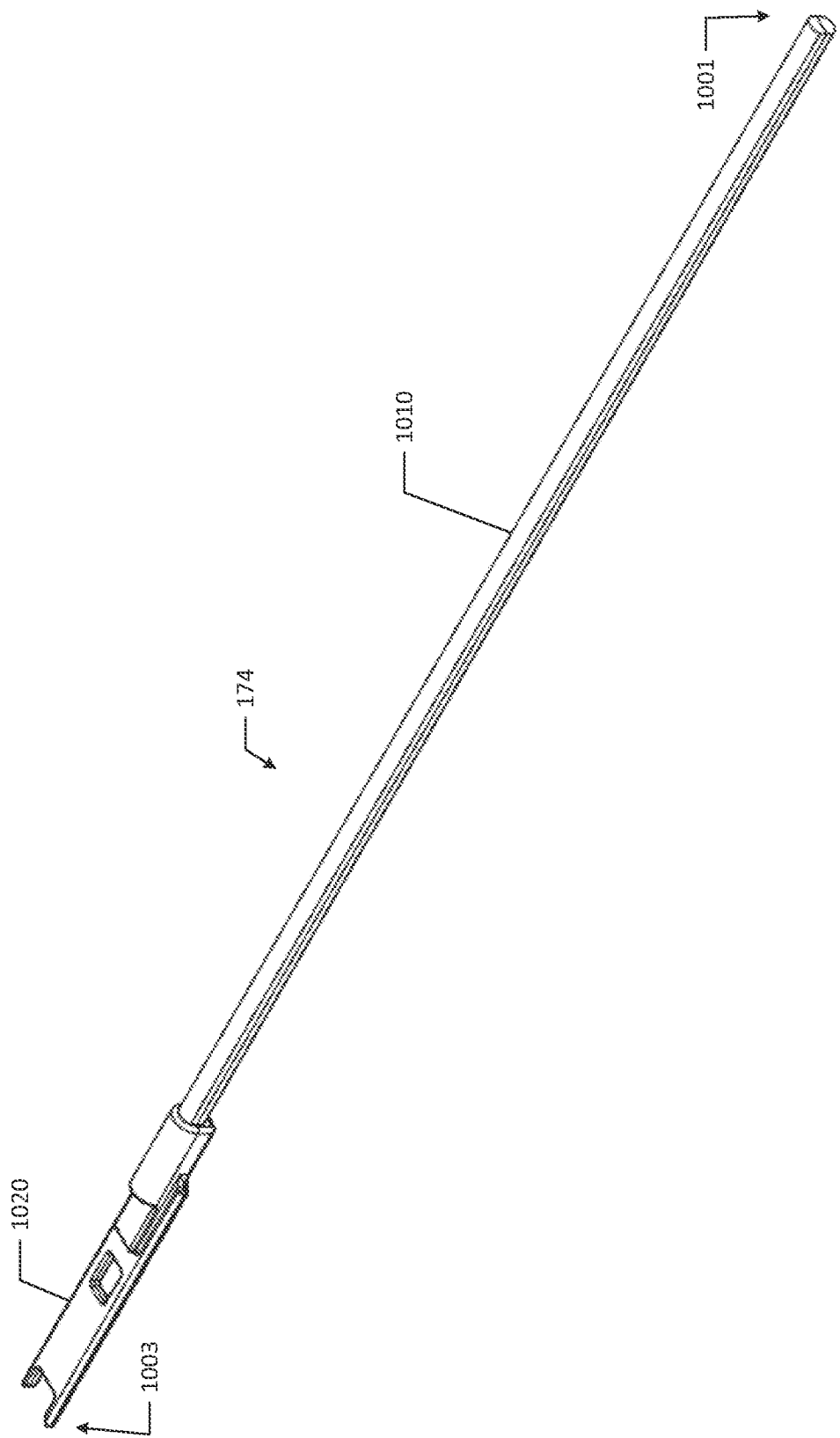
FIG. 10C illustrates another example clip pusher bar according to the present disclosure.

FIGS. 10A and 10B illustrate an example of the clip pusher bar 174. The clip pusher bar 174 and clip pusher spring 172 (see FIG. 1B) may be coupled together to form the clip pusher assembly 170. For example, the proximal end 1001 of the clip pusher bar 174 may be mounted to a distal end of the clip pusher spring 172. The clip pusher bar 174 includes an elongate shaft 1010 that is adapted to couple to the clip pusher spring 172. At the other end of the elongate shaft 1010, the clip pusher bar 174 includes a clip pusher head 1020 with a surgical clip contact notch 1030. Additionally, the clip pusher bar 174 may include a lock-out window 1040 that is adapted to be grabbed by prong 950 to bring the clip pusher head 1020 into the jaws 730 thereby locking-out the jaws 730 after the last surgical clip 50 was applied and dispensed. FIG. 10C illustrates another example clip pusher bar 174 that has many of the same features as the clip pusher bar illustrated in FIGS. 10A and 10B, but instead of including a lock-out window 1040, the clip pusher bar 174 of FIG. 10C is adapted for use with a lock-out clip (e.g., lock-out clip 185 as illustrated in FIG. 1C, FIG. 1K, FIGS. 16A-B, and/or FIG. 16C).

The clip pusher spring 172 provides a constant biasing force to the clip pusher bar 174 thereby causing the clip pusher head 1020, and more specifically the clip contact notch 1030, to continually apply pressure to the clip magazine. The constant pressure ensures that a next-leading surgical clip is advanced to the retention prong 950 of the dispenser 160. For example, both the clip pusher bar 174 and the clip magazine travel along the channel 970 of the dispenser 160 until the leading surgical clip 50 contacts the retention prong 950. As discussed above, the leading surgical clip 50 is retained by the retention prong 950 until the clip is released (e.g., pushed forward) by the clip loading tip 870.

In an example, a surgical clip magazine (not pictured) may carry a stack 105 of surgical clips 50 (e.g., a stack 105 of fifteen surgical clips 50). The clip pusher assembly 170 provides a biasing force to the stack of surgical clips in the magazine until the magazine is empty. Referring back to FIG. 2F, the stack of surgical clips are illustrated with a leading surgical clip 50 at the end of the clip applying jaws 140.

Figure 11E:
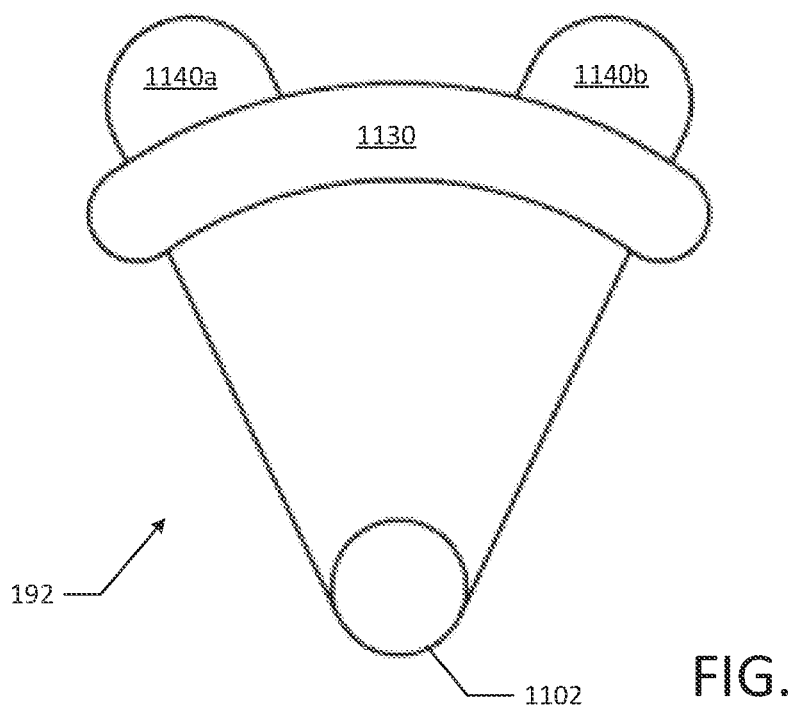
Figure 12B:
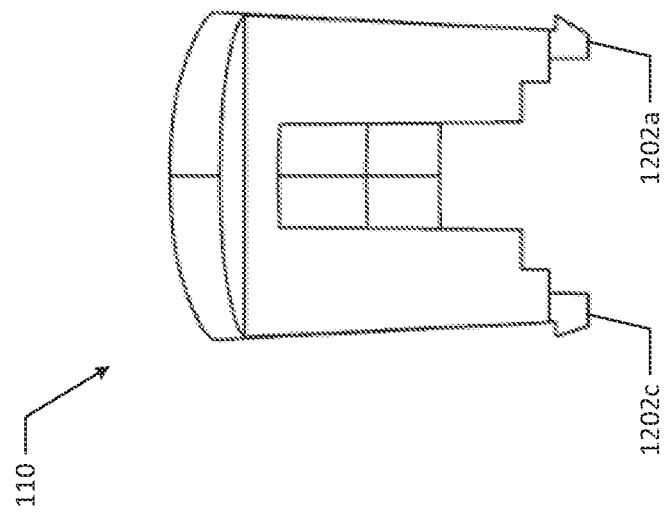
FIGS. 12A, 12B, 12C, 12D and 12E illustrate an example trough of the present disclosure.
Figure 12A:
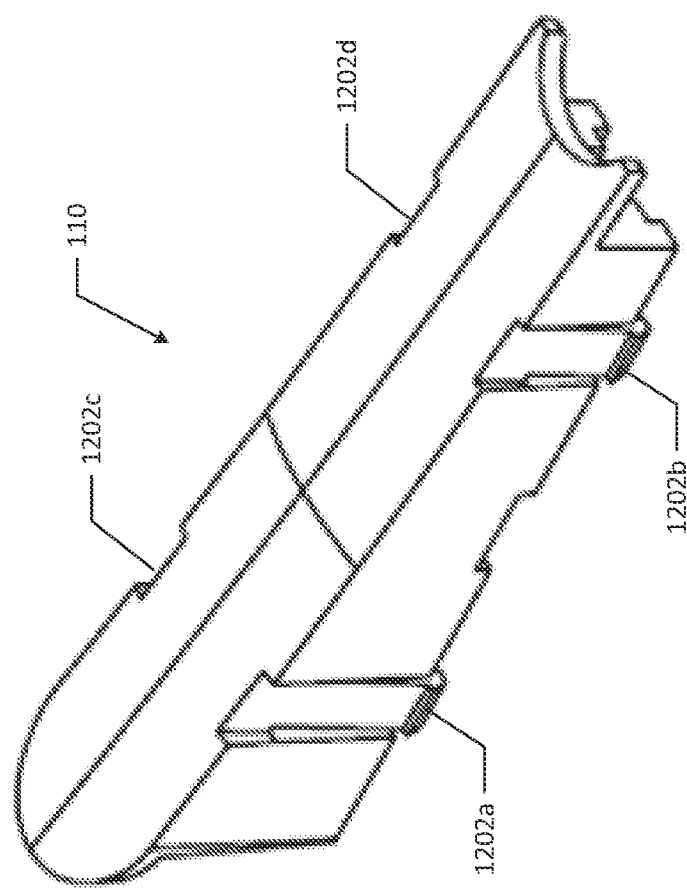
Figure 12C:
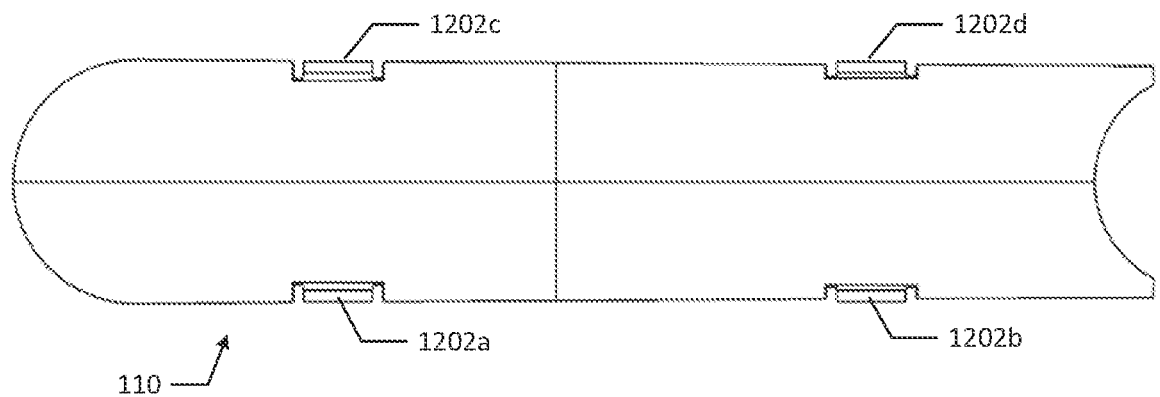
Figure 12D:
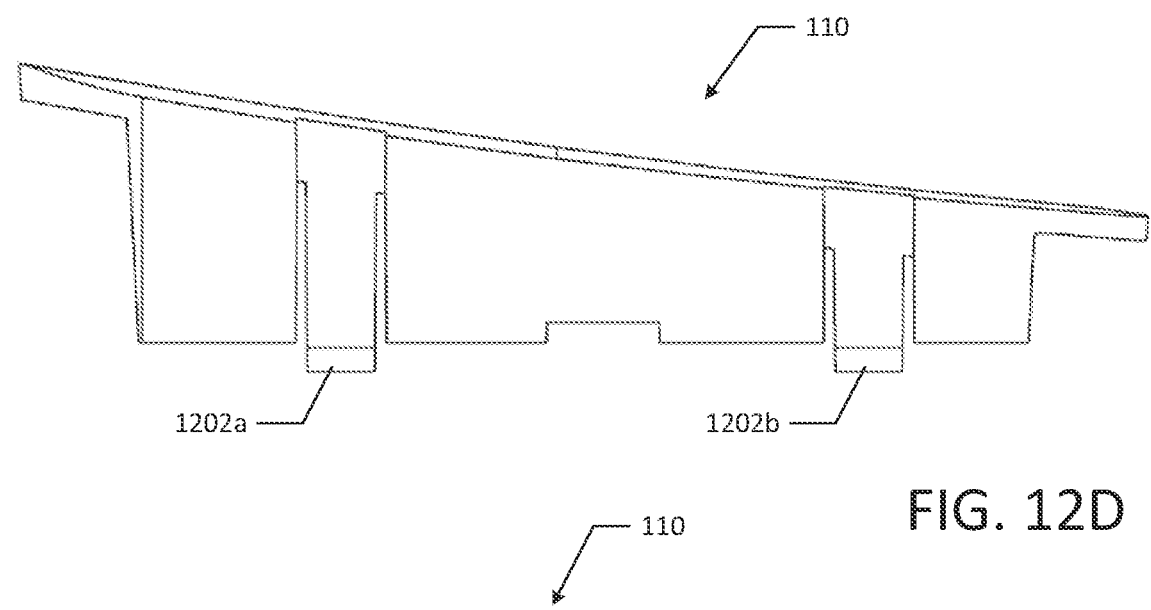
Figure 12E:
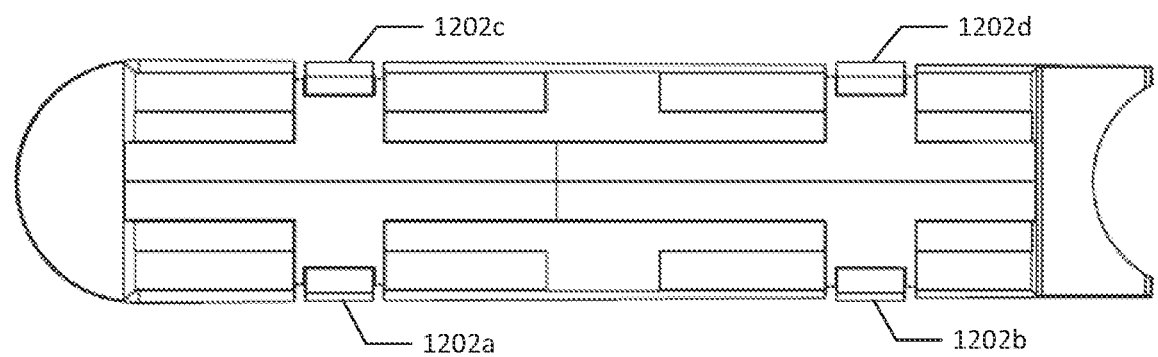

FIGS. 11A to 11E illustrate an example of ratchet pawl 192. The ratchet pawl 192 includes a pawl pin 1102. As discussed above, the pawl pin 1102 is adapted to fit through the opening or thru-hole 550 of the main rail 120 and into the corresponding slot 193 of the bottom housing 104. The ratchet pawl 192 includes a pick 1110 and a positioning post 1120 with flanges 1130*a* and 1130*b*. As illustrated in FIG. 11E, the flanges 1130*a* and 1130*b* form a curved oval-shaped flange, referred to generally as flange 1130, that corresponds to the shape of the pawl slot 552 of the main rail 120. The positioning post 1120 sits within the curved oval-shaped pawl slot 552 of the main rail 120, which allows the ratchet pawl 197 to rotate. The positioning post 1120 may also be coupled to a torsion spring (not pictured) that advances ratchet pawl pick 1110 beyond a respective notch 818*a* or 818*b* (depending on movement in a forward or reverse direction) such that the ratchet pawl pick 1110 can engage teeth 817 of engagement portion 815 of the clip loader assembly 150 (see FIGS. 8B and 8E). For example, the pick 1110 may advance forward along teeth 817 (towards notch 818*a*) when pushing a clip from dispenser 160 and may advance backward along teeth 817 (towards notch 818*b*) when retreating after a clip has been loaded into the jaws.

The ratchet pawl 192 also includes protrusions 1140*a* and 1140*b* that are sized and shaped to extend beyond pawl slot 552 such that the ratchet pawl 192 maintains a level orientation without pivoting or tilting within the pawl slot 552. As noted above, the pawl slot 552 is sized and shaped to allow flange 1130 of the ratchet pawl 192 to pass through the main rail 120 and sit below the main rail 120, thereby allowing the ratchet pawl 192 to rotate while the main rail 120 remains fixedly coupled to the bottom housing 104.

The main rail 120 may be fabricated from plastic or metal. In an example, the main rail 120 is fabricated as a stamped piece(s) of metal. As illustrated in the detail view of FIG. 5E, the pawl slot 552 is a curved oval slot or track that allows the ratchet pawl 192 to rotate within the slot 552.

FIGS. 12A to 12E illustrate an example embodiment of trough 110, which is configured to cover the clip pusher spring 172 within the enclosure of the clip applier 100. The trough 110 may include tabs 1202*a*, 1202*b*, 1202*c* and 1202*d*, hereinafter referred to generally as tabs 1202, that are configured to snap into corresponding mating features on the top housing 102.

Figure 13A:
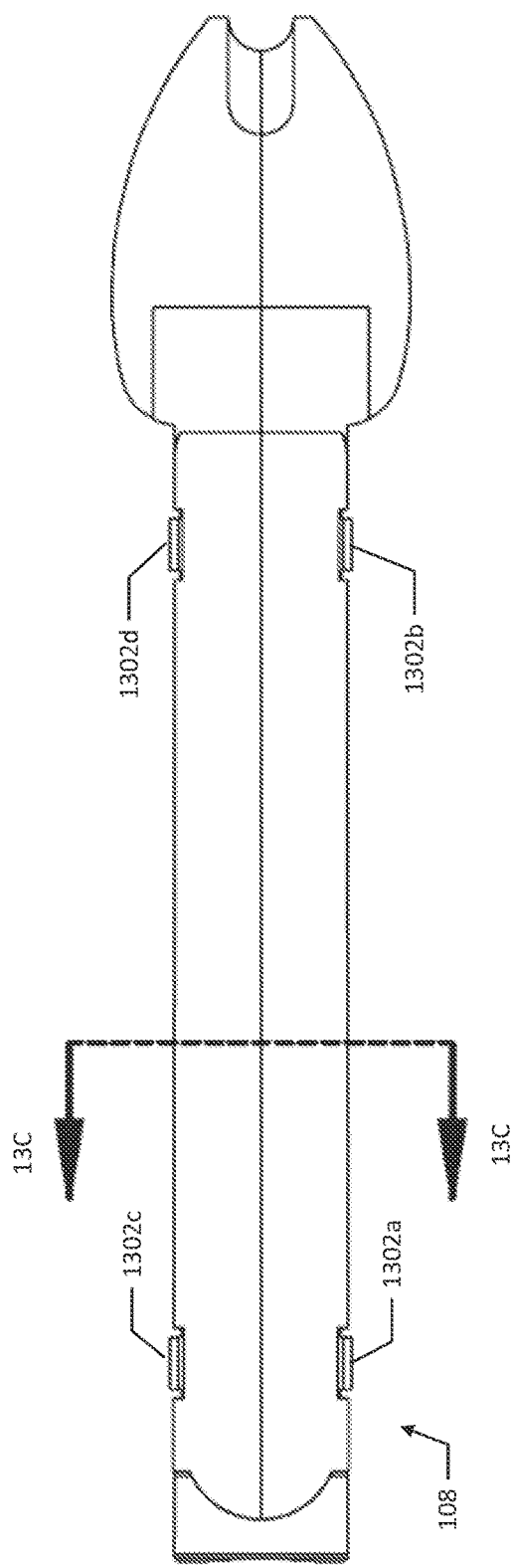
FIGS. 13A, 13B and 13C illustrate an example window cover of the present disclosure.
Figure 13B:
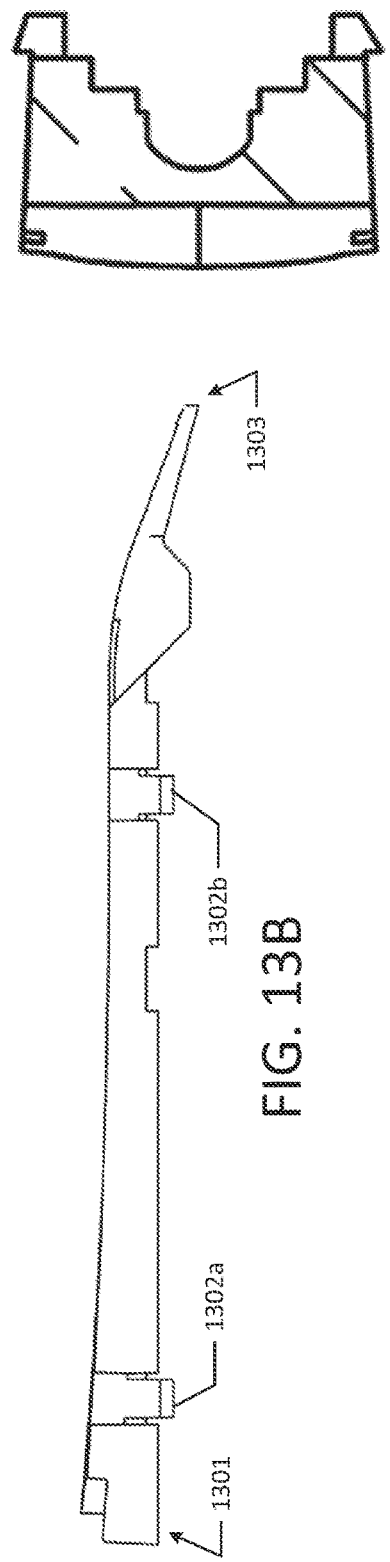
Figure 13C:

FIGS. 13A, 13B and 13C illustrate an example window cover 108. In this example, the window cover 108 and trough 110 are assembled onto the top housing 102 after the remaining surgical clip drive components (e.g., clip pusher assembly 170 are positioned into track or channel formed by the clip dispenser 160) are installed into the clip applier 100. In this example, the window cover 108 provides a transparent window to enable viewing of the surgical clip magazine and clip pusher assembly 170. In this example, the window cover 108 may attach to the top housing 102 via tabs 1302*a*, 1302*b*, 1302*c* and 1302*d*, hereinafter referred to generally as tabs 1302. The tabs 1302 are configured to snap into corresponding mating features on the top housing 102.

The window cover 108 has a proximal end 1301 and a distal end 1303. At the distal end 1303, the window cover 108 is curved and slopes downward to further assist in retaining, guiding and directing surgical clips 50 into the jaw heads of the clip applying jaws 140 (see FIGS. 2B and 2C). The transparent window also enables the user to monitor and track the motion of a surgical clip 50 as it travels through the clip applier 100 to the end of the clip applying jaws 140.

FIGS. 13D, 13E, and 13F illustrate top, side, and cross-section views of another example window cover 108 (e.g., the window cover 108 of FIG. 1K). In this example, the window cover 108 includes a plurality of sockets (interchangeably referred to herein as sockets 1304) exemplified by sockets 1304*a*, 1304*b*, and 1304*c*. Each of the sockets 1304 is configured to attach and/or align with (e.g., in a snap-fit or press-fit engagement, etc.) corresponding connectors or other types of attachment members in a dispenser (e.g., the dispenser 160 of FIG. 1K). Alternatively or additionally, in some examples, the example window cover 108 is crimped or otherwise mechanically attached to a main rail (e.g., the main rail 120 of FIG. 1J).

Figures 14A, 14B:
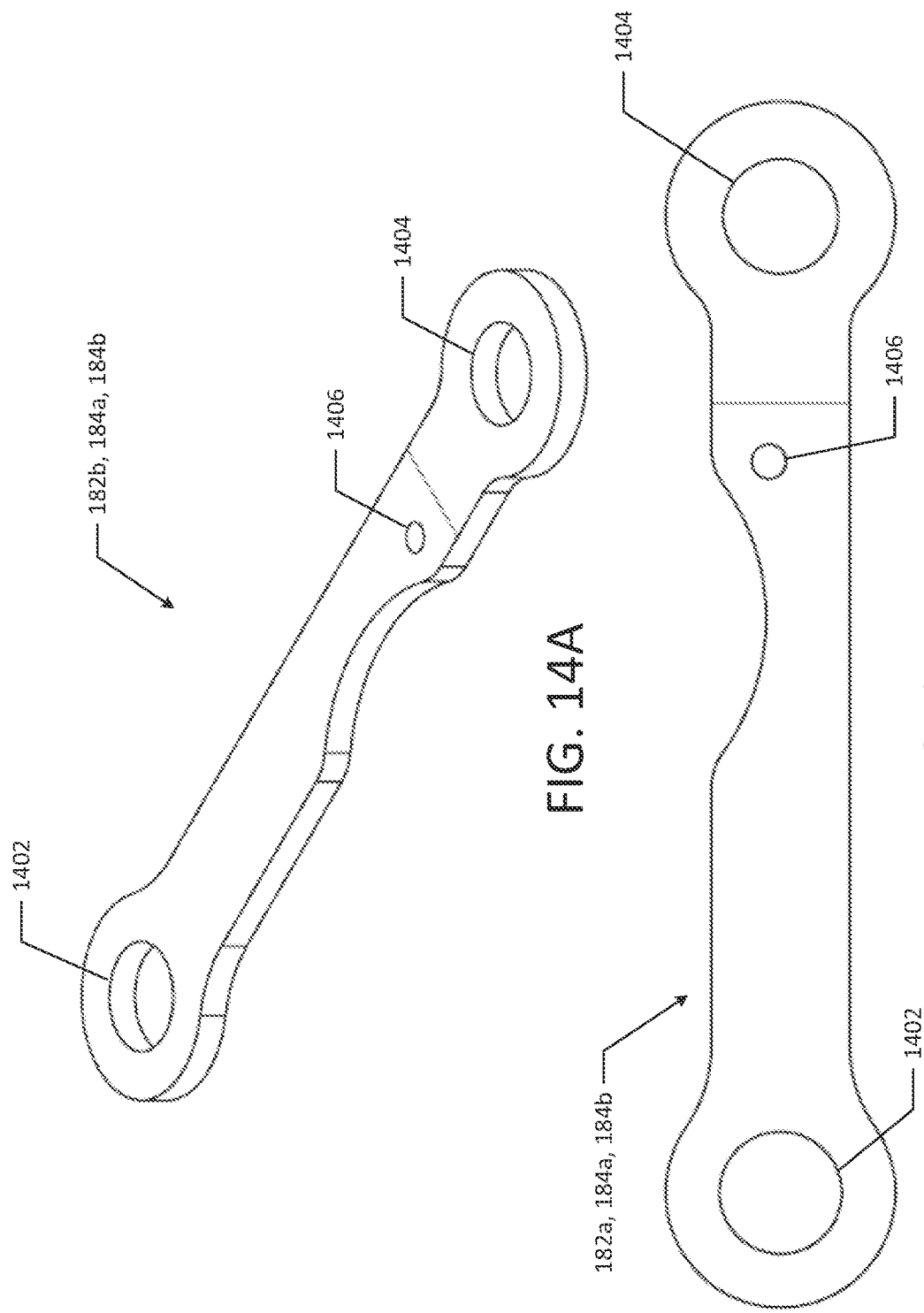
FIGS. 14A and 14B illustrate an example lever of the present disclosure.

FIGS. 14A and 14B illustrate an example embodiment of proximal lever 182*b*, distal lever 184*a* and distal lever 184*b*. As illustrated in FIG. 1B, proximal lever 182*b* may be longer than distal levers 184*a* and 184*b*. Each lever includes two openings or thru-holes 1402 and 1404 on each side of the lever. The levers may be made of metal. In an example, the levers are fabricated as a stamped piece(s) of metal. In one example, the levers made from stainless steel (e.g., 304 SS). Additionally, each lever may include a spring retention slot 1406 (also spring retention slot 1506 for lever 182*a* illustrated in FIG. 15A) adapted to receive and retain an end of either spring 186*a* or spring 186*b*, such that the levers of each lever assembly are spring biased towards each other. Specifically, once spring 186*a* is positioned within spring retention slots 1406 of the proximal lever 182*a* and distal lever 184*a*, the ends of the levers are spring biased towards each other. Similarly, spring 186*b* couples levers 182*b* and 184*b* together.

For each of the proximal lever 182*b*, distal lever 184*a* and distal lever 184*b*, the thru-holes 1402 are adapted to fix one end of each lever to its respective handle via pins 194 (see FIG. 1B). For the proximal lever 182*b*, the thru-hole 1404 corresponds with the drive aperture 830 of the proximal clip loader 154. As noted above, the drive flange 1510 of the proximal lever 182*a* (see FIGS. 15A, 15B and 15C) passes through the bottom of the drive aperture 830 through the proximal clip loader 154 and also extends through the thru-hole 1404 of the proximal lever 182*b*, which controls the linear motion of the clip loader assembly 150 during handle actuation.

The thru-hole 1404 of distal lever 184*b* corresponds with the left drive flange 684 of the jaw closer 130. Similarly, the thru-hole 1404 of distal lever 184*a* corresponds with the right drive flange 682 of the jaw closer 130. The distal levers 184*a*, 184*b* cause the jaw closer 130 to move linearly towards the distal end of the clip applier 100 by urging the drive flanges 682, 684 (and therefore the jaw closer 130) forward during handle actuation.

Figure 15A:
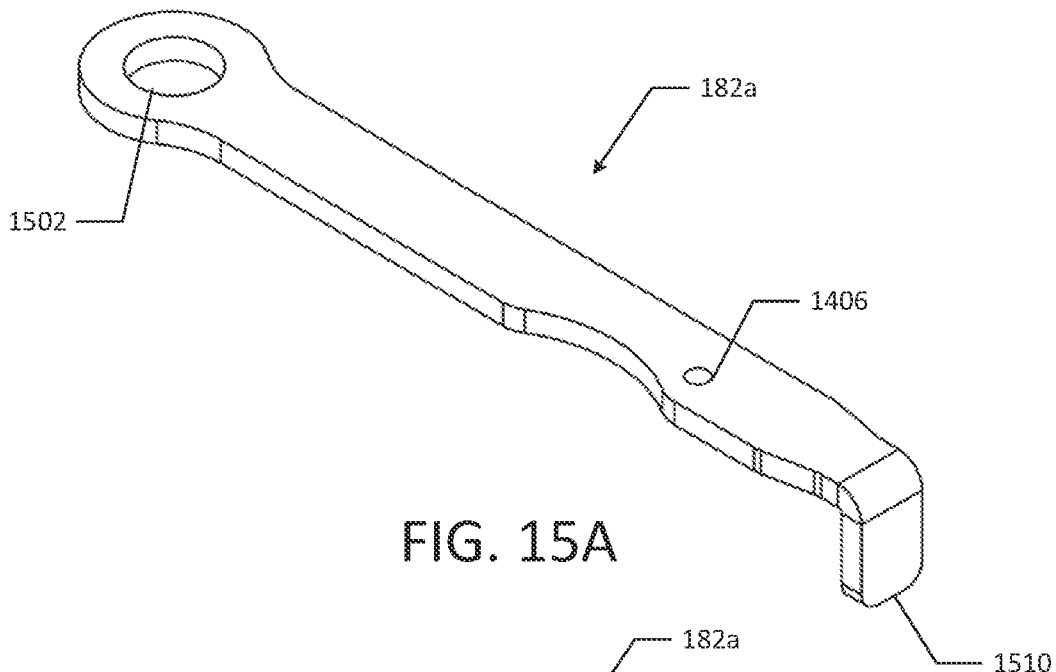
FIGS. 15A, 15B and 15C illustrate an example lever of the present disclosure.
Figure 15B:
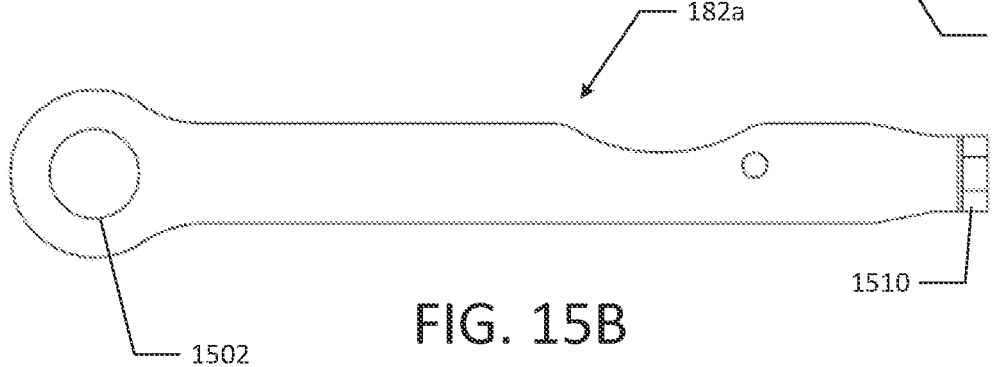
Figure 15C:
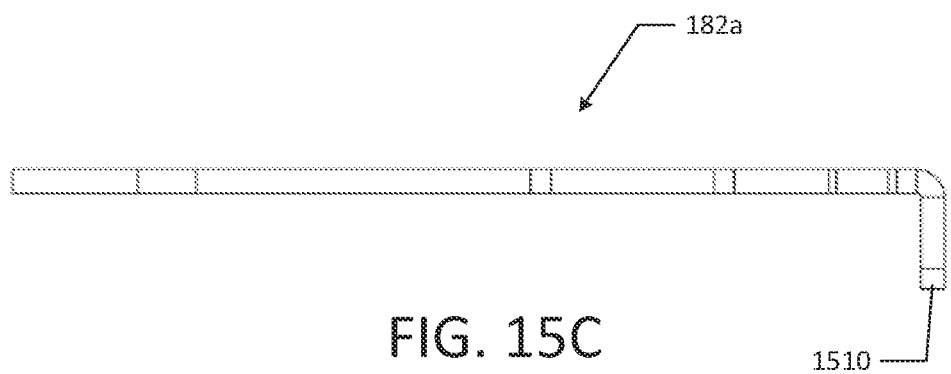

FIGS. 15A, 15B and 15C illustrate an example embodiment of a proximal lever 182*a* of the right lever assembly 180*a*. As illustrated in FIG. 1B, proximal lever 182*a* may be longer than distal levers 184*a* and 184*b*. The proximal lever 182*a* includes an opening or thru-hole 1502 on one side of the lever and a drive flange 1510 on the opposite end. The proximal lever 182*a* may be made of metal. In an example, the proximal lever 182*a* is fabricated as a stamped piece(s) of metal. In one example, the proximal lever 182*a* is made from stainless steel (e.g., 304 SS). Additionally, the proximal lever 182*a* may include a spring retention slot 1506 adapted to receive and retain an end of the spring 186, such that the levers of each lever assembly are spring biased towards each other. For example, spring retention slot 1506 may provide the same functionality and have the same features as spring retention slot 1406 described in FIG. 14A.

The thru-hole 1502 is adapted to fix one end of the proximal lever 182*a* to its respective handle via pin 194 (see FIG. 1B). As noted above, the drive flange 1510 of the proximal lever 182*a* (see FIGS. 15A, 15B and 15C) passes through the bottom of the drive aperture 830 through the proximal clip loader 154 and also extends through the thru-hole 1404 of the proximal lever 182*b*, which controls the linear motion of the clip loader assembly 150 during handle actuation.

Figure 16B:
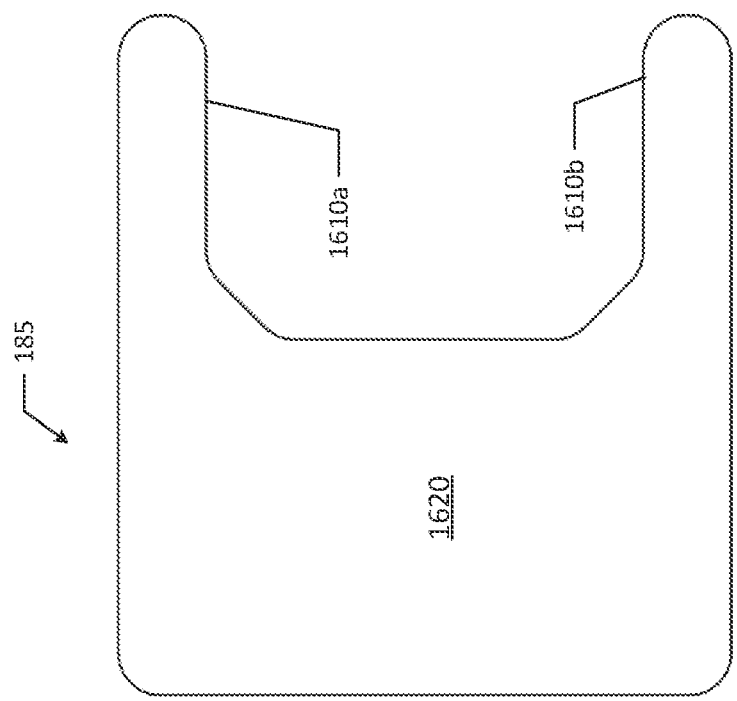
FIGS. 16A and 16B illustrate an example lock-out clip of the present disclosure.
Figure 16A:
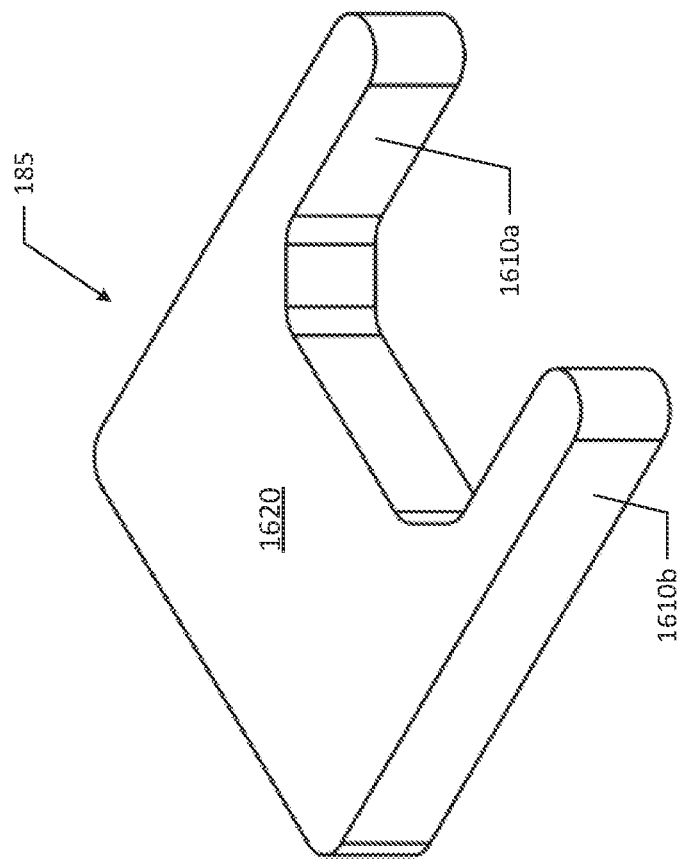

FIGS. 16A and 16B illustrate an example lock-out clip 185. The lock-out clip 185 may include two legs 1610*a* and 1610*b* that are sized and shaped similar to the legs of a surgical clip, such that the lock-out clip 185 may advance through the clip applier 100 and into the clip track 770 formed by jaw heads 730 of the clip applying jaws 140. However, the lock-out clip 185 also includes a resilient section 1620 that has sufficient rigidity and strength to prevent the clip applying jaws 140 from closing. For example, when the resilient section is positioned within the clip track 770, the strength and stiffness of the resilient section 1620 advantageously prevents the clip applying jaws 140 from closing, thereby preventing the clinician from unintentionally closing the clip applying jaws 140 when a surgical clip is not present. In some examples, the lock-out clip 185 (including the resilient section 1620) is formed from a titanium grade 5 material, and other clips (e.g., clip 50 or any other clip of the stack 105 illustrated in FIG. 1K) is formed from a titanium grade 1 material. In alternative examples, the lock-out clip 185, the clip 50 (shown in FIG. 1K), and/or the stack 105 (shown in FIG. 1K) are formed from one or more different materials.

Figure 16C:
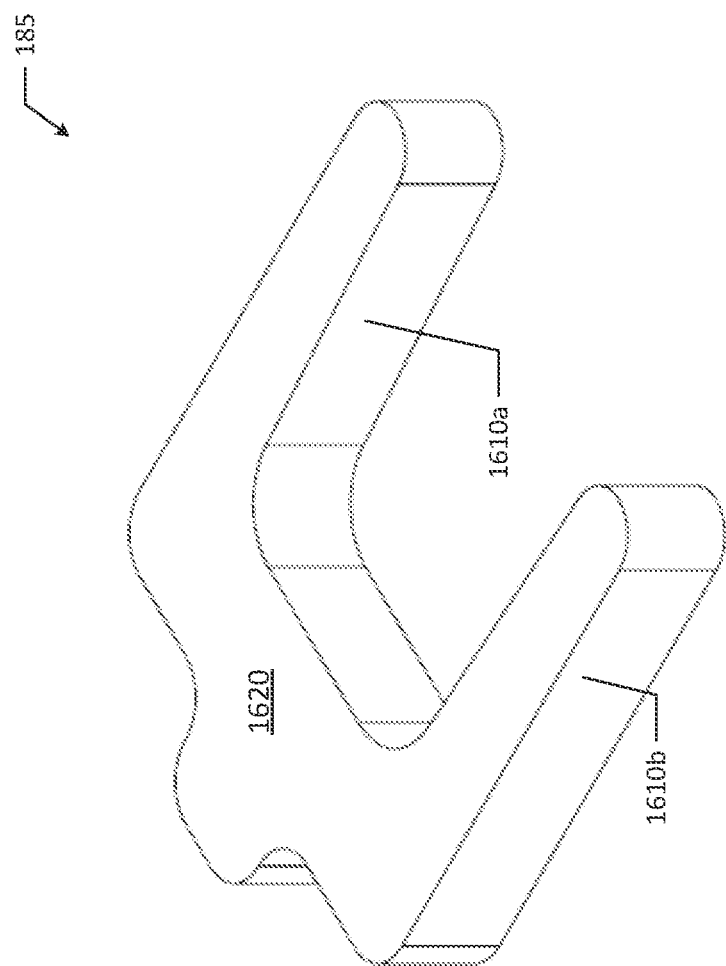
FIG. 16C illustrates another example lock-out clip of the present disclosure.
Figures 17A, 17B:
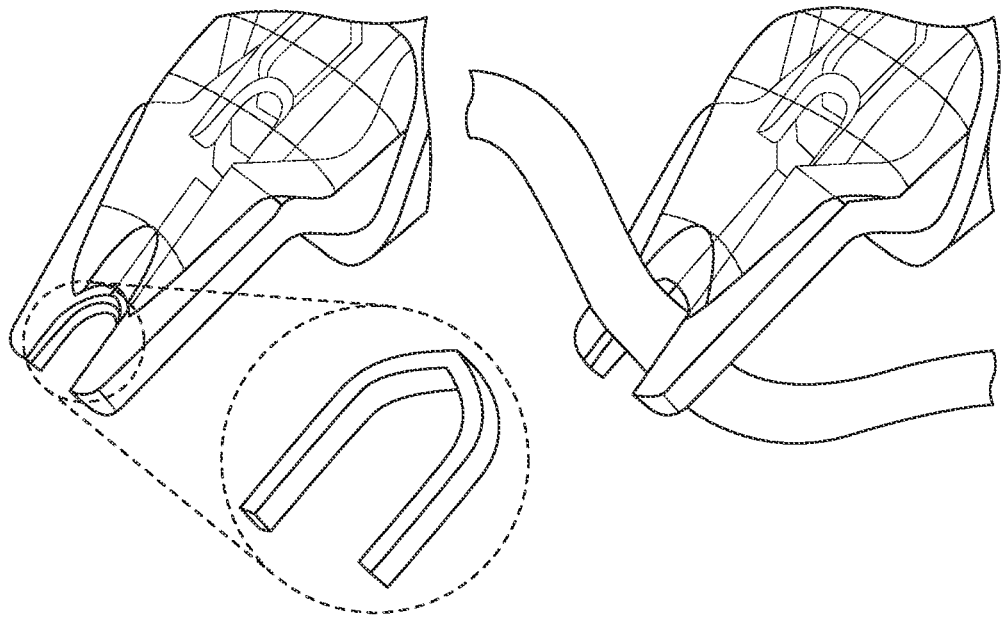
FIGS. 17A, 17B, 17C, 17D, 17E, 17F and 17G illustrate the clip applier in various orientations while applying a clip according to examples of the present disclosure.
Figures 17C, 17D:
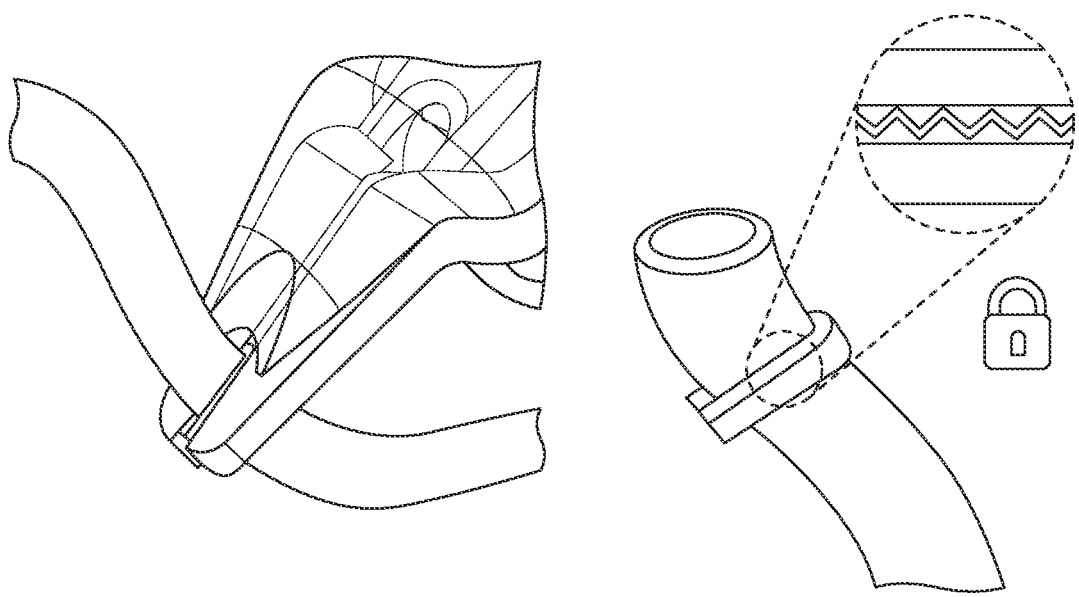
Figure 17E:
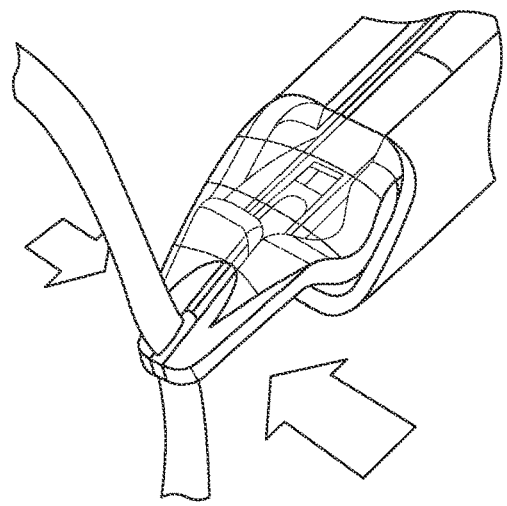
Figure 17F:
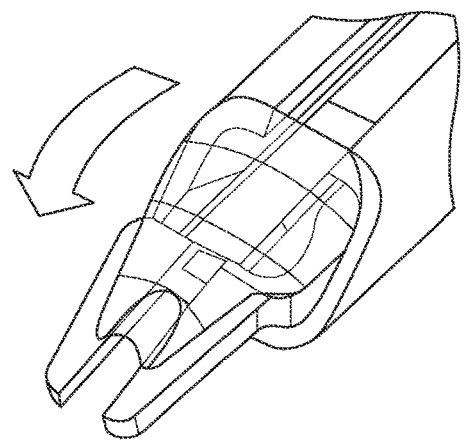
Figure 17G:
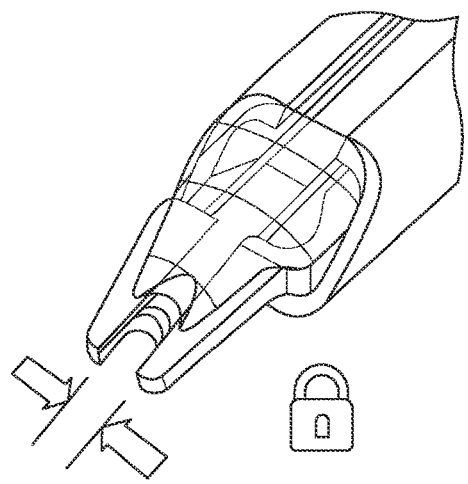

FIG. 16C illustrates another example lock-out clip 185 (e.g., the lock-out clip 185 of FIG. 1K). Similar to the example lock-out clip 185 of FIGS. 16A-16B, the example lock-out clip 185 of FIG. 16C includes two legs 1610a, 1610b and a resilient section 1620. For example, a shape of the leg 1610a, the 1610b, and/or the resilient section 1620 of the lock-out clip 185 of FIG. 16C may vary from a corresponding shape of a corresponding component of the lock-out clip 185 of FIGS. 16A-16B.

FIGS. 17A, 17B, 17C, 17D, 17E, 17F and 17G illustrate the jaw portion of the clip applier 100 in various stages of loading a surgical clip 50, crimping the surgical clip 50, and applying the surgical clip 50 to ligate a vessel.

It should be appreciated that for each component with multiple or alternative embodiments, each or any of the embodiments may include the same or similar features as a previously described or a later described embodiment. Specifically, any of the components or features illustrated in FIG. 1B, which are illustrated or described in more detail with relation to other figures, may be attributed to any of the components or features illustrated in FIG. 1C and vice versa.

Additionally, it should be appreciated that some example embodiments herein may include fewer or more components than other example embodiments. For instance, some example embodiments of the clip application device 100 herein can be implemented without one or more of the ratchet prawl 192, the trough 110, and/or any other component (e.g., pin, screw, etc.) used in other example embodiments of the clip application device 100.

Aspects of the subject matter described herein may be useful alone or in combination with one or more other aspects described herein. In an example, a surgical clip applying device includes an enclosure formed from a top housing, a bottom housing and a window cover. The clip applying device also includes a pair of handles including a left handle and a right handle, a main rail supporting a jaw closer, and a pair of clip applying jaws fixedly attached to the bottom housing and retained within the main rail. The pair of clip applying jaws has arms terminating with a pair of jaw heads. Additionally, the clip applying device includes a clip loader assembly with a clip loading tip at the clip loader assembly's distal end and a dispenser positioned above the clip loader assembly. The dispenser includes a pair of clip forks and a retention prong positioned between the pair of clip forks at the dispenser's distal end. The clip loading tip is configured to push a surgical clip supported by the pair of clip forks over the retention prong. The clip applying device also includes a clip pusher assembly configured to advance a plurality of clips towards the pair of jaw heads and a drive mechanism including a plurality of levers and at least one spring. The drive mechanism is configured to translate an actuation of the pair of handles to linear motion of the jaw closer and the clip loader assembly.

In another aspect of the present disclosure, the jaw closer includes an indent with cam members at its distal end. The cam members are configured to engage and compress corresponding ramps on the arms of the clip applying jaws thereby forcing the arms and the jaw heads together as the jaw closer is advanced towards the jaw heads.

In another aspect of the present disclosure, the clip applying device includes a lock-out clip.

In another aspect of the present disclosure, the lock-out clip is sized and shaped to advance into the jaw heads.

In another aspect of the present disclosure, the lock-out clip is configured to prevent the clip applying jaws from closing once positioned within the jaw heads.

To the extent that any of these aspects are mutually exclusive, it should be understood that such mutual exclusivity shall not limit in any way the combination of such aspects with any other aspect whether or not such aspect is explicitly recited. Any of these aspects may be claimed, without limitation, as a system, method, apparatus, device, medium, etc.

The many features and advantages of the present disclosure are apparent from the written description, and thus, the appended claims are intended to cover all such features and advantages of the disclosure. Further, since numerous modifications and changes will readily occur to those skilled in the art, the present disclosure is not limited to the exact construction and operation as illustrated and described. Therefore, the described embodiments should be taken as illustrative and not restrictive, and the disclosure should not be limited to the details given herein but should be defined by the following claims and their full scope of equivalents, whether foreseeable or unforeseeable now or in the future.

The invention is claimed as follows:

1. A surgical clip applying device comprising:
   an enclosure formed from a top housing, a bottom housing and a window cover;
   a pair of handles including a left handle and a right handle each mounted for pivotal movement in the bottom housing;
   a main rail fixedly mounted to the bottom housing within the enclosure including an elongate base and upstanding sidewalls defining a U-shaped channel;
   a pair of clip applying jaws fixedly attached to the bottom housing and mounted through the main rail, the pair of clip applying jaws having arms terminating with a pair of spaced opposing jaw heads and including a pair of angled ramp surfaces disposed in said arms spaced inwardly from said jaw heads;
   a jaw closer comprising an elongate base including a pair of upstanding drive flanges disposed at a proximal end of the jaw closer, the elongate base including a V-shaped indent at a distal end of the jaw closer defining cam members at its distal end and an elongate slot defined in the base intermediate the distal end and proximal end of the jaw closer, the jaw closer being disposed between the clip applying jaws and the base of the rail and mounted for slideable movement in the channel toward and away from the jaw heads, the cam members being configured to engage and compress corresponding ramp surfaces on the arms of the clip applying jaws thereby forcing the arms and the jaw heads together as the jaw closer is advanced towards the jaw heads; and
   a drive mechanism including a plurality of levers and at least one spring, connecting the handles to the upstanding drive flanges of the jaw closer, the drive mechanism configured to translate an actuation of the pair of handles to linear motion of the jaw closer.

2. The surgical clip applying device as defined in claim 1, further comprising:
- a clip loader assembly disposed in the enclosure above the clip applying jaws including a clip loading tip at a distal end of the clip loader assembly and a drive aperture at the proximal end of the clip loader assembly;
- a dispenser positioned above the clip loader assembly, the dispenser including a pair of clip forks and a retention prong positioned between the pair of clip forks at the distal end of the dispenser, wherein the clip loading tip is configured to push a surgical clip supported by the pair of clip forks over the retention prong;
- a clip pusher assembly configured to advance a plurality of clips towards the pair of jaw heads; and
- a drive mechanism including a plurality of levers and at least one spring, connecting the handles to the drive aperture of the clip loader assembly, the drive mechanism configured to translate an actuation of the pair of handles to linear motion of the jaw closer and clip loader clip loader assembly.

3. The surgical clip applying device of claim 2, further comprising a lock-out clip.

4. The surgical clip applying device of claim 3, wherein the lock-out clip is sized and shaped to advance into the jaw heads.

5. The surgical clip applying device of claim 4, wherein the lock-out clip is configured to prevent the clip applying jaws from closing once positioned within the jaw heads.

6. The surgical clip applying device as recited in claim 2, wherein the clip loader assembly and the drive mechanism provide automatic surgical clip reloading to the jaws as the handles move from a closed position to an open position.

7. The surgical clip applying device as recited in claim 2, wherein the window cover provides visibility to a clip count of surgical clips loaded in the dispenser.

\* \* \* \* \*